(12) United States Patent
Mao et al.

(10) Patent No.: US 10,570,463 B2
(45) Date of Patent: Feb. 25, 2020

(54) NUCLEIC ACID MODIFYING AGENTS AND USES THEREOF

(71) Applicant: BIOTIUM, INC., Fremont, CA (US)

(72) Inventors: Fei Mao, Fremont, CA (US); Patrick Gordon McGarraugh, San Francisco, CA (US); Alexis Spain Madrid, Fremont, CA (US); Wai-Yee Leung, San Ramon, CA (US); Lori M. Roberts, Belmont, CA (US)

(73) Assignee: BIOTIUM, INC., Fremont, CA (US)

( * ) Notice: Subject to any disclaimer, the term of this patent is extended or adjusted under 35 U.S.C. 154(b) by 88 days.

(21) Appl. No.: 15/522,522

(22) PCT Filed: Oct. 29, 2015

(86) PCT No.: PCT/US2015/058112
§ 371 (c)(1),
(2) Date: Apr. 27, 2017

(87) PCT Pub. No.: WO2016/069922
PCT Pub. Date: May 6, 2016

(65) Prior Publication Data
US 2018/0142283 A1 May 24, 2018

Related U.S. Application Data

(60) Provisional application No. 62/072,330, filed on Oct. 29, 2014.

(51) Int. Cl.
| | |
|---|---|
| *C12Q 1/68* | (2018.01) |
| *C12Q 1/689* | (2018.01) |
| *C07D 221/08* | (2006.01) |
| *C07D 221/12* | (2006.01) |
| *C07D 513/02* | (2006.01) |
| *C07D 513/14* | (2006.01) |
| *C12Q 1/6809* | (2018.01) |
| *C12Q 1/6816* | (2018.01) |

(52) U.S. Cl.
CPC .......... *C12Q 1/689* (2013.01); *C07D 221/08* (2013.01); *C07D 221/12* (2013.01); *C07D 513/02* (2013.01); *C07D 513/14* (2013.01); *C12Q 1/6809* (2013.01); *C12Q 1/6816* (2013.01); *C12Q 2563/107* (2013.01); *C12Q 2563/131* (2013.01); *C12Q 2563/173* (2013.01)

(58) Field of Classification Search
CPC .................................................. C12Q 1/689

USPC ......................................................... 435/6.1
See application file for complete search history.

(56) References Cited

U.S. PATENT DOCUMENTS

| | | |
|---|---|---|
| 6,187,572 B1 | 2/2001 | Platz et al. |
| 6,242,430 B1 | 6/2001 | Suzuki et al. |
| 7,776,567 B2 | 8/2010 | Mao et al. |
| 2006/0211028 A1 | 9/2006 | Mao et al. |
| 2006/0211029 A1 | 9/2006 | Mao et al. |
| 2010/0035250 A1 | 2/2010 | Nocker et al. |
| 2011/0136201 A1 | 6/2011 | Mao et al. |

OTHER PUBLICATIONS

Bailly, et al. Molecular determinants for DNA minor groove recognition: design of a bis-guanidinium derivative of ethidium that is highly selective for AT-rich DNA sequences. Biochemistry. Feb. 15, 2005;44(6):1941-52.
European search report with written opinion dated Jul. 11, 2018 for EP Application No. 15853804.
Stojkovic, et al. Permanent positive charge strongly influences DNA/RNA binding and antiproliferative activity of urea-phenanthridinium conjugates. Eur J Med Chem. Aug. 2010;45(8):3281-92. doi: 10.1016/j.ejmech.2010.04.006. Epub Apr. 14, 2010.
Tumir, et al. Come-back of phenanthridine and phenanthridinium derivatives in the 21st century. Beilstein J Org Chem. Dec. 10, 2014;10:2930-54. doi: 10.3762/bjoc.10.312. eCollection 2014.
Tumir, et al. Synthesis of phenanthridinium-bis-nucleobase conjugates, interactions with poly U, nucleotides and in vitro antitumour activity of mono- and bis-nucleobase conjugates. Eur J Med Chem. Oct. 2006;41(10):1153-66. Epub Jun. 21, 2006.
Unknown: "8.1 Nucleic Acid Stains", 269 Section, Mar. 1, 2003, XP055454292, Retrieved from the Internet: URL: http://www.mobitech.de/probes/docs/sections/0801.pdf.
International search report dated Mar. 4, 2016 for PCT Application No. PCT/US15/58112.
PubChem-CID-24841204 Create Date: Jul. 11, 2008, p. 3, Fig.
PubChem-CID-54463202 Create Date: Dec. 4, 2011, p. 3, Fig.

*Primary Examiner* — Jezia Riley
(74) *Attorney, Agent, or Firm* — Wilson Sonsini Goodrich & Rosati

(57) ABSTRACT

In some aspects, the disclosure provides compounds comprising nucleic acid modifying moieties, such as nucleic acid binding dyes comprising activatable groups. In some aspects, the disclosure provides nucleic acid probes comprising compounds of the disclosure, and methods of making the same. In some aspects, the disclosure provides methods of using compounds of the disclosure, such as methods of labeling and/or detecting non-viable organisms or non-viable cells, and methods of detecting contamination or infection.

14 Claims, 8 Drawing Sheets

NUCLEIC ACID MODIFYING AGENTS AND USES THEREOF

CROSS REFERENCE

This application is a national stage entry of PCT/US2015/058112, filed Oct. 29, 2015, which claims priority to U.S. Provisional Application No. 62/072,330, filed Oct. 29, 2014, each of which application is incorporated herein by reference in its entirety.

BACKGROUND OF THE INVENTION

Accurate and rapid detection of microorganisms, such as bacteria and viruses, has important applications in many areas including biodefense, food safety, diagnostics, pathology, forensics and drug discovery. Many food products, for example, especially processed meat, vegetables and dairy products are probable carriers of potent food-borne pathogens, including *E. coli, Salmonella, Listeria* and *Campylobacter jejuni*. In fact, there have been numerous incidents of costly food product recalls across United States in past years, which might have been preventable or minimized if reliable early detection could have been made. As another example, in hospitals and other healthcare facilities, presence of pathogens can pose health risks to both patients and care takers. Thus, the microbial environment in these facilities must be constantly monitored to prevent disease transmission. The accurate diagnosis, prognosis and effective treatment of infectious diseases also rely on the precise identification of the pathogenic species responsible.

The classical method for microorganism detection is based on cell culture, where a sample is collected and then cultured to grow enough of the microorganism species to be detected. In the case of bacteria, colonies of the bacteria can be counted visually under a microscope. A major drawback of the culture method is that it can sometimes take days for the culture to grow. Another problem is that not all microorganisms can be cultured because some microorganisms can only survive under certain narrow conditions as may be defined by pH, temperature, nutrient composition and the co-presence of other microorganisms, for example. Immunology-based microorganism detection is one alternative method. In this method, proteins, such as toxins, associated with the microorganisms are detected using antibodies. However, this method suffers a general lack of high quality antibodies, and higher cost can be a problem. Another more recently developed method is based on the detection of microbial DNA or RNA using polymerase chain reaction (PCR). In this method, a nucleic acid sequence unique to a particular microorganism species is selectively amplified and analyzed. The PCR-based detection method is highly accurate and relatively fast, taking only a few hours, instead of days, to complete. The methods also permit simultaneous detection of multiple microorganism species when different fluorescently labeled probes are used. Despite some of the obvious advantages of these genetically based test methods, nucleic acid amplification is a required step, which has the problem of not being able to distinguish between nucleic acid from live cells and that from dead ones.

Recently, so-called viability PCR has been developed to overcome the live cell selectivity problem. A key to the technique is the use of a DNA modifier dye, propidium monoazide (PMA). PMA is a doubly-positively charged DNA binding dye with a photoreactive azido group, which upon photolysis undergoes crosslinking with DNA, thereby covalently modifying the nucleic acid with the dye. When the DNA is sufficiently modified, it loses its biological activity, being unable to serve as template in polymerase chain reaction. Another property of PMA is that in a typical viability PCR-based detection, a sample comprising both live and dead cells is first treated with PMA in the presence of light. Since dead cells have a compromised cell membrane, their DNA is exposed for PMA modification; whereas, viable cells, which have cell membrane to prevent PMA from getting into contact with their nucleic acid, are often unaffected by the treatment. In the subsequent step, viable cells are then lysed to expose their DNA for selective amplification.

Although PMA has proven useful for the detection of a number of microorganism species under some conditions, it does not work well or completely fails to work for some organisms under certain conditions. For example, some results indicate that relatively short amplicons are not affected by PMA treatment. Other results indicate that for *Staphylococcus aureus* samples collected by swabbing from surfaces, PMA does not allow the determination of amount of living cells, which has been attributed to PMA dye getting into viable cells that were collected using that particular procedure. It has also been reported that, when PMA qPCR was used to detect *Mycobacterium avium* subspecies *paratuberculosis* (MAP), a gram-positive bacterium, the dye was found to enter viable MAP, causing underestimation of the number of viable cells. PMA has also been found to enter viable *Salmonella* serovar *Enteritidis* and in the meantime ineffective in suppressing qPCR signal from the killed bacteria.

SUMMARY OF THE INVENTION

In view of the foregoing, there exists a need for improved compounds for nucleic acid detection, particularly for distinguishing between viable and non-viable organisms and cells. This disclosure provides compounds and methods that address this need, and provide other advantages as well.

In one aspect, provided herein, is a compound having the formula:

   Formula A' wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In another aspect, the disclosure provides a compound having the formula:

   Formula A wherein, A is a nucleic acid modifying moiety (NAMM) comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, M comprises a detectable label.

In some embodiments, the activatable group is a photoaffinity label selected from the group consisting of an azide, a benzophenone, and a diazirine. In some embodiments, the activatable group is a furan, an enediyne, or a metal complex such as a ruthenium complex or a platinum complex. In some embodiments, the polyhydroxy moiety is a sugar, dextrin, or cyclodextrin. In some embodiments, the detectable label is fluorescent dye label, biotin, digoxigenin, or a hapten. In some embodiments, A is an azido-substituted nucleic acid binding dye. In some embodiments, the nucleic acid binding dye is selected from the group consisting of phenanthridium, cyanine, acridine, acridinium, and Hoechst dyes. In some embodiments, M comprises a poly(ethylene glycol) and a positively charged group. In some embodiments, M comprises a poly(ethylene glycol) and one or two negatively charged groups. In some embodiments, M is a substituent having a molecular mass from 200-1500 Da. In some embodiments, M comprises a functional group capable of forming a covalent linkage with a detectable label. In some embodiments, M comprises a functional group capable of forming a covalent linkage with a detectable label, wherein the functional group is selected from the group consisting of a primary or secondary amine, a CLICK chemistry reaction partner (e.g. an alkyne or an azido group), an aldehyde, a hydrazine, and a hydroxylamine.

In some embodiments of the compound of Formula A or Formula A', the compound has structure of Formula B:

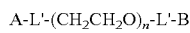     Formula B wherein, A is a nucleic acid modifying moiety (NAMM) comprising an activatable group capable of crosslinking with or cleaving a target nucleic acid, each L' is independently a single bond or a linker comprising 1-15 atoms selected from the group consisting of C, N and O; n is an integer from 2-40 inclusive; and B is a moiety comprising at least one of the moieties selected from the group consisting of a negatively charged group, a positively charged group, and a detectable label. In some embodiments, at least one L' is a linker comprising 4-10 atoms selected from the group consisting of C, N and O; and n is an integer from 2-24 inclusive. In some embodiments, each L' is independently a bond, —($C_1$-$C_{12}$ alkyl)- or —($C_1$-$C_{12}$ alkyl)-C(O)NH—. In some embodiments, A is nucleic acid binding dye comprising an activatable group capable of crosslinking with or cleaving a target nucleic acid. In some embodiments, B is selected from the group consisting of an amino acid, dipeptide, cysteic acid, cysteine, $C_1$-$C_{12}$ alkyl comprising an amide, $C_1$-$C_{12}$ alkyl substituted with a carboxylic acid, and $C_1$-$C_{12}$ alkyl substituted with a trialkylammonium salt. In some embodiments, B comprises a negatively charged group selected from the group consisting of —$SO_3^-$, —$CO_2^-$, and —$PO_3^{2-}$. In some embodiments, B comprises a positively charged group that is a trialkylammonium group.

In some embodiments, the nucleic acid binding dye of Formula A' has the structure of Formula C or Formula D:

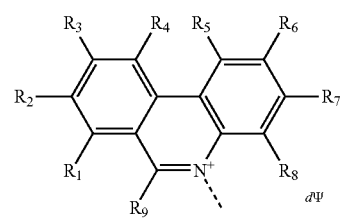

Formula C

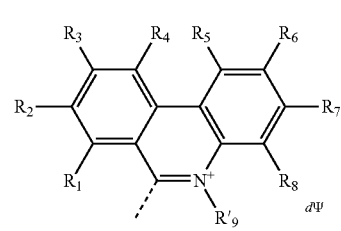

Formula D wherein the dashed line indicates the attachment site for the substituent M; $R_1$, $R_2$, $R_3$, $R_4$, $R_5$, $R_6$, $R_7$ and $R_8$ are independently selected from the group consisting of H, F, Cl, Br, $C_1$-$C_2$ alkyl, $C_1$-$C_2$ alkoxy, amino and $C_1$-$C_2$ alkyl or dialkylamino, amidino, guanidino, and azide; $R_9$ is a substituted or unsubstituted alkyl, substituted or unsubstituted aryl or substituted or unsubstituted heteroaryl; $R'_9$ is a substituted or unsubstituted alkyl; and wherein at least one of $R_1$, $R_2$, $R_3$, $R_4$, $R_5$, $R_6$, $R_7$ or $R_8$ is azide (—$N_3$); $\Psi$ comprises a biologically compatible counter ion; and d is a number of $\Psi$ sufficient to render overall charge of the compound neutral.

In some embodiments, the compound has the structure:

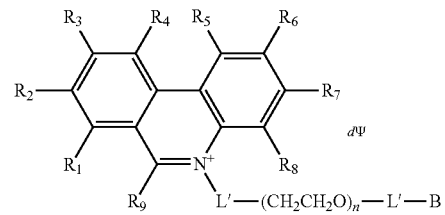

wherein $R_1$, $R_3$, $R_4$, $R_5$, $R_6$ and $R_8$ are independently H or F; wherein at least one of $R_2$ and $R_7$ is $N_3$ and any other remaining $R_2$ and $R_7$ is $NH_2$; $R_9$ is phenyl; each L' is independently a single bond or a linker comprising 1-15 atoms selected from the group consisting of C, N and O; n is an integer from 2-40 inclusive; and B is a moiety comprising at least one of the moieties selected from the group consisting of a negatively charged group, a positively charged group, and a detectable label; $\Psi$ comprises a biologically compatible counter ion; and d is a number of $\Psi$ sufficient to render overall charge of the compound neutral.

In some embodiments, the nucleic acid binding dye of Formula A' has the structure of Formula E:

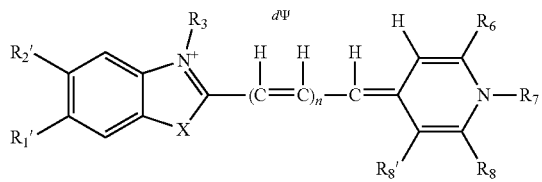

(Formula E)

wherein $R_1'$ or $R_2'$ of Formula E is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; —C(=O)NH$R_{15}$ or $N_3$; or a substituent associated with minor groove binding; or represents where M attaches to the structure; when $R_1'$ or $R_2'$ of Formula E comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl; when $R_1'$ or $R_2'$ of Formula E comprises $R_{11}$ and $R_{12}$, $R_{11}$ and $R_{12}$ may in combination form a 5- or 6-membered, saturated or unsaturated ring, which optionally comprises at least one hetero atom selected from N and O; $R_3$ of Formula E is $C_1$-$C_3$ alkyl; X of Formula E is selected from O and S; n of Formula E is selected from 0, 1, and 2; $R_6$ of Formula E is H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; —$N_3$; or a substituted or an unsubstituted aryl, optionally comprising 1 to 3 hetero atom(s), inclusive, selected from N, O, and S; or represents where L attaches to the structure; $R_7$ of Formula E is H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from N, O, and S; or represents where M attaches to the structure; $R_8$ and $R_8'$ of Formula E in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen; each of $R_{16}$ and $R_{17}$ independently is H; alkyl having 1 carbon to 12 carbons, inclusive, optionally incorporating 1 to 2 nitrogen(s) or an aryl; or $R_{16}$ and $R_{17}$ may in combination form a 5- or 6-membered saturated or unsaturated ring, which optionally comprises at least one hetero atom selected from N and O; only one of $R_1'$, $R_2'$, $R_6$, and $R_7$ of Formula E represents where M attaches to the structure; at least one of $R_1'$, $R_2'$ and $R_6$, is —$N_3$; Ψ of Formula E comprises a biologically compatible counter ion; and d is a number of Ψ sufficient to render overall charge of the compound neutral.

In some embodiments, the nucleic acid binding dye of Formula A' has the structure of Formula F:

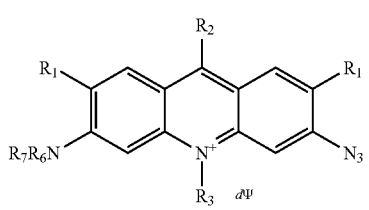

(Formula F)

wherein each $R_1$ of Formula F is independently H or a C1-C2, inclusive, alkyl; one of $R_2$ and $R_3$ of Formula F represents where M attaches to the structure; when $R_2$ represents where M attaches to the structure, $R_3$ is H or —$CH_3$; when $R_3$ represents where M attaches to the structure, $R_2$ is selected from H, —$CH_3$, —$NH_2$, —$NHCH_3$, —CN, and —C(=O)$NH_2$; $R_6$ of Formula F is independently H or a C1-C2, inclusive, alkyl; $R_7$ of Formula F is independently H or a C1-C2, inclusive, alkyl; for a pair of $R_6$ or $R_7$ and adjacent $R_1$, independently, $R_6$ or $R_7$ and $R_1$ may in combination form a 5- or 6-membered, saturated or unsaturated ring; Ψ of Formula F comprises a biologically compatible counter ion; and d is a number of Ψ sufficient to render overall charge of the compound neutral.

In some embodiments, the compound substantially lacks the ability to cross an intact cell membrane.

In another aspect, provided herein is a compound having the formula:

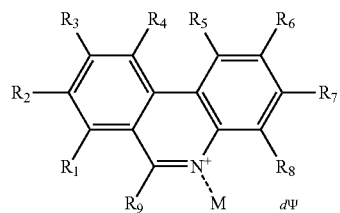

wherein $R_1$, $R_3$, $R_4$, $R_5$, $R_6$ and $R_8$ are independently H or F; wherein at least one of $R_2$ and $R_7$ is $N_3$ and any remaining $R_2$ and $R_7$ is $NH_2$; $R_9$ is phenyl substituted with at least one sulfonate group (—$SO_3$); M is a substituent having a molecular mass from about 60 to about 5000 Da; wherein M comprises at least one of the moieties selected from the group consisting of a poly(ethylene glycol), poly(propylene glycol), a poly(ethylene glycol and propylene glycol) copolymer, a polyhydroxy moiety, a negatively charged group, a positively charged group, a detectable label, and a functional group capable of forming a covalent linkage with a detectable label; Ψ comprises a biologically compatible counter ion; and d is a number of Ψ sufficient to render overall charge of the compound neutral.

In another aspect, provided herein is a compound of Table 1.

In one aspect, provided herein is a method of selectively labeling a non-viable organism or non-viable cell. In some embodiments, the method comprises contacting a compound with a sample comprising viable and non-viable organisms or cells to effect formation of a complex comprising the compound and a nucleic acid of the non-viable organism or non-viable cell, thereby selectively labeling the non-viable organism or non-viable cell in the sample; wherein the compound has the formula:

$(A)_a$-$(M)_b$     Formula A wherein, A is a nucleic acid modifying moiety (NAMM) comprising an activatable group capable of crosslinking with or cleaving a target nucleic acid;

a is 1 or 2;

b is 1 or 2; and

M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the non-viable organism is a dead bacterial cell or a non-viable virus. In some embodiments, the sample is an environmental sample or a sample from a subject. In some embodiments, the nucleic acid modifying moiety (NAMM) is capable of (1) binding to a nucleic acid and (2) crosslinking or cleaving said nucleic acid upon said binding. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$$(A)_a\text{-}(M)_b \qquad \text{Formula A'}$$

wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In some embodiments, the method further comprises activating an activatable group of the compound of Formula A to effect (i) conjugation between the compound and a nucleic acid in the sample to form a conjugate, or (ii) cleavage of nucleic acids in the sample. In some embodiments, the method further comprises amplifying nucleic acids present in said sample (e.g. nucleic acids that are not conjugated with the compound), to produce a detectable signal (e.g. within about 24 hours after obtaining the sample), wherein the signal is indicative of the presence of nucleic acids from a viable organism or cell. In some embodiments, the method further comprises subjecting the amplified nucleic acids to a sequencing reaction or to microarray hybridization.

In some embodiments, after activating the activatable group, the method further comprises (i) labeling both viable and non-viable organisms or cells with a common label; (ii) assaying for a first signal from the compound and a second signal from the common label; and (iii) identifying a test organism or test cell as non-viable if the test organism or cell is associated with both the first and second signals, or viable if the test organism or cell is associated with the second signal and substantially not associated with the first signal.

In one aspect, provided herein is a method of selectively labeling dead bacterial cells in a sample. In some embodiments, the method comprises contacting the sample with a compound that selectively modifies a nucleic acid of dead bacterial cells, thereby selectively labeling the dead bacterial cells in the sample; wherein the compound is characterized in that it selectively labels non-viable bacteria selected from the group consisting of *Staphylococcus aureus* collected by swabbing a surface, *Mycobacterium avium* subspecies *paratuberculosis* (MAP), and *Salmonella* serovar *Enteritidis*, in a control sample comprising the bacteria. In some embodiments, the compound has the formula:

$$(A)_a\text{-}(M)_b \qquad \text{Formula A}$$

wherein, A is a nucleic acid modifying moiety (NAMM) comprising an activatable group capable of crosslinking with or cleaving a target nucleic acid;
a is 1 or 2;
b is 1 or 2; and
M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the sample is an environmental sample or a sample from a subject. In some embodiments, the nucleic acid modifying moiety (NAMM) is capable of (1) binding to a nucleic acid and (2) crosslinking or cleaving said nucleic acid upon said binding. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$$(A)_a\text{-}(M)_b \qquad \text{Formula A'}$$

wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In some embodiments, the method further comprises activating an activatable group of the compound to effect (i) conjugation between the compound and nucleic acids in the sample to form conjugates, or (ii) cleavage of nucleic acids in the sample. In some embodiments, the method further comprises amplifying nucleic acids present in said sample to produce a detectable signal, wherein the signal is indicative of the presence of nucleic acids from a viable bacterial cell.

In some embodiments, after activating the activatable group, the method further comprises (i) labeling both viable and non-viable organisms or cells with a common label; (ii) assaying for a first signal from the compound and a second signal from the common label; and (iii) identifying a test organism or test cell as non-viable if the test organism or cell is associated with both the first and second signals, or viable if the test organism or cell is associated with the second signal and substantially not associated with the first signal.

In some embodiments, provided herein is a method of detecting viable microorganisms in a sample. In some embodiments, the method comprises: (a) contacting a compound with the sample, thereby forming a mixture; (b) activating an activatable group of the compound to effect (i) conjugation between the compound and nucleic acids in the mixture to form conjugates, or (ii) cleavage of nucleic acids in the mixture; and (c) detecting presence of viable microorganisms by: (i) amplifying nucleic acids present in said sample to produce a detectable signal, wherein the signal is indicative of the presence of nucleic acids from a viable microorganism; or (ii) (A) labeling both viable and non-viable microorganisms with a common label; (B) assaying for a first signal from the compound and a second signal from the common label; and (C) identifying a test microorganism as non-viable if the test microorganism is associated with both the first and second signals, or viable if the test microorganism is associated with the second signal and substantially not associated with the first signal; wherein the compound has a formula:

$$(A)_a\text{-}(M)_b \quad \quad \text{Formula A}$$

wherein, A is a nucleic acid modifying moiety (NAMM) comprising an activatable group capable of crosslinking with or cleaving a target nucleic acid;

a is 1 or 2;

b is 1 or 2; and

M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the viable microorganism is a viable bacterial cell or an infectious virus. In some embodiments, the sample is an environmental sample or a sample from a subject. In some embodiments, the nucleic acid modifying moiety (NAMM) is capable of (1) binding to a nucleic acid and (2) crosslinking or cleaving said nucleic acid upon said binding. In some embodiments, the amplifying comprises selectively amplifying a nucleic acid from the viable microorganism to produce a detectable amplification product. In some embodiments, the method further comprises subjecting amplified nucleic acids to a sequencing reaction or to microarray hybridization. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$$(A)_a\text{-}(M)_b \quad \quad \text{Formula A'}$$

wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In one aspect, provided herein is a method of detecting viable bacteria in a sample. In one embodiment, the method comprises: (a) contacting the sample with a compound that selectively modifies a nucleic acid of dead bacterial cells, thereby forming a mixture; wherein the compound is characterized in that it selectively labels non-viable bacteria selected from the group consisting of *Staphylococcus aureus* collected by swabbing a surface, *Mycobacterium avium* subspecies *paratuberculosis* (MAP), and *Salmonella* serovar *Enteritidis*, in a control sample comprising the bacteria; (b) activating an activatable group of the compound to effect (i) conjugation between the compound and nucleic acids in the mixture to form conjugates, or (ii) cleavage of nucleic acids in the mixture; and (c) detecting presence of viable bacteria by: (i) amplifying nucleic acids present in said sample to produce a detectable signal, wherein the signal is indicative of the presence of nucleic acids from a viable microorganism; or (ii) (A) labeling both viable and non-viable bacterial cells with a common label; (B) assaying for a first signal from the compound and a second signal from the common label; and (C) identifying a test microorganism as non-viable if the test microorganism is associated with both the first and second signals, or viable if the test microorganism is associated with the second signal and substantially not associated with the first signal. In some embodiments, the compound has the formula:

$$(A)_a\text{-}(M)_b \quad \quad \text{Formula A}$$

wherein, A is a nucleic acid modifying moiety (NAMM) comprising an activatable group capable of crosslinking with or cleaving a target nucleic acid;

a is 1 or 2;

b is 1 or 2; and

M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the sample is an environmental sample or a sample from a subject. In some embodiments, the nucleic acid modifying moiety (NAMM) is capable of (1) binding to a nucleic acid and (2) crosslinking or cleaving said nucleic acid upon said binding. In some embodiments, the amplifying comprises selectively amplifying a nucleic acid from the viable microorganism to produce a detectable amplification product. In some embodiments, the method further comprises subjecting amplified nucleic acids to a sequencing reaction or to microarray hybridization. In some embodiments, the amplifying comprises selectively amplifying a nucleic acid from the viable bacterial cell to produce a detectable amplification product. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$$(A)_a\text{-}(M)_b \quad \quad \text{Formula A'}$$

wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In one aspect, provided herein is a method of labeling a target polynucleotide. In some embodiments, the method comprises: (a) contacting a sample comprising a target polynucleotide with a nucleic acid probe comprising a polynucleotide joined to a compound; and (b) detecting a detectable signal indicative of hybridization between the target polynucleotide and the nucleic acid probe; wherein the compound has the formula:

$(A)_a\text{-}(M)_b$  Formula A wherein, A is a nucleic acid modifying moiety (NAMM) comprising an activatable group capable of crosslinking with or cleaving a target nucleic acid;
a is 1 or 2;
b is 1 or 2; and
M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the detection identifies the location of the target polynucleotide relative to a second component of the sample. In some embodiments, the second component is a cell, an organelle, a chromosome, a protein, an enzyme, or a nucleic acid. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$(A)_a\text{-}(M)_b$  Formula A' wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In one aspect, provided herein is a method of labeling a nucleic acid probe. In some embodiments, the method comprises contacting a nucleic acid probe with a compound to form a mixture, and exposing the mixture to a linking agent to effect conjugation between the nucleic acid probe and the compound; wherein the compound has the formula:

$(A)_a\text{-}(M)_b$  Formula A wherein, A is a nucleic acid modifying moiety (NAMM) comprising an activatable group capable of crosslinking with or cleaving a target nucleic acid;
a is 1 or 2;
b is 1 or 2; and
M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the linking agent is visible light. In some embodiments, the method further comprises separating labeled nucleic acid probes from one or both of unconjugated compound and unconjugated nucleic acid probes in the mixture. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$(A)_a\text{-}(M)_b$  Formula A' wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In one aspect, provided herein are nucleic acid probes. In some embodiments, a nucleic acid probe comprises a polynucleotide joined to a compound, wherein the compound comprises (i) a nucleic acid binding moiety, (ii) a detectable label, and (iii) an activatable group that covalently bonds to a target polynucleotide when exposed to a linking agent. In some embodiments, the linking agent is visible light. In some embodiments, the compound has the formula:

$(A)_a\text{-}(M)_b$  Formula A wherein, A is a nucleic acid modifying moiety (NAMM) comprising an activatable group capable of crosslinking with or cleaving a target nucleic acid;
a is 1 or 2;
b is 1 or 2; and
M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, the detectable label is a fluorescent dye label, biotin, digoxigenin, or a hapten. In some embodiments, M comprises a functional group capable of forming a covalent linkage with a detectable label, and further wherein M is selected from the group consisting of alkyne, azido, aldehyde, hydrazine, and hydroxylamine. In some embodiments, the NAMM is a nucleic acid binding dye. In some embodiments, the compound has the formula:

$$(A)_a\text{-}(M)_b \qquad \text{Formula A'}$$

wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label.

In one aspect, provided herein are kits comprising one or more compositions described herein, such as one or more compounds and/or one or more nucleic acid probes as described with respect to any aspect of the disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
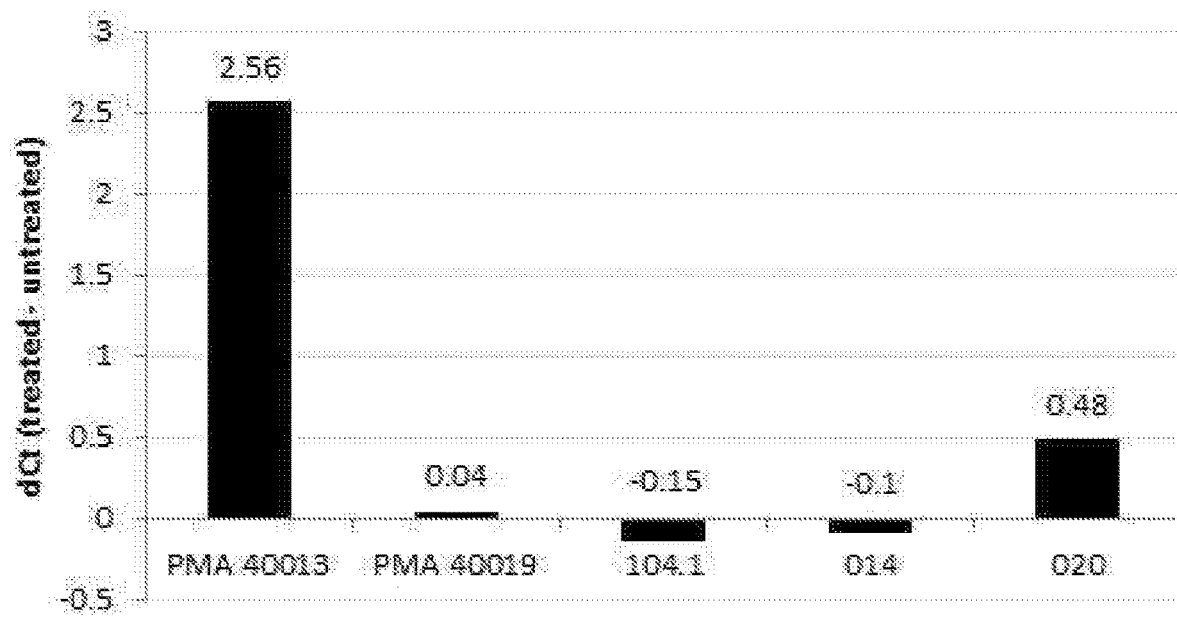
FIG. 1 is a graph comparing modification of DNA in viable cells by the indicated compounds.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

As used in the specification and claims, the singular form "a", "an" and "the" include plural references unless the context clearly dictates otherwise. For example, the term "a cell" includes a plurality of cells, including mixtures thereof.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (i), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction.

In general, a "nucleotide probe," "probe," or "tag oligonucleotide" refers to a polynucleotide used for detecting or identifying its corresponding target polynucleotide in a hybridization reaction by hybridization with a corresponding target sequence. Thus, a nucleotide probe is hybridizable to one or more target polynucleotides. Probe oligonucleotides can be perfectly complementary to one or more target polynucleotides in a sample, or contain one or more nucleotides that are not complemented by a corresponding nucleotide in the one or more target polynucleotides in a sample.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

As used herein, when any variable occurs more than one time in a chemical formula, its definition on each occurrence is independent of its definition at every other occurrence.

As used herein, a dash ("—") that is not between two letters or symbols is used to indicate a point of attachment for a substituent. For example, —CONH2 is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "azido" refers to the group —$N_3$.

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "halo" refers to fluoro, chloro, bromo, and iodo, and the term "halogen" includes fluorine, chlorine, bromine, and iodine.

As used herein, "heteroaryl" refers to:
5- to 7-membered aromatic, monocyclic rings containing one or more, for example, from 1 to 4, or in certain embodiments, from 1 to 3, heteroatoms chosen from N, O, and S, with the remaining ring atoms being carbon;
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and
tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein.

Substituted heteroaryl also includes ring systems substituted with one or more oxide (—$O^-$) substituents, such as pyridinyl N-oxides.

In one aspect, the disclosure provides a compound having the formula:

$$(A)_a\text{-}(M)_b \qquad \text{Formula A}$$

wherein, A is a nucleic acid modifying moiety (NAMM) comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, M comprises a detectable label.

In some embodiments, a is 1 or 2. In some embodiments, a is 1. In some embodiments, a is 2.

In some embodiments, b is 1 or 2. In some embodiments, b is 1. In some embodiments, b is 2.

In some embodiments, a is 1 and b is 1. In some embodiments, a is 1 and b is 2. In some embodiments, a is 2 and b is 1. In some embodiments, a is 2 and b is 2.

The term "nucleic acid modifying moiety (NAMM)" refers to a chemical substituent capable of modifying a nucleic acid covalently or non-covalently. A NAMM group can comprise a nucleic acid binding moiety and/or an activatable group. In some embodiments, the nucleic acid binding moiety and the activatable group are the same chemical moiety. In such cases, this chemical moiety is a NAMM. For example, the ruthenium complexes and platinum complexes described herein can function as both a nucleic acid binding moiety and an activatable group. In some other embodiments, the nucleic acid binding moiety and the activatable group are distinct chemical moieties which are selected to function together as a NAMM. For example, a nucleic acid binding dye covalently attached to photoaffinity label as described herein is a NAMM. In cases wherein the nucleic acid binding moiety and the activatable group are distinct, the two moieties can affect each other's functionality depending on the location and type of chemical connection that is selected to join them. In general, it is preferable to select a relatively small activatable group, and to attach it to the nucleic acid binding moiety at a position such that the nucleic acid binding affinity of the resulting NAMM is either enhanced or not lowered significantly relative to the binding affinity of the nucleic acid binding moiety lacking the activatable group.

The term "nucleic acid binding moiety" (NABM) refers to a substituent that is capable of binding to a nucleic acid molecule. Such binding can be effected via covalent or non-covalent interaction (e.g., via hydrogen bonding, Van der waals interaction). The NABM may bind to or intercalated in one or more of single- or double-stranded DNA, single- or double-stranded RNA, or other polynucleotides, under desired conditions. In some embodiments, the NABM binds double-stranded DNA. What constitutes "desired conditions" will vary depending upon application, but in general refers to reaction conditions such as temperature, pH, solvent, ionic strength, the presence or absence of chaotropic agents, reactant concentrations, etc. to be encountered in the eventual intended application of the compound. A variety of NABMs are available, non-limiting examples of which include nucleic acid binding dyes, oligonucleotides (optionally including modified nucleotides, modified backbone chemistries, and/or nucleotide analogs), minor groove binders, major groove binders, DNA intercalators, DNA-binding proteins (e.g. transcription factors, histones), and polycations. Additional examples can be found in WO2002034295A1, WO2012068392A2, WO2001074898A2, US20070255041, and U.S. Pat. No. 8,198,040.

The activatable group of A as denoted in Formula A or Formula A' can be selected to be any chemically reactive or photolytically reactive (i.e. photoreactive) group, the inclusion of which does not significantly adversely affect the nucleic acid binding of the NAMM relative to the nucleic acid binding moiety and which is capable of undergoing crosslinking with a target nucleic acid or of cleaving a target nucleic acid under physiological conditions. In some embodiments, physiological conditions comprise a physiological medium (i.e. aqueous medium) at a temperature ranging from about 4° C. to about 90° C. or from about room temperature (e.g. 20° C.-25° C.) to about 40° C.

In some embodiments, the activatable group is selected such that a dissociation constant ($K_d$) of a NAMM lacking the activatable group and a target nucleic acid relative to a $K_d$ of a NAMM comprising the activatable group and the target nucleic acid are substantially similar. In some embodiments, the activatable group is selected such that a dissociation constant ($K_d$) of a NAMM lacking the activatable group and a target nucleic acid relative to a $K_d$ of a NAMM comprising the activatable group and the target nucleic acid are within a factor of 0.01, 0.1, 1.1, 1.2, 1.3, 1.4, 1.5, 2.0, 3.0, 4.0, 5.0, 10.0, 100.0, 1000.0, or 10000.0. The $K_d$'s may be within a factor of about 0.5 to about 5.

The activatable group can be selected from the group consisting of a furan, an enediyne, a metal complex (i.e. ruthenium complex or a platinum complex), and a photoaffinity label (i.e. azide, benzophenone, or diazirine).

In some embodiments, the activatable group is an enediyne. Some non-limiting examples of NAMM groups comprising an enediyne include natural products such as dynemicin A and neocarzinostatin (example anti-tumor and antibiotic compounds; see e.g. Sugiura, Y.; Shiraki, T.; Konishi, M.; Oki, T. DNA Intercalation and Cleavage of an Antitumor Antibiotic Dynemicin that Contains Anthracycline and Enediyne Cores. *Proc. Natl. Acad. Sci. U.S.A.* 1990, 87, 3831-3835; Lee, S. H.; Goldberg, I. H. Sequence-Specific, Strand-Selective, and Directional Binding of Neocarzinostatin Chromophore to Oligodeoxyribonucleotides. *Biochemistry* 1989, 28, 1019-1026). Such compounds possess an enediyne moiety that can cleave DNA via cyclization to form a free radical. In some embodiments of the compounds described herein, the compound comprises a NAMM comprising an activatable group, wherein the activatable group is an enediyne moiety capable of cleaving a target nucleic acid. In some embodiments, the enediyne moiety selectively cyclizes in the presence of DNA or a target nucleic acid.

In other embodiments, the activatable group is a metal complex. A metal complex capable of cleaving nucleic acids can utilize a variety of different chemical mechanisms (see e.g. H. H., Thorp *J. Inorg. and Organom. Ploym.* 1993, 3(1), 41). For example, some ruthenium complexes can act as DNA scissors via either photolysis-mediated reaction or chemical-mediated reactions. In some embodiments, the activatable group is a ruthenium complex capable of cleaving DNA (see e.g. Y.-J. Liu et. al. *Tran. Met. Chem.* 2007, 32, 332-337; and X.-W. Liu, et. al. *Inorg. Chim. Acta.* 2011, 379(1), 1-6). In some embodiments, the activatable group is a platinum complex capable of cleaving DNA (see e.g. J. D, Roberts, et al. *Nuc. Acid Res.* 1989, 17(23), 7919); and references therein). Such complexes can form coordinative complexes with guanine bases, and further exemplified by platinum-based anticancer drugs.

In some embodiments, the activatable group is a furan. In some embodiments, a furan moiety can label DNA (see e.g. M. Beeck and A. Madder *J. Am. Chem. Soc.* 2011, 133(4). 796-807). For example, a furan group can label target nucleic acid by forming a covalent bond to a cytidine of the target nucleic acid under oxidative conditions.

In some embodiments, the activatable group is a photoaffinity label. In general, a photoaffinity label is a photoreactive group that is chemically unreactive until it is photolyzed (treated with a light source capable of chemically altering the group) to form a reactive intermediate that can undergo a rapid bond-forming reaction. Some non-limiting examples of suitable photoaffinity labels include an aryl azide (see e.g. Platz, M. S. *Acc. Chem. Res.* 1995, 28, 487), a benzophenone (see e.g. Fujii, T.; Manabe, Y.; Sugimoto, T.; Ueda, M. *Tetrahedron* 2005, 61, 7874), and a diazirine (see e.g. Y. Mural *J. Org. Chem.* 2012, 77, 8581-8587; L. Dubinsky et al. *Bioorg. Med. Chem.* 2012, 20, 554-570).

In some embodiments, the reactive moiety is a photoreactive azido group ($-N_3$). The azido group has the advantage of being relatively small in size and can be easily introduced during synthesis. In some embodiments, the azido group is attached to an aromatic ring. Upon treatment with a light source of suitable frequency and flux, the azide moiety can undergo a photolysis reaction, wherein the azide is converted to a highly reactive nitrene. The reactive nitrene can undergo a cycloaddition reaction with a carbon-carbon double bond to form an aziridine, or the nitrene can undergo an insertion reaction with a carbon-hydrogen bond to form a substituted amine linkage. In some embodiments, the compound of Formula A comprising an azide group is bound to a target nucleic acid, wherein treatment with a suitable light source can photolyze the azide group to form a nitrene intermediate, wherein the nitrene intermediate can chemically react with the target nucleic acid to form a covalent attachment between the compound of Formula A and the target nucleic acid.

In some embodiments of a compound of Formula A, the compound has the structure of Formula A':

   Formula A' wherein, A is a nucleic acid binding dye comprising an activatable group capable of crosslinking with or cleaving a target nucleic acid; a is 1 or 2; b is 1 or 2; and M is a substituent having a molecular mass from about 150 to about 5000 Da; wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, a positively charged group, a detectable label, and a functional group capable of forming a covalent linkage with a detectable label. In some embodiments, M comprises a detectable label.

In some embodiments, the nucleic acid binding dye is selected from the group consisting of phenanthridium, cyanine, acridine, acridinium, and Hoechst dyes. Various chemistries for constructing nucleic acid binding molecules, such as nucleic acid binding dyes, are available (see e.g. Deligeorgiv, T., et al. *Recent patents on Materials Sciences* 2009, 2, 1-26). For example, DNA or RNA binding dyes or molecules can be based on the chemical structures of asymmetric cyanine dyes (see e.g. U.S. Pat. Nos. 5,321,130; 5,436,134; and 7,582,429; US patent application Nos. 2010/0233710; 2010/0330579), phenanthridium dyes (see e.g. Prunkl, et al. *Chem. Eur. J.* 2010, 16, 3392; Tam, V., et al. *Chem. Comm.* 2006, 2684-2686;), acridine or acridinium dyes, Hoechst dyes (see e.g. Rastogi, K., et al. *J. Med. Chem.* 2002, 45, 4485-4495), poly(imidazole and/or pyrrole carboxamides) (see e.g. WO1997030975 A3) and pyrylium dyes (see e.g. U.S. Pat. No. 6,384,637).

In some embodiments, A is an azido-substituted nucleic acid binding dye. In some embodiments, the reactive group is an azido group, wherein the azido group is directly attached to an aromatic ring that is part of the chromophoric moiety of a nucleic acid binding dye. The chromophoric moiety of a nucleic acid binding dye as described herein refers to the aromatic ring and any associated vinyl bond system of the dye, which determines the absorption and emission wavelengths (i.e., colors) of the dye. The wavelengths and also the fluorescence quantum yield of such chromophoric moiety can be detectably affected by the number and nature of substituents attached to it. As a result, a nucleic acid binding dye comprising an azido group attached to its chromophoric moiety can have one or more spectral properties differ from that of the parent dye without the azido group. For example, the azido group can be a fluorescence quenching group.

In some embodiments, compounds of Formula A comprising an azido attached to the chromophoric moiety are only weakly fluorescent or completely nonfluorescent. Such cases can result in a fluorescence signal differentiation between the NAMM before photolysis and after photolysis. Upon crosslinking of the dye with a target nucleic acid, the azido group is converted to an alkylamino group, which can result in a detectable fluorescence signal of the dye. Hence, in some cases, a fluorescence increase upon photolysis of a sample comprising a target nucleic acid and a compound of Formula A comprising an azido substituted NAMM may be indicative of successful crosslinking between the compound and the nucleic acid. This fluorescence response is not required for the purpose of inactivating the capacity of a target nucleic acid to serve as template in nucleic acid amplification as described in some embodiments of methods described herein. However, this fluorescence response may be utilized for the purpose of marking the physical location of a target nucleic acid or identifying dead cells, or for the purpose of making a nucleic acid probe, such as a FISH probe, as further described herein.

In some embodiments, M is a substituent having a molecular mass less than 8000, 7000, 6000, 5000, 4000, 3000, 2000, 1000, or 500 Da. In some embodiments, M is a substituent having a molecular mass of at least 80, 90, 100, 110, 120, 130, 140, 150, 160, 170, 180, 190, 200, 250, 300, 350, 400, 500, 600, 700, 800, 900, or 1000 Da. In some embodiments, M is a substituent having a molecular mass between 100-6000 Da, 150-5000 Da, 200-4000 Da, or 250-3000 Da. In some embodiments, M is a substituent having a molecular mass from 200-1500 Da In some embodiments, M comprises a poly(ethylene glycol) of molecular mass of at least 80, 90, 100, 110, 120, 130, 140, 150, 160, 170, 180, 190, 200, 250, 300, 350, 400, 500, 600, 700, 800, 900, or 1000 Da. In some embodiments, M comprises a poly(ethylene glycol) of molecular mass of less than 3000, 2000, 1000, 900, 800, 700, 600, 500, 400, 300, 250, 200, 150, or 130 Da. In some embodiments, M comprises a poly(ethylene glycol) of molecular mass between 100-2000 Da, 120-1000 Da, 150-800 Da, or 200-600 Da.

In some embodiments, M comprises a poly(propylene glycol) of molecular mass of at least 80, 90, 100, 110, 120, 130, 140, 150, 160, 170, 180, 190, 200, 250, 300, 350, 400, 500, 600, 700, 800, 900, or 1000 Da. In some embodiments, M comprises a poly(propylene glycol) of molecular mass of less than 3000, 2000, 1000, 900, 800, 700, 600, 500, 400, 300, 250, 200, 150, or 130 Da. In some embodiments, M comprises a poly(propylene glycol) of molecular mass between 100-2000 Da, 120-1000 Da, 150-800 Da, or 200-600 Da.

In some embodiments, M comprises a poly(ethylene glycol and propylene glycol) copolymer of molecular mass of at least 80, 90, 100, 110, 120, 130, 140, 150, 160, 170, 180, 190, 200, 250, 300, 350, 400, 500, 600, 700, 800, 900, or 1000 Da. In some embodiments, M comprises a poly (ethylene glycol and propylene glycol) copolymer of molecular mass of less than 3000, 2000, 1000, 900, 800, 700, 600, 500, 400, 300, 250, 200, 150, or 130 Da. In some embodiments, M comprises a poly(ethylene glycol and propylene glycol) copolymer of molecular mass between 100-2000 Da, 120-1000 Da, 150-800 Da, or 200-600 Da.

In some embodiments, M comprises a polyhydroxy moiety. Some non-limiting examples of a polyhydroxy moiety are a sugar, oligosaccharide, polysaccharide, dextrin, or cyclodextrin. In some embodiments, M comprises a polyhydroxy moiety of molecular mass of at least 80, 90, 100, 110, 120, 130, 140, 150, 160, 170, 180, 190, 200, 250, 300, 350, 400, 500, 600, 700, 800, 900, or 1000 Da. In some embodiments, M comprises polyhydroxy moiety of molecular mass of less than 3000, 2000, 1000, 900, 800, 700, 600, 500, 400, 300, 250, 200, 150, or 130 Da. In some embodiments, M comprises a polyhydroxy moiety of molecular mass between 100-2000 Da, 120-1000 Da, 150-800 Da, or 200-600 Da.

In some embodiments, M comprises one or more charges. In some embodiments, M comprises one or more negatively charged group, one or more positively charged groups, or a combination thereof. In some embodiments, M comprises one or more negatively charged groups. In some embodiments, M comprises one or more negatively charged group and one or more positively charged groups. In some embodiments, M comprises 1 negatively charged group. In some embodiments, M comprises 2 negatively charged groups. In some embodiments, M comprises 1 or 2 negatively charged groups. In some embodiments, M comprises 3 negatively charged groups. In some embodiments, M comprises one or more positively charged groups. In some embodiments, M comprises one positively charged group. In some embodiments, M comprises 2 positively charged groups. In some embodiments, M comprises 3 positively charged groups.

In some embodiments, the compound of Formula A substantially lacks the ability to cross an intact cell membrane.

In some embodiments, M comprises a detectable label. A detectable label is a chemical moiety that can be detected directly through spectroscopy or indirectly through generation of a signal, generation of immune response, chemical modification or reactivity, or binding to a sensor or receptor. In some embodiments, the detectable label is a fluorescent dye label. In other embodiments, the detectable label is biotin, digoxigenin, or a hapten.

In some embodiments, M comprises a functional group capable of forming a covalent linkage with a detectable label. The functional group as described herein can be a chemical moiety that is chemically compatible with the activatable group of the compound and is capable of forming a covalent linkage with a detectable label. Non-limiting examples of a suitable functional group can include a primary or secondary amine, a CLICK chemistry reaction partner (e.g., an azido or alkyne), an aldehyde, a hydrazine or an aminooxy, for example. In some embodiments, the detectable label comprises a reactive group that is compatible with the functional group. The reactive group and the functional group are typically an electrophile and a nucleophile, respectively, that can form a covalent bond. According to one alternative, the reactive group is a photoactivatable group capable of reacting with a hydrocarbon molecule upon ultraviolet photoactivation or photolysis. According to another alternative, the reactive group is a dienophile capable of reacting with a conjugated diene via a Diels-Alder reaction. According to yet another alternative, the reactive group is a 1,3-diene capable of reacting with a dienophile. Still other reactive group/functional group pairs may be selected based on Staudinger chemistry or the reaction between an azido group and a terminal alkyne (the so-called Click chemistry). Non-limiting examples of useful reactive groups, functional groups, and corresponding linkages are listed in Table 2. A nucleic acid probe modified with the compound can be subsequently reacted with detectable label comprising a reactive group, resulting in a probe modified with a detectable label of choice.

TABLE 2

Examples of Reactive Groups, Functional Groups, and Covalent Linkages

| Electrophilic Group | Nucleophilic Group | Resulting Covalent Linkage |
| --- | --- | --- |
| activated esters * | amines/anilines | Carboxamides |
| acrylamides | Thiols | Thioethers |
| acyl azides** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anilines | Imines |
| aldehydes or ketones | Hydrazines | Hydrazones |
| aldehydes or ketones | Hydroxylamines | Oximes |
| alkyl halides | amines/anilines | alkyl amines |
| alkyl halides | carboxylic acids | Esters |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |
| anhydrides | amines/anilines | Carboxamides |

TABLE 2-continued

Examples of Reactive Groups, Functional Groups, and Covalent Linkages

| Electrophilic Group | Nucleophilic Group | Resulting Covalent Linkage |
| --- | --- | --- |
| aryl halides | Thiols | Thiophenols |
| aryl halides | Amines | aryl amines |
| aziridines | Thiols | Thioethers |
| boronates | Glycols | boronate esters |
| carboxylic acids | amines/anilines | Carboxamides |
| carboxylic acids | Alcohols | Esters |
| carboxylic acids | Hydrazines | Hydrazides |
| carbodiimides | carboxylic acids | N-acylureas or anhydrides |
| diazoalkanes | carboxylic acids | Esters |
| epoxides | Thiols | Thioethers |
| haloacetamides | Thiols | Thioethers |
| halotriazines | amines/anilines | Aminotrizaines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | carboxylic acids | Esters |
| sulfonate esters | Alcohols | Ethers |
| sulfonyl halides | amines/anilines | Sulfonamides |
| sulfonyl halides | phenols/alcohols | sulfonate esters |

* Activated esters, as understood in the art, generally have the formula —COΩ, where Ω is a good leaving group, such as succinimidyloxy (—OC$_4$H$_4$O$_2$), sulfosuccinimidyloxy (—OC$_4$H$_3$O$_2$—SO$_3$H), or -1-oxybenzotriazolyl (—OC$_6$H$_4$N$_3$), for example; or an aryloxy group or aryloxy substituted one or more times by electron-withdrawing substituent(s), such as nitro, fluoro, chloro, cyano, trifluoromethyl, or combinations thereof, for example, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are independently C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl.
**Acyl azides can also rearrange to isocyanates.

The reactive group may be one that will react with an amine, a thiol, or an aldehyde. The reactive group may be an amine-reactive group, such as a succinimidyl ester, for example, or a thiol-reactive group, such as a maleimide, a haloacetamide, or a methanethio-sulfonate (MTS), for example, or an aldehyde-reactive group, such as an amine, an aminooxy, or a hydrazide, for example.

The functional group may be one that will react with an amine, a thiol, or an aldehyde. The functional group may be an amine-reactive group, such as a succinimidyl ester, for example, or a thiol-reactive group, such as a maleimide, a haloacetamide, or a methanethio-sulfonate (MTS), for example, or an aldehyde-reactive group, such as an amine, an aminooxy, or a hydrazide, for example.

In some embodiments, M comprises a poly(ethylene glycol) and a positively charged group.

In some embodiments, M comprises a poly(ethylene glycol) and one or two negatively charged groups.

In some embodiments of the compound of Formula A or Formula A', the compound has the structure of Formula B:

A-L'-(CH$_2$CH$_2$O)$_n$-L'-B    Formula B wherein, A is a nucleic acid modifying moiety (NAMM) comprising an activatable group capable of crosslinking with or cleaving a target nucleic acid; each L' is independently a single bond or a linker comprising 1-15 atoms selected from the group consisting of C, N and O; n is an integer from 2-40 inclusive; and B is a moiety comprising at least one of the moieties selected from the group consisting of a negatively charged group, a positively charged group, and a detectable label. In some embodiments, A is a nucleic acid binding dye comprising an activatable group capable of crosslinking with or cleaving a target nucleic acid;

In some embodiments, each L' is a single bond. In other embodiments, at least one L' is a linker comprising 4-10 atoms selected from the group consisting of C, N and O; and n is an integer from 2-24 inclusive. In some embodiments, at least one L' is a single bond. In some embodiments, each L' is independently a bond, —($C_1$-$C_{12}$ alkyl)- or —($C_1$-$C_{12}$ alkyl)-C(O)NH—. In some embodiments, one L' is a bond, and the other L' is a linker comprising 4-10 atoms selected from the group consisting of C, N and O; and n is an integer from 2-24 inclusive.

In some embodiments of a compound described herein, the compound can further comprise dΨ; wherein Ψ comprises a biologically compatible counter ion; and d is a number of Ψ sufficient to render overall charge of the compound neutral. Ψ may be a positively charged or negatively charged, biologically compatible counter ion. Ψ may serve to balance the overall charge of the compound described herein, such that the compound is neutral in overall charge. Merely by way of example, a positively charged Ψ may be $H^+$, $Na^+$, $K^+$, $NH_4^+$, N,N,N-triethylammonium, N,N-diisopropylethylammonium, or the like. Merely by way of example, a negatively charged Ψ may be a halide, a sulfate, a phosphate, a perchlorate, a hexafluorophosphate, a tetrafluoroborate, or the like. D is a number of Ψ that serves to balance the charge of the compound.

In some embodiments, B is selected from the group consisting of an amino acid, dipeptide, cysteic acid, cysteine, $C_1$-$C_{12}$ alkyl comprising an amide, $C_1$-$C_{12}$ alkyl substituted with a carboxylic acid, and $C_1$-$C_{12}$ alkyl substituted with a trialkylammonium salt. In some embodiments, B comprises a negatively charged group selected from the group consisting of —$SO_3^-$, —$CO_2^-$, and —$PO_3^{2-}$. In other embodiments, B comprises a positively charged group that is a trialkylammonium group.

In some embodiments of the compound of Formula A, the nucleic acid modifying moiety NAMM has the structure of Formula C or Formula D:

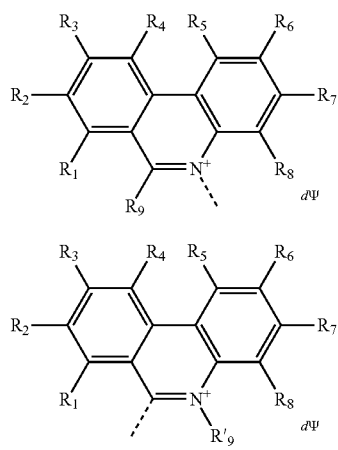

Formula C

Formula D wherein the dashed line indicates the attachment site for the substituent M;

$R_1$, $R_2$, $R_3$, $R_4$, $R_5$, $R_6$, $R_7$ and $R_8$ are independently selected from the group consisting of H, F, Cl, Br, $C_1$-$C_2$ alkyl, $C_1$-$C_2$ alkoxy, amino and $C_1$-$C_2$ alkyl or dialkylamino, amidino, guanidino, and azide;

$R_9$ is a substituted or unsubstituted alkyl, substituted or unsubstituted aryl or substituted or unsubstituted heteroaryl; $R'_9$ is a substituted or unsubstituted alkyl; and wherein at least one of $R_1$, $R_2$, $R_3$, $R_4$, $R_5$, $R_6$, $R_7$ or $R_8$ is azide (—$N_3$); Ψ comprises a biologically compatible counter ion; and d is a number of 'I' sufficient to render overall charge of the compound neutral.

In some embodiments of the compound of Formula A', the compound has the structure:

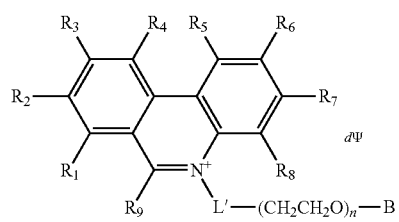

wherein $R_1$, $R_3$, $R_4$, $R_5$, $R_6$ and $R_8$ are independently H or F; wherein at least one of $R_2$ and $R_7$ is $N_3$ and any other remaining $R_2$ and $R_7$ is $NH_2$; $R_9$ is phenyl; L' is a single bond or a linker comprising 1-15 atoms selected from the group consisting of C, N and O; n is an integer from 2-40 inclusive; and B is a moiety comprising at least one of the moieties selected from the group consisting of a negatively charged group, a positively charged group, and a detectable label; Ψ comprises a biologically compatible counter ion; and d is a number of Ψ sufficient to render overall charge of the compound neutral.

In some embodiments of the compound of Formula A', the compound has the structure:

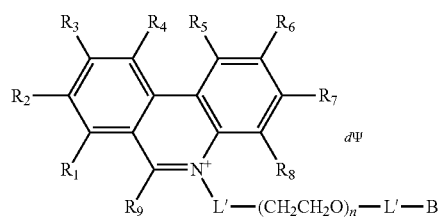

wherein $R_1$, $R_3$, $R_4$, $R_5$, $R_6$ and $R_8$ are independently H or F; wherein at least one of $R_2$ and $R_7$ is $N_3$ and any other remaining $R_2$ and $R_7$ is $NH_2$; $R_9$ is phenyl; each L' is independently a single bond or a linker comprising 1-15 atoms selected from the group consisting of C, N and O; n is an integer from 2-40 inclusive; and B is a moiety comprising at least one of the moieties selected from the group consisting of a negatively charged group, a positively charged group, and a detectable label; Ψ comprises a biologically compatible counter ion; and d is a number of Ψ sufficient to render overall charge of the compound neutral.

In some embodiments of the compound of Formula A, the nucleic acid modifying moiety (NAMM) has the structure of Formula E:

(Formula E)

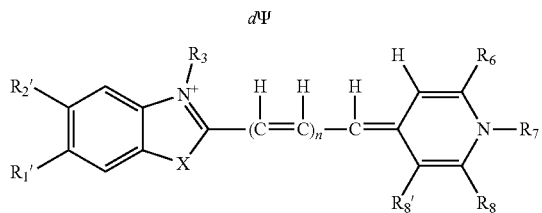

wherein $R_1'$ or $R_2'$ of Formula E is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; —C(=O)NH$R_{15}$ or $N_3$; or a substituent associated with minor groove binding; or represents where M attaches to the structure;

when $R_1'$ or $R_2'$ of Formula E comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl; when $R_1'$ or $R_2'$ of Formula E comprises $R_{11}$ and $R_{12}$, $R_{11}$ and $R_{12}$ may in combination form a 5- or 6-membered, saturated or unsaturated ring, which optionally comprises at least one hetero atom selected from N and O; $R_3$ of Formula E is $C_1$-$C_3$ alkyl; X of Formula E is selected from O and S; n of Formula E is selected from 0, 1, and 2; $R_6$ of Formula E is H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; —$N_3$; or a substituted or an unsubstituted aryl, optionally comprising 1 to 3 hetero atom(s), inclusive, selected from N, O, and S; or represents where L attaches to the structure;

$R_7$ of Formula E is H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from N, O, and S; or represents where M attaches to the structure;

$R_8$ and $R_8'$ of Formula E in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen;

each of $R_{16}$ and $R_{17}$ independently is H; alkyl having 1 carbon to 12 carbons, inclusive, optionally incorporating 1 to 2 nitrogen(s) or an aryl; or $R_{16}$ and $R_{17}$ may in combination form a 5- or 6-membered saturated or unsaturated ring, which optionally comprises at least one hetero atom selected from N and O; only one of $R_1'$, $R_2'$, $R_6$, and $R_7$ of Formula E represents where M attaches to the structure; at least one of $R_1'$, $R_2'$ and $R_6$, is —$N_3$; Ψ of Formula E comprises a biologically compatible counter ion; and d is a number of Ψ sufficient to render overall charge of the compound neutral.

In some embodiments of the compound of Formula A, the nucleic acid modifying moiety (NAMM) has the structure of Formula F:

(Formula F)

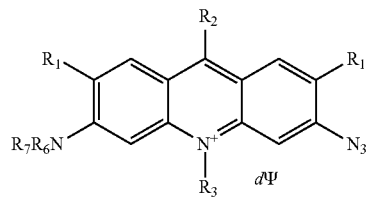

wherein each $R_1$ of Formula F is independently H or a C1-C2, inclusive, alkyl;
one of $R_2$ and $R_3$ of Formula F represents where M attaches to the structure;
when $R_2$ represents where M attaches to the structure, $R_3$ is H or —$CH_3$;
when $R_3$ represents where M attaches to the structure, $R_2$ is selected from H, —$CH_3$, —$NH_2$, —$NHCH_3$, —CN, and —C(=O)$NH_2$;
$R_6$ of Formula F is independently H or a C1-C2, inclusive, alkyl;
$R_7$ of Formula F is independently H or a C1-C2, inclusive, alkyl;
for a pair of $R_6$ or $R_7$ and adjacent $R_1$, independently, $R_6$ or $R_7$ and $R_1$ may in combination form a 5- or 6-membered, saturated or unsaturated ring; and
Ψ of Formula F comprises a biologically compatible counter ion; and d is a number of 'I' sufficient to render overall charge of the compound neutral.

Further provided herein, is a compound having the structure:

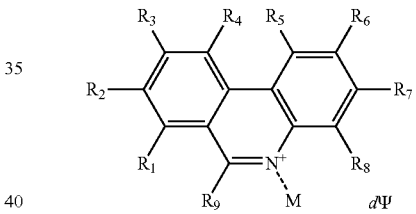

wherein $R_1$, $R_3$, $R_4$, $R_5$, $R_6$ and $R_8$ are independently H or F; wherein at least one of $R_2$ and $R_7$ is $N_3$ and any remaining $R_2$ and $R_7$ is $NH_2$; $R_9$ is phenyl substituted with at least one sulfonate group (—$SO_3^-$); M is a substituent having a molecular mass from about 60 to about 5000 Da; wherein M comprises at least one of the moieties selected from the group consisting of a poly(ethylene glycol), poly(propylene glycol), a poly(ethylene glycol and propylene glycol) copolymer, a polyhydroxy moiety, a negatively charged group, a positively charged group, a detectable label, and a functional group capable of forming a covalent linkage with a detectable label; Ψ comprises a biologically compatible counter ion; and d is a number of Ψ sufficient to render overall charge of the compound neutral.

Ψ may be a positively charged or negatively charged, biologically compatible counter ion. Ψ may serve to balance the overall charge of the compound described herein, such that the compound is neutral in overall charge. Merely by way of example, a positively charged Ψ may be $H^+$, $Na^+$, $K^+$, $NH_4^+$, N,N,N-triethylammonium, N,N-diisopropylethylammonium, or the like. Merely by way of example, a negatively charged Ψ may be a halide, a sulfate, a phosphate, a perchlorate, a hexafluorophosphate, a tetrafluoroborate, or the like. D is a number of Ψ that serves to balance the charge of the compound.

In another aspect, the disclosure provides compounds of Formula A, Formula A', Formula B, Formula C, Formula D, Formula E or Formula F in Table 1.

| Compound No. | Compound Structure | Molecular Mass of M Moiety |
|---|---|---|
| 4 | [structure: benzothiazole-quinoline cyanine dye with N₃ group, N-methyl, and N-linked (CH₂)₅C(O)NH-(CH₂CH₂O)₁₂CH₂CH₂C(O)-NH-CH₂CH₂-SO₃⁻ chain] | 821 |
| 6 | [structure: 3-amino-6-azido acridinium with N-(CH₂)₃C(O)NH(CH₂CH₂O)₄CH₂CH₂CO₂H] | 334 |
| 7 | [structure: 3-amino-6-azido acridinium with N-(CH₂)₃C(O)NH(CH₂CH₂O)₄CH₂CH₂C(O)-NH-CH(CO₂H)(CH₂SO₃⁻)] | 485 |
| 10a and 10b | [structure: phenanthridinium dye (Ph, NH₂, N₃ substituents) with N-alkyl-C(O)NH(CH₂CH₂O)ₙCH₂CH₂CO₂H, CF₃CO₂⁻ counterion]<br>10a, n = 4<br>10b, n = 12 | 362 (10a) and 714 (10b) |

-continued

| Compound No. | Compound Structure | Molecular Mass of M Moiety |
|---|---|---|
| 020 | (structure) | 513 |
| 12 | (structure) | 673 |
| 13 | (structure) | 1394 |

-continued

| Compound No. | Compound Structure | Molecular Mass of M Moiety |
|---|---|---|
| 014 | 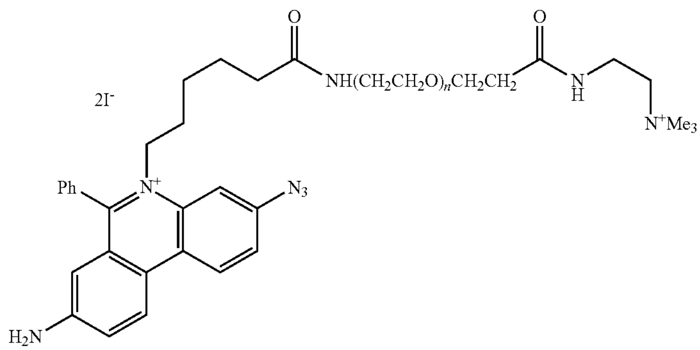 | 448 |
| 15 | 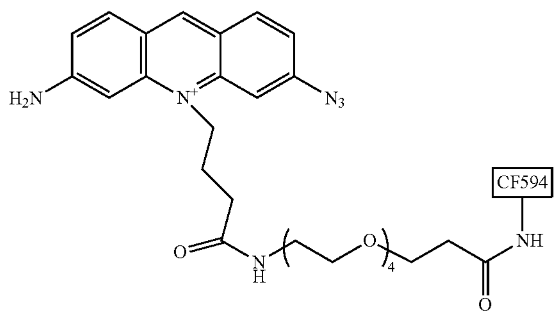 | >700 |
| 104.1 | 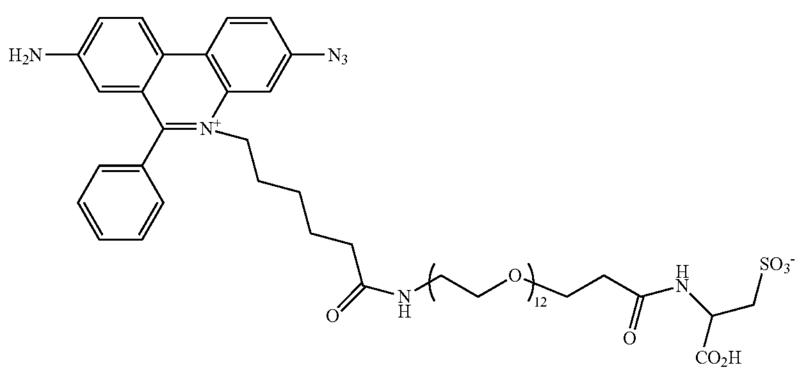 | 864 |
| 16 | 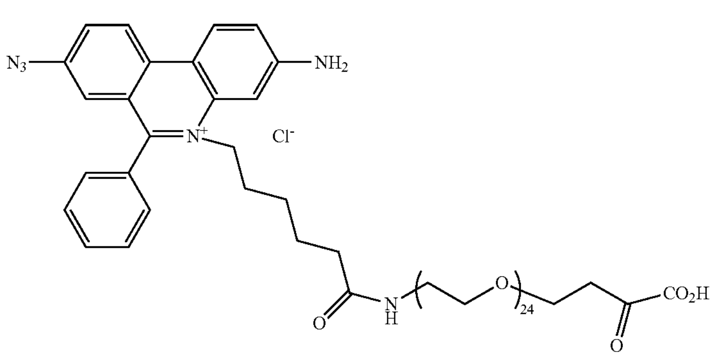 | 1703 |

-continued

| Compound No. | Compound Structure | Molecular Mass of M Moiety |
|---|---|---|
| 21 | 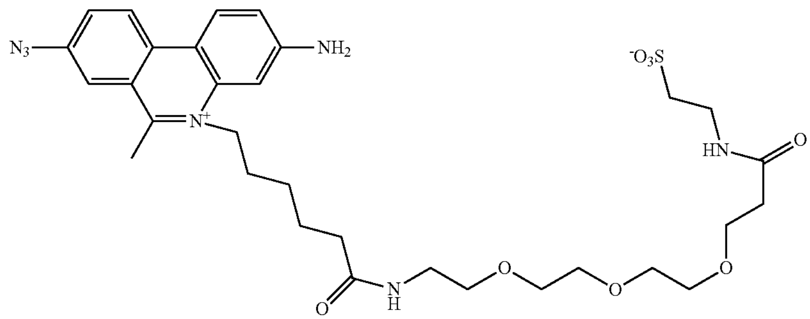 | 674 |
| 22 | 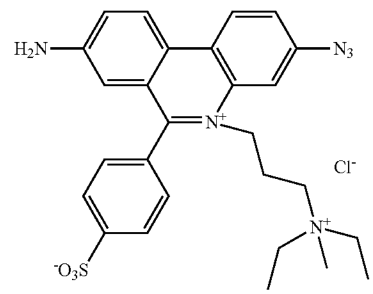 | 520 |
| 23 | 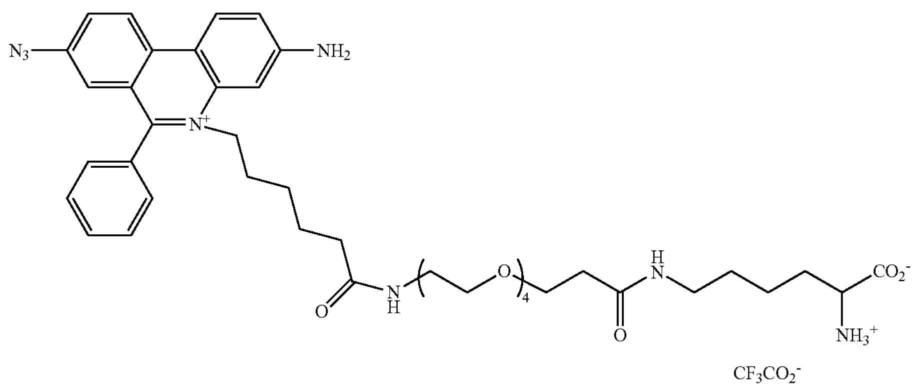 | 802 |
| 24 | 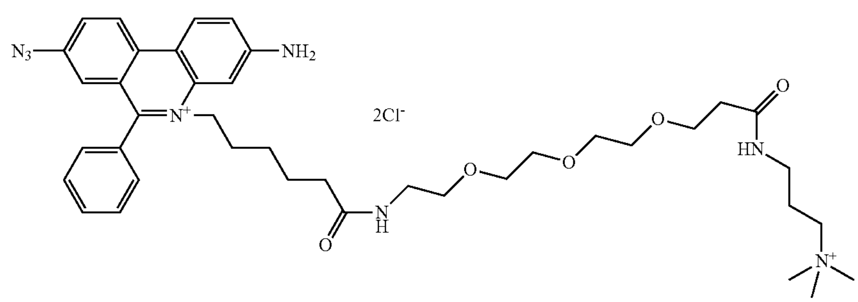 [SMILES: C[N+](C)(C)CCCNC(=O)CCOCCOCCOCCNC(=O)CCCCC[n+]1c(-c2ccccc2)c2cc(N=[N+]=[N-])ccc2c2ccc(N)cc21] | 728 |
| 25 | 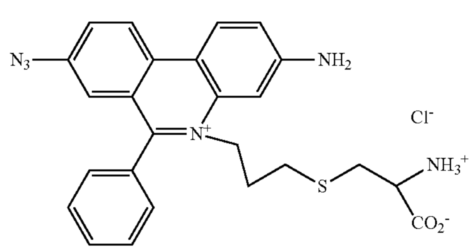 | 176 |

-continued

| Compound No. | Compound Structure | Molecular Mass of M Moiety |
|---|---|---|
| 26 | 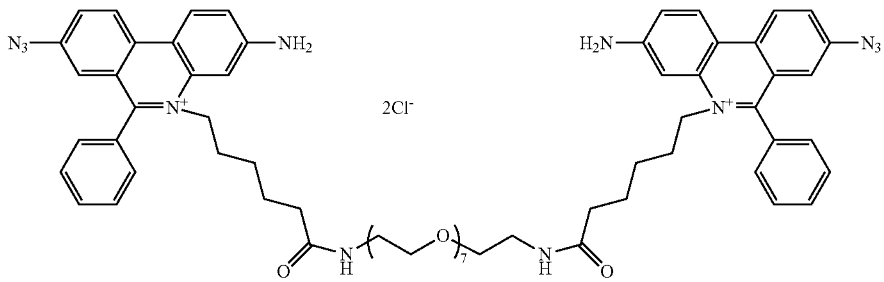 | 562 (and a = 2) |
| 27 | 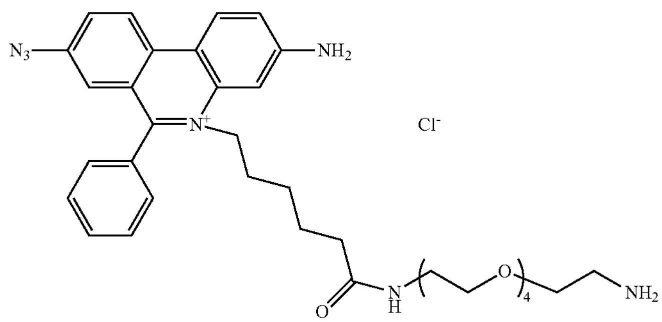 | 333 (M comprising a functional group) |
| 28 | 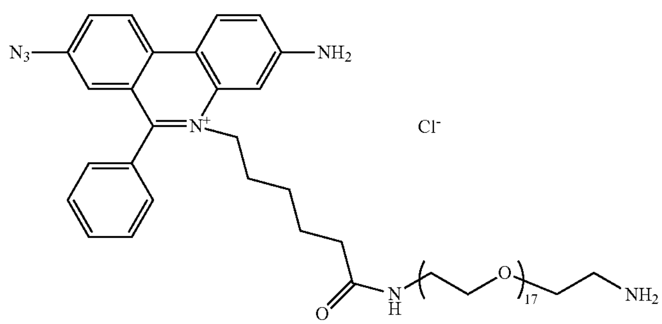 | 704 |
| 29 | 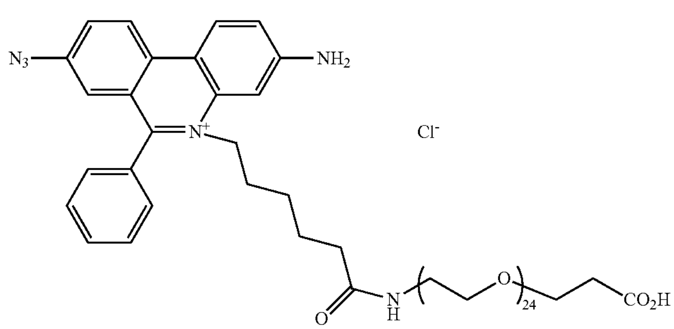 | 1240 |

| Compound No. | Compound Structure | Molecular Mass of M Moiety |
|---|---|---|
| 30 | ![structure] NH—(CH$_2$CH$_2$O)$_{24}$CH$_2$CH$_2$C(=O)—OH attached via amide to pentanoyl chain on N of pyridinium, linked by methylidene to benzothiazolium bearing N$_3$ and N-methyl, Cl$^-$ counterion | 1243 |

In one aspect, the disclosure provides a method of selectively labeling a non-viable organism or non-viable cell. In some embodiments, the method comprises contacting a compound of Formula A with a sample comprising viable and non-viable organisms or cells to effect formation of a complex comprising the compound and a nucleic acid of the non-viable organism or non-viable cell, thereby selectively labeling the non-viable organism or non-viable cell in the sample. In some embodiments, the compound is a compound of Formula A'. The non-viable organism may be a microorganism, non-limiting examples of which include bacteria, viruses, fungi, archaea, and protists. In some embodiments, the microorganisms are bacteria, and may further be gram-positive, gram-negative, or a mixture of both gram-positive and gram-negative bacteria. The non-viable cell can be a cell that is or was part of a multi-cellular organism, such as one or more cells of a tissue, organ, or other collection of cells. In general, "viable" refers to the ability of the organism or cell to reproduce, be metabolically active, or become metabolically active under conditions in which the organism or cell is typically associated with one or more of these activities. For example, a virus may be considered viable if at the time of collection it is capable of infecting a target cell to deliver its viral genome, and optionally generating copies of itself (alternatively referred to as "infectious"). As a further example, a bacterium may be considered viable if at the time of collection it is capable of metabolic activity and replication under typical growth conditions. As yet another example, a neuron may be considered viable if at the time of collection it was capable of propagating an action potential. Thus, a "non-viable" organism or cell generally refers to an organism or cell that is substantially not viable. In some embodiments, the non-viable organism is a non-infectious virus. In some embodiments, the non-viable organism is a dead bacterial cell.

In a related aspect, the disclosure provides a method of selectively labeling dead bacterial cells in a sample. In some embodiments, the method comprises contacting the sample with a compound that selectively modifies a nucleic acid of dead bacterial cells, wherein the compound is selective for dead gram-positive and dead gram-negative bacteria, thereby selectively labeling the dead bacterial cells in the sample. In some embodiments, the compound is characterized in that it selectively labels non-viable cells of one or more of *Staphylococcus aureus* (e.g. *S. aureus* collected by swabbing a surface), *Mycobacterium avium* subspecies *paratuberculosis* (MAP), *Salmonella* serovar *Enteritidis*, such as in an assay for the identifying the presence of viable and/or non-viable cells, including any such assay described herein. The functionality of distinguishing viable from non-viable cells of a selected type may be assessed using a control sample having a known composition, such as a population of cells treated to be non-viable (e.g. heat- or chemically-killed bacteria), a population of known viable cells, or a population having a known percentage of viable and non-viable cells. In some embodiments, the compound is a compound of Formula A. In some embodiments, the compound is a compound of Formula A'.

Typically, a sample comprises both viable and non-viable organisms and/or cells. Thus, by "selectively labeling" is meant a process by which more non-viable organisms and/or cells are labeled than are viable organisms and/or cells. For example, non-viable organisms or cells may be labeled at a rate that is about or more than about 2, 3, 4, 5, 6, 7, 8, 9, 10, 25, 50, 75, 100, 150, 200, 500, 1000, 10000, 100000, $10^6$, $10^7$, $10^8$, $10^9$, or more fold higher than the rate at which viable organisms or cells may be labeled. For example, if 99% of non-viable cells are labeled, while only 0.1% of viable cells are labeled, this would represent a 990-fold higher rate of labeling non-viable cells over viable cells. Selectivity may also be assessed by the ability to reduce PCR amplification of a target polynucleotide (e.g. 16S rRNA or rDNA) from a sample of killed cells or organisms (e.g. bacteria) under suitable conditions, relative to amplification for a comparable sample of viable cells or organisms under comparable conditions. For example, PCR amplification may be reduced by at least about 50%, 60%, 70%, 80%, 90%, 95%, 99%, or more. In some embodiments, PCR amplification from non-viable cells is reduced by at least 90% relative to a comparable sample of viable cells. In general, compounds of the present disclosure for selectively labeling non-viable organisms or cells are substantially more cell membrane-impermeable than nucleic acid-modifying agents like PMA, and thus have better selectivity in modifying nucleic acid from non-viable organisms and cells in the presence of viable organisms or cells. In some embodiments, the selective compounds are readily soluble in water such that any excess compound can be easily removed following a nucleic acid modification treatment.

A sample comprising viable and non-viable organisms or cells for use in any of the disclosed methods may be derived from any source. A sample can be an environmental sample, which includes samples collected from natural environments (e.g. a lake, a pond, soil, outdoor air), and artificial environments (e.g. a clean room, a spacecraft, a hospital facility, a food production facility, a neutraceutical or pharmaceutical facility, or a laboratory facility). In some embodiments, the sample is a food product, a neutraceutical product, a pharmaceutical product, a water sample, a soil sample, or a sample collected from a mammal. A sample can also be any sample obtained from a subject. Non-limiting examples of samples obtained from a subject include skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues. Subjects include, but are not limited to, murines, simians, humans, farm animals, sport animals, and pets. In some embodiments, the subject is a human.

In some embodiments, selectively labeling the non-viable organisms or cells in a sample comprises activating an activatable group of the compound of Formula A to effect conjugation between the compound and a nucleic acid in the sample to form a conjugate, or cleavage of nucleic acids in the sample. In some embodiments, the compound is a compound of Formula A'. Where the activatable group is a chemically activatable group, activation may comprise exposing the compound to a chemical agent, and optimal temperature, an optimal pH, or a combination of these. Where the activatable group is a photoreactive group, activation may comprise exposure to a suitable light source for a time sufficient to cause covalent modification of a nucleic acid by the compound. In some embodiments, the light is visible light, which may be from a natural or artificial source. For example, the light source can be an LED light, preferably with an output wavelength from 300 nm to about 600 nm, more preferably from 450 nm to 500 nm. The duration of activation, such as by exposure to light, can be for any suitable duration, such as from about 30 seconds to about 30 minutes. In some embodiments, the light exposure time is from about 5 minutes to about 20 minutes, or about 1 to 15 minutes. After activation, excess compound may optionally be removed, such as by washing and/or centrifugation. In some embodiments, the steps of contacting, activating, and removing excess compound are repeated one or more times (e.g. 1, 2, 3, 4, 5, 6, 7, 8, 9, 10, or more times) to enhance the degree of nucleic acid modification.

In some embodiments, the method of selectively labeling a non-viable organism or cell further comprises amplifying nucleic acids present in the sample to produce a detectable signal that is indicative of the presence of nucleic acids from a viable organism or cell. Amplifying nucleic acids from the sample may employ any suitable process. Typically, the first step involves lysis of intact organisms or cells to release nucleic acids into the medium. Lysis (e.g. chemical lysis or heat lysis) may be followed by amplification, or by intermediate extraction and purification steps. Multiple methods for nucleic acid extraction are available. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after subsequent manipulation, such as to remove excess or unwanted reagents, reactants, or products.

Lysis, and optional extraction and purification, may be followed by amplification of one or more target polynucleotides in a sample. In general, "amplification" refers to a process by which one or more copies are made of a target polynucleotide. A variety of amplification methods are available. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. Nos. 5,527,670, 6,033,850, 5,939,291, and 6,333,157), and application of an electromagnetic field in combination with primers bound to a magnetically-responsive material (e.g. U.S. Pat. No. 5,545,540). In a variation called RT-PCR, reverse transcriptase (RT) is used to make a complementary DNA (cDNA) from RNA, and the cDNA is then amplified by PCR to produce multiple copies of DNA (e.g. U.S. Pat. Nos. 5,322,770 and 5,310,652, which are hereby incorporated by reference in their entirety). Thus, RNA-based detection may be used for detecting a variety of RNA species, such as RNA from retroviruses. Examples of retroviruses include, but are not limited to, several types of HIV viruses, Ebola virus, and human T-cell leukemia virus. RNA detection can also be used to analyze gene expression in cells, such as selective analysis of gene expression in viable cells. This can be useful for obtaining a more accurate assessment of the gene activity in living healthy cells, as in a mixed population of live and dead cells the RNA product profiles may be quite different in the two cell groups.

One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g. U.S. Pat. Nos. 5,270,184 and 5,455,166). Thermophilic SDA (tSDA) uses thermophilic endonucleases and polymerases at higher temperatures in essentially the same method (European Pat. No. 0 684 315).

Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278). In some cases, isothermal amplification uses transcription by an RNA polymerase from a promoter sequence, such as may be incorporated into an oligonucleotide primer. Transcription-based amplification methods include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) BioTechnol. 6, 1197-1202); self-sustained sequence replication (e.g., Guatelli, J. et al. (1990) Proc. Natl. Acad. Sci. USA 87, 1874-1878; Landgren (1993) Trends in Genetics 9, 199-202; and HELEN H. LEE et al., NUCLEIC ACID AMPLIFICATION T TECHNOLOGIES (1997)); and methods for generating additional transcription templates (e.g. U.S. Pat. Nos. 5,480,784 and 5,399,491). Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers (e.g. U.S. Pat. Nos. 6,251,639, 6,946,251, and 7,824,890). Isothermal amplification processes can be linear or exponential.

In some embodiments, amplification methods include the production of a detectable signal. In some embodiments, the nucleic acids that are amplified in the amplification reaction are predominantly those that are not conjugated to the compound following activation of the activatable element. Where labeling and subsequent conjugation is selective for non-viable organisms or cells, conjugates that do not participate in the amplification reaction are predominantly those derived from non-viable organisms or cells. As a result, detecting the detectable signal is generally indicative of the presence of nucleic acids from a viable organism or cell. Detection may take place during an amplification process, such as during primer extension or between cycles of primer extension, also referred to as "real time" detection. Detection may also, or alternatively, take place at the end of an amplification process, such as at the end of multiple cycles of primer extension.

In some embodiments, the amplified products can be directly visualized with fluorescent DNA-binding agents, including but not limited to DNA intercalators and DNA groove binders. Because the amount of the intercalators incorporated into double-stranded DNA molecules is typically proportional to the amount of the amplified DNA products, one can conveniently determine the amount of the amplified products by quantifying the fluorescence of the intercalated dye using conventional optical systems. Non-limiting examples of DNA-binding dyes suitable for this application include SYBR green, SYBR blue, DAPI, propidium iodine, Hoechst stain, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like. In some embodiments, fluorescent labels such as sequence specific probes can be employed in the amplification reaction to facilitate the detection and quantification of the amplified products. Probe-based quantitative amplification relies on the sequence-specific detection of a desired amplified product. In some embodiments, it utilizes fluorescent, target-specific probes (e.g., TaqMan° probes) resulting in increased specificity and sensitivity. Available methods for performing probe-based quantitative amplification include those described in U.S. Pat. No. 5,210,015.

For convenient detection of the probe-target complexes formed during the hybridization assay, the nucleotide probes can be conjugated to a detectable label. Detectable labels suitable for use in the disclosed methods include any composition detectable by photochemical, biochemical, spectroscopic, immunochemical, electrical, optical, or chemical means. A wide variety of appropriate detectable labels are available, which include fluorescent or chemiluminescent labels, radioactive isotope labels, enzymatic or other ligands. In some embodiments, a fluorescent label or an enzyme tag is used, such as digoxigenin, β-galactosidase, urease, alkaline phosphatase or peroxidase, avidin/biotin complex. In some embodiments, the label is a fluorescent dye label, biotin, digoxigenin, or a hapten.

The detection methods used to detect or quantify the hybridization intensity will typically depend upon the label selected. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

In some embodiments, hybridization of a probe to a target sequence is detected directly by visualizing a bound probe (e.g., a Northern or Southern assay; See e.g., Ausabel et al. (eds.), Current Protocols in Molecular Biology, John Wiley & Sons, NY (1991)). In a typical blotting assay, genomic DNA (Southern) or RNA (Northern) is isolated from a sample of a subject. The DNA or RNA is then cleaved with a series of restriction enzymes that cleave infrequently in the genome. The DNA or RNA is then separated (e.g., on an agarose gel) and transferred to a membrane. A labeled (e.g., by incorporating a radionucleotide) probe or probes specific for the target polynucleotide being detected is allowed to contact the membrane under a condition of low, medium, or high stringency conditions. Unbound probe is removed and the presence of binding is detected by visualizing the labeled probe.

In some embodiments, one or more target polynucleotide sequences are detected using an array-based hybridization assay (alternative referred to as "microarray" assay) to produce the detectable signal. In this assay, a series of oligonucleotide probes are affixed to a solid support. The oligonucleotide probes are designed to be unique to a given target sequence (e.g. 16S rRNA from a particular bacterial species or group of species). The DNA sample of interest (e.g. amplified polynucleotides) is contacted with the oligonucleotide probe array and hybridization is detected. In some embodiments, the probe array assay is a GeneChip (Affymetrix, Santa Clara, Calif.; See e.g., U.S. Pat. Nos. 6,045,996; 5,925,525; and 5,858,659) assay. The GeneChip technology uses miniaturized, high-density arrays of oligonucleotide probes affixed to an array or "chip." Example probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

In some embodiments, the nucleic acid to be analyzed on a probe array is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined. In some embodiments, In some embodiments, a probe array containing electronically captured probes (Nanogen, San Diego, Calif.) is utilized (See e.g., U.S. Pat. Nos. 6,017,696; 6,068,818; and 6,051,380). Through the use of microelectronics, Nanogen's technology enables the active movement and concentration of charged molecules to and from designated test sites on its semiconductor microchip. Nucleic acid capture probes unique to a given SNP or mutation are electronically placed at, or "addressed" to, specific sites on the microchip. Since DNA has a strong negative charge, it can be electronically moved to an area of positive charge. First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample can then be analyzed for the presence of target DNA molecules by determining which of the DNA capture probes hybridize with complementary DNA in the test sample (e.g., a PCR amplified gene of interest). An electronic charge can also be used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. A laser-based fluorescence scanner is used to detect binding.

In some embodiments, a "bead array" is used for the detection of target polynucleotides, such as amplified polynucleotides (Illumina, San Diego, Calif.; See e.g., PCT Publications WO 99/67641 and WO 00/39587). Illumina uses a bead array technology that combines fiber optic bundles and beads that self-assemble into an array. Each fiber optic bundle contains thousands to millions of individual fibers depending on the diameter of the bundle. The beads are coated with an oligonucleotide specific for the detection of a target sequence. Batches of beads are combined to form a pool specific to the array. To perform an assay, the bead array is contacted with a prepared sample (e.g., DNA). Hybridization is detected using any suitable method.

In some embodiments, hybridization of a bound probe is detected using a TaqMan assay (see e.g., U.S. Pat. Nos. 5,962,233 and 5,538,848). The assay is performed during a PCR reaction. The TaqMan assay exploits the 5'-3' exonuclease activity of DNA polymerases such as AMPLITAQ DNA polymerase. A probe specific for a target sequence (such as a 16S rRNA sequence of a particular bacterial species of group of species) is included in the PCR reaction. The probe typically comprises an oligonucleotide with a 5'-reporter dye (e.g., a fluorescent dye) and a 3'-quencher dye. During PCR, if the probe is bound to its target, the 5'-3' nucleolytic activity of the polymerase cleaves the probe between the reporter and the quencher dye. The separation of the reporter dye from the quencher dye results in an increase of fluorescence. The signal accumulates with each cycle of PCR and can be monitored with a fluorimeter, such as continuously, after each cycle, or at the end of amplification.

In some embodiments, the amplification reaction comprises or is followed by a sequencing reaction, such that the detectable signal indicative of nucleic acids from a viable organism or cell corresponds to one or more target polynucleotide sequences from the viable organism or cell. In some embodiments, a sequencing reaction comprising extension of an oligonucleotide primer is used to determine the nucleotide sequence of one or more target sequences from one or more viable organisms or cells. The template in a sequencing reaction may be nucleic acids isolated from a sample, nucleic acid amplification products, or a combination of these. Sequence analysis using template dependent synthesis can include a number of different processes. For example, in four-color Sanger sequencing methods, a population of template molecules is used to create a population of complementary fragment sequences. Primer extension is carried out in the presence of the four naturally occurring nucleotides, and with a sub-population of dye labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the sequence beyond the primer, and are labeled in a manner that permits identification of the terminating nucleotide. The nested fragment population is then subjected to size based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534).

Other examples of template dependent sequencing methods include sequencing by synthesis processes, where individual nucleotides are identified iteratively, as they are added to the growing primer extension product. These processes generally fall into two categories. In a first category, a nucleic acid synthesis complex is contacted with one or more nucleotides under conditions that permit the addition of a single base, and little or no extension beyond that base. The reaction is then interrogated or observed to determine whether a base was incorporated, and provide the identity of that base. The second category generally provides for the real-time observation of the addition of nucleotides to the growing nascent strand in an uninterrupted reaction process, e.g., without wash steps.

One example of the first category of processes is pyrosequencing, which is a sequence-by-synthesis process that identifies the incorporation of a nucleotide by assaying the resulting synthesis mixture for the presence of by-products of the sequencing reaction, namely pyrophosphate. In particular, a primer, polymerase template complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template nucleic acid. See, e.g., U.S. Pat. No. 6,210,891.

In certain other related processes, the primer-template-polymerase complex is immobilized upon a substrate and the complex is contacted with labeled nucleotides. In some embodiments, the nucleotides are provided with and without removable terminator groups, and upon incorporation, the label is coupled with the complex and is thus detectable. In the case of terminator-bearing nucleotides, all four different nucleotides, bearing individually identifiable labels, are contacted with the complex. Incorporation of the labeled nucleotide arrests extension, by virtue of the presence of the terminator, and adds the label to the complex. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246.

As noted above, in the second category of sequence-by-synthesis processes, the incorporation of differently labeled nucleotides is observed in real time as template-dependent synthesis is carried out in a processive manner. In particular, an individual immobilized polymerase-template-primer complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a $\beta$, $\gamma$, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This strategy results in a characteristic signal associated with the incorporation event, which is also characterized by a signal profile that is specific for the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results that is, again, also specific for the base being incorporated (See, e.g., U.S. Pat. No. 7,056,661).

The target polynucleotide amplified in an amplification step can be any suitable target. Typically, the target polynucleotide is one that is common to both viable and non-viable organisms or cells of the type being detected. In some embodiments, a method targets known diversity within target nucleic acid molecules to determine the composition of a mixed population of organisms or cells. Non-limiting examples of mixed populations include taxa within a microbial community, and cell types within a tissue (e.g. stem and non-stem cells, such as in a cancer tissue). The target nucleic acid molecule can be a highly conserved polynucleotide. In some embodiments, the highly conserved polynucleotide is from a highly conserved gene, whereas in other embodiments the polynucleotide is from a highly conserved region of a gene with moderate or large sequence variation. In some embodiments, the highly conserved region can be an intron, exon, or a linking section of nucleic acid that separates two genes. In some embodiments, the highly conserved polynucleotide is from a "phylogenetic" gene. Phylogenetic genes include, but are not limited to, the 5.8S rRNA gene, 12S rRNA gene, 16S rRNA gene-prokaryotic, 16S rRNA gene-mitochondrial, 18S rRNA gene, 23S rRNA gene, 28S rRNA gene, gyrB gene, rpoB gene, fusA gene, recA gene, coxl gene, and the nifD gene. With eukaryotes, the rRNA gene can be nuclear, mitochondrial, or both. In some embodiments, the 16S-23S rRNA gene internal transcribed spacer (ITS) can be used for differentiation of closely related taxa with or without the use of other rRNA genes. For example, rRNA, e.g., 16S or 23S rRNA, acts directly in the protein assembly machinery as a functional molecule rather than having its genetic code translated into protein. Due to structural constraints of 16S rRNA, specific regions throughout the gene have a highly conserved polynucleotide sequence; although, non-structural segments can have a high degree of variability. Probing the regions of high variability can be used to identify taxa that represent a single species level, while regions of less variability can be used to identify taxa that represent a subgenus, a genus, a subfamily, a family, a sub-order, an order, a sub-class, a class, a sub-phylum, a phylum, a sub-kingdom, or a kingdom. Methods, such as those described in U.S. Pat. No. 8,771,940 and US 20120165215, can be used to select organism-specific and taxa-specific oligonucleotide probes that offer a high level of specificity for the identification of specific organisms, taxa representing specific organisms, or taxa representing specific taxonomic group of organisms.

Methods for manipulating nucleic acids are generally much faster than time scales associated with replication of cells and organisms, such as in bacterial culture and tissue culture methods. As such, the detectable signal indicative of the presence of a nucleic acid from a viable organism or cell may be likewise produced on a faster time scale. In some embodiments, the detectable signal is produced within 72, 48, 24, 12, 6, or fewer hours from obtaining the sample, or from the time of beginning a sample analysis procedure (such as when a sample has been stored). In some embodiments, the presence of a viable cell or organism is detected within about 24 hours after obtaining the sample.

In some embodiments, the number of viable organisms or cells and/or the number of non-viable organisms or cells is determined. When both viable and non-viable organisms or cells are enumerated, either or both may be expressed as a fraction of the total. In some embodiments, a standard curve is generated using known amounts of a known viable microorganism to correlate the amount of detected nucleic acid to the number of viable organisms. In some cases, as a control, the nucleic acid from both viable and dead organism may be detected in a sample untreated with a modifier of the invention so that the total number of viable and dead organism can be quantified.

Other methods for the detection of non-viable and/or viable cells or organisms are available. In some embodiments, the method of selectively labeling further comprises (i) labeling both viable and non-viable organisms or cells with a common label; (ii) assaying for a first signal from the compound and a second signal from the common label; and (iii) identifying a test organism or test cell as non-viable if the test organism or cell is associated with both the first and second signals, or viable if the test organism or cell is associated with the second signal and substantially not associated with the first signal. In general, where compounds of the present disclosure that are selective for non-viable organisms and cells also comprise a label (e.g. a dye), the signal from the label will be selectively associated with the non-viable organisms or cells in a sample. Absence of signal from the compound is thus indicative of cell viability. Accordingly, a method may comprise assaying for the presence of a cell and for the presence of a signal from the compound. In some cases, the absence of first signal from a viable organism or cell may not be absolute, as labeling may depend on the degree of selectivity of the selected compound given the selected organism or cell. However, labeling of the viable cell will substantially lack the first signal, by comparison to the level of first signal associated with the population of non-viable organisms or cells. For example, measurement of the first signal may produce a bi-modal distribution in which the mean level of the first signal associated with a population of non-viable organisms or cells is at least 1 standard deviation higher than the mean level of the first signal associated with a population of viable organisms or cells in the sample. In some embodiments, the average levels of first signal associated with viable and non-viable populations in a sample are separated by about or more than about 1, 1.1, 1.2, 1.3, 1.4, 1.5, 1.6, 1.7, 1.8, 1.9, 2, 2.5, 3, 4, 5, or more standard deviations. In some embodiments, the separation is at least 2 standard deviations.

Assaying for the presence of a cell or organism need not involve a second label. For example, an organism or cell may be identified by characteristics inherently associated with the organism or cell, such as visual appearance (as in microscopy), or optical properties (e.g. fluorescence, luminescence, refraction, and scattering). In preferred embodiments, however, a second label is applied to enhance detection of organisms or cells (or one or more components thereof) in a sample. Any suitable method for detecting organisms or cells in a sample may be used, including but not limited to, microscopy and cytometry methods.

In some embodiments, one or more signals associated with a cell are detected using a cytometry assay. Cytometry assays are typically used to optically, electrically, or acoustically measure characteristics of individual cells. Such characteristics include but are not limited to size; shape; granularity; light scattering pattern (or optical indicatrix); whether the cell membrane is intact; concentration, morphology and spatio-temporal distribution of internal cell contents, including but not limited to protein content, protein modifications, nucleic acid content, nucleic acid modifications, organelle content, nucleus structure, nucleus content, internal cell structure, contents of internal vesicles (including pH), ion concentrations, and presence of other small molecules such as steroids or drugs; and cell surface (both cellular membrane and cell wall) markers including proteins, lipids, carbohydrates, and modifications thereof. By using appropriate dyes, stains, or other labeling molecules either in pure form, conjugated with other molecules or immobilized in, or bound to nano- or micro-particles, cytometry may be used to determine the presence, quantity, and/or modifications of specific proteins, nucleic acids, lipids, carbohydrates, or other molecules. Properties that may be measured by cytometry also include measures of cellular function or activity, including but not limited to phagocytosis, antigen presentation, cytokine secretion, changes in expression of internal and surface molecules, binding to other molecules or cells or substrates, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. The assays described herein may be used to measure one or more of the above characteristics for each cell, which may be advantageous to determine correlations or other relationships between different characteristics. The assays described herein may also be used to independently measure multiple populations of cells, for example by labeling a mixed cell population with antibodies specific for different cell lines. In addition to the above characteristics, by detection of the presence or absence of a signal from a compound of the present disclosure, contribution of one or more other signals from viable organisms or cells may be distinguished from those of non-viable organisms or cells.

Flow cytometry may be used to measure, for example, cell size (forward scatter, conductivity), cell granularity (side scatter at various angles), DNA content, dye staining, and quantitation of fluorescence from labeled markers. Flow cytometry may be used to perform cell counting, such as by marking the sample with fluorescent markers and flowing past a sensing device. In some embodiments, up to 1,000,000 organisms or cells of any given type may be measured. In other embodiments, various numbers of organisms or cells of any given type may be measured, including but not limited to more than or equal to about 10, 100, 1000, 10000, 100000, $10^6$, $10^7$, $10^8$, or more organisms or cells. In some embodiments, flow cytometry may be performed in microfluidic channels. Flow cytometry analysis may be performed in a single channel or in parallel in multiple channels. Flow cytometry may be combined with cell sorting, where detection of cells that fulfill a specific set of characteristics (e.g. viable or non-viable) are diverted from the flow stream and collected for storage, additional analysis, and/or processing. It should be noted that such sorting may separate out multiple populations of cells based on different sets of characteristics, such as 3 or 4-way sorting.

In some embodiments, one or more signals associated with a cell are detected using a microscopy assay. Microscopy methods include but are not limited to bright field, oblique illumination, dark field, dispersion staining, phase contrast, differential interference contrast (DIC), polarized light, epifluorescence, interference reflection, fluorescence, confocal (including CLASS), confocal laser scanning microscopy (CLSM), structured illumination, stimulated emission depletion, electron, scanning probe, infrared, laser, widefield, light field microscopy, lensless on-chip holographic microscopy, digital and conventional holographic microscopy, extended depth-of-field microscopy, optical scatter imaging microscopy, deconvolution microscopy, defocusing microscopy, quantitative phase microscopy, diffraction phase microscopy, confocal Raman microscopy, scanning acoustic microscopy and X-ray microscopy. Magnification levels used by microscopy may include, as non-limiting examples, up to 2×, 5×, 10×, 20×, 40×, 60×, 100×, 100×, 1000×, or higher magnifications. Feasible magnification levels will vary with the type of microscopy used. Multiple microscopy images may be recorded for the same sample to generate time-resolved data, including videos. Individual or multiple cells may be imaged simultaneously, by parallel imaging or by recording one image that encompasses multiple cells. A microscopic objective may be immersed in media to change its optical properties, such as through oil immersion. A microscopic objective may be moved relative to the sample by means of a rotating CAM to change the focus. Cytometry data may be processed automatically or manually, and may further include analyses of cell or tissue morphology, such as by a pathologist for diagnostic purposes.

Cell counting can be performed using imaging and cytometry, including counting of viable or non-viable cells. In situations where the subjects may be bright-field illuminated, the preferred embodiment is to illuminate the subjects from the front with a white light and to sense the cells with an imaging sensor. Subsequent digital processing will count the cells. Where the cells are infrequent or are small, the preferred embodiment is to attach a specific or non-specific fluorescent marker, and then illuminate the subject field with a laser. In some embodiments, up to 1000 cells of any given type may be counted. In other embodiments, various numbers of cells of any given type may be counted, including but not limited to more than or equal to about 1 cell, 5 cells, 10 cells, 30 cells, 50 cells, 100 cells, 150 cells, 200 cells, 300 cells, 500 cells, 700 cells, 1000 cells, 1500 cells, 2000 cells, 3000 cells, 5000 cells, or more. Cells may be counted using available counting algorithms. Cells can be recognized by their characteristic fluorescence, size, shape, and/or the presence of a label.

In some microscopy embodiments, darkfield imaging may be achieved by the use of a ringlight based illumination scheme, or other epi- or trans-darkfield illumination schemes available. Darkfield imaging may, for example, be used to determine light scattering properties of cells, equivalent to side scatter in flow cytometry, such as when imaging human leukocytes. The internal and external features of the cell which scatter more light appear brighter and the features which scatter lesser amounts of light appear darker in a darkfield image. Cells such as granulocytes have internal granules of size range (100-500 nm) which can scatter significant amount of light and generally appear brighter in darkfield images. Furthermore, the outer boundary of any cell may scatter light and may appear as a ring of bright light. The diameter of this ring may directly give the size of the cell. In some microscopy embodiments, small cells or formed elements which may be below the diffraction-limited resolution limit of the microscope, may be labeled with fluorescent markers; the sample may be excited with light of appropriate wavelength and an image may be captured.

Cell imaging may be used to extract one or more of the following information for each cell (but is not limited to the following): cell size; quantitative measure of cell granularity or light scattering (also popularly called side scatter, based on flow cytometry parlance); quantitative measure of fluorescence in each spectral channel of imaging, after compensating for cross-talk between spectral channels, or intracellular distribution pattern of fluorescent or other staining; shape of the cell, as quantified by standard and custom shape attributes such as aspect ratio, Feret diameters, Kurtosis, moment of inertia, circularity, solidity etc.; color, color distribution and shape of the cell, in cases where the cells have been stained with dyes (not attached to antibodies or other types of receptor); intracellular patterns of staining or scattering, color or fluorescence that are defined as quantitative metrics of a biological feature such as morphology, for example density of granules within cells in a darkfield image, or the number and size of nucleolar lobes in a Giemsa-Wright stained image of polymorphonuclear neutrophils etc.; co-localization of features of the cell revealed in images acquired in different channels; spatial location of individual cells, cellular structures, populations of cells, intracellular proteins, ions, carbohydrates and lipids or secretions (such as to determine the source of secreted proteins).

In some embodiments, the microscopy method utilizes fluorescence microscopy, such as to detect a signal from the compound and/or a second label. Microscopic imaging of fluorescently labeled samples may gather information regarding the presence, amounts, and locations of the target that is labeled at a given moment in time or over a period of time. Fluorescence may also be used to enhance sensitivity for detecting cells, cellular structures, or cellular function. In fluorescence microscopy, a beam of light is used to excite the fluorescent molecules, which then emit light of a different wavelength for detection. Sources of light for exciting fluorophores are well known in the art, including but not limited to xenon lamps, lasers, LEDs, and photodiodes. Detectors include but are not limited to PMTs, CCDs, and cameras.

In addition to a compound of the present disclosure, such as a compound of Formula A or Formula A', organisms or cells may be stained with one or more additional labels (e.g. 1, 2, 3, 4, 5, 6, 7, 8, 9, 10, or more labels). Labels include any optically detectable dye, stains, or coloring agents, such as nucleic acid dyes (including intercalator dyes), lipophilic dyes, protein dyes, carbohydrate dyes, heavy metal stains. Such dyes and stains or staining processes include but are not limited to Acid Fast Bacilli staining, Alcian Blue staining, Alcian Blue/PAS staining, Alizarin Red, alkaline phosphatase staining, amino styryl dyes, ammonium molybdate, Azure A, Azure B, Bielschowsky Staining, Bismark brown, cadmium iodide, carbocyanines, carbohydrazide, carboindocyanines, Carmine, Coomassie blue, Congo Red, crystal violet, DAPI, ethidium bromide, Diff-Quik staining, eosin, ferric chloride, fluorescent dyes, fuchsin, Giemsa stain, Golgi staining, Golgi-Cox staining, Gomori's Trichrome staining, Gordon Sweet's staining, Gram staining, Grocott Methenamine staining, haematoxylin, hexamine, Hoechst stains, Hyaluronidase Alcian Blue, indium trichloride, indocarbocyanines, indodicarbocyanines, iodine, Jenner's stain, lanthanum nitrate, lead acetate, lead citrate, lead(II) nitrate, Leishman stain, Luna staining, Luxol Fast Blue, Malachite green, Masson Fontana staining, Masson Trichrome staining, methenamine, methyl green, methyline blue, microglia staining, Miller's Elastic staining, neutral red, Nile blue, Nile red, Nissl staining, Orange G, osmium tetroxide, Papanicolaou staining, PAS staining, PAS diastase staining, periodic acid, Perls Prussian Blue, phosphomolybdic acid, phosphotungstic acid, potassium ferricyanide, potassium ferrocyanide, Pouchet staining, propidium iodide (PI), Prussian Blue, Renal Alcian Blue/PAS staining, Renal Masson Trichrome staining, Renal PAS Methenamine staining, Rhodamine, Romanovsky stain, Ruthenium Red, Safranin O, silver nitrate, Silver staining, Sirius Red, sodium chloroaurate, Southgate's Mucicannine, Sudan staining, Sybr Green, Sybr Gold, SYTO dyes, SYPRO stains, thallium nitrate, thiosemicarbazide, Toluidine Blue, uranyl acetate, uranyl nitrate, van Gieson staining, vanadyl sulfate, von Kossa staining, WG staining, Wright-Giemsa stain, Wright's stain, X-Gal, and Ziehl Neelsen staining. Cells may be treated with uncolored dye precursors that are converted to a detectable product after treatment, such as by enzymatic modification (such as by peroxidases or luciferases) or binding to an ion (such as Fe ions, Ca2+ or H+).

Cells may further be labeled with fluorescent markers. Useful fluorescent markers include natural and artificial fluorescent molecules, including fluorescent proteins, fluorophores, quantum dots, and others. Some examples of fluorescent markers that may be used include but are not limited to: 1,5 IAEDANS; 1,8-ANS; 5-carboxy-2,7-dichlorofluorescein; 5-Carboxyfluorescein (5-FAM); fluorescein amidite (FAM); 5-Carboxynapthofluorescein; tetrachloro-6-carboxyfluorescein (TET); hexachloro-6-carboxyfluorescein (HEX); 2,7-dimethoxy-4,5-dichloro-6-carboxyfluorescein (JOE); VIC®; NED™; tetramethylrhodamine (TMR); 5-Carboxytetramethylrhodamine (5-TAMRA); 5-HAT (Hydroxy Tryptamine); 5-Hydroxy Tryptamine (HAT); 5-ROX (carboxy-X-rhodamine); 6-Carboxyrhodamine 6G; 6-JOE; Light Cycler® red 610; Light Cycler® red 640; Light Cycler® red 670; Light Cycler® red 705; 7-Amino-4-methylcoumarin; 7-Amino actinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AutoFluorescent Proteins; Texas Red and related molecules; Thiadicarbocyanine (DiSC3); Thiazine Red R; Thiazole Orange; Thioflavin derivatives; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamine-lsoThioCyanate); True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor® dye series (from Molecular Probes/Invitrogen) such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), such as Cy3, Cy3B, Cy3.5, Cy5, Cy5.5, Cy7; members of the Oyster® dye fluorophores (Denovo Biolabels) such as Oyster-500, -550, -556, 645, 650, 656; members of the DY-Labels series (Dyomics), such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor® series or Quasar® series of dyes (Biosearch Technologies) such as CAL Fluor® Gold 540, CAL Fluor® Orange 560, Quasar® 570, CAL Fluor® Red 590, CAL Fluor® Red 610, CAL Fluor® Red 635, Quasar® 570, and Quasar® 670.

Fluorescent markers may be coupled to a targeting moiety to allow specific binding or localization, for example, to a specific population of organisms or cells. Non-limiting examples include antibodies, antibody fragments, antibody derivatives, aptamers, oligopeptides such as the nuclear localization sequence (NLS), small molecules that serve as specific ligands for receptors including many hormones and drugs, nucleic acid sequences (such as for FISH), nucleic acid binding proteins (including repressors and transcription factors), cytokines, ligands specific for cellular membranes, enzymes, molecules that specifically bind to enzymes (such as inhibitors), lipids, fatty acids, and members of specific binding interactions such as biotin/iminobiotin and avidin/streptavidin. Compounds of the present disclosure are particularly advantageous for use in immunostaining procedures. Following conjugation by activating an activatable group in the compound, a sample may be fixed and optionally permeabilized using standard conditions. Fixation and permeabilization are typically used to introducing large molecules, such as antibodies, into cells, or for making cellular proteins more accessible for probing. Conventional nucleic acid binding dyes, such as propidium iodide or ethodium homodimer, cannot tolerate this process because the organic reagents used for the process, i.e., formaldehyde and detergent, weaken the dye-nucleic acid interaction, resulting in dye loss. In contrast, by covalently attaching a compound of the present disclosure, such as a compound comprising a label, to the nucleic acid, dead cell labeling with the label (e.g. a dye) is not affected by the fixation and permeabilization reagents. The fixed and permeabilized sample may be subject to further staining by one or more fluorescent probes, such as described herein. In some cases, the staining may comprise incubating the sample with one or more unlabeled primary antibodies, followed by staining with fluorescently labeled matching secondary antibodies. In some cases, the sample may be stained with one or more fluorescently labeled primary antibodies (e.g. 1, 2, 3, 4, 5, 6, 7, 8, 9, 10, or more). In some cases, the sample may be further stained with one or more additional polypeptide- or protein-based fluorescent probes, including but not limited to fluorescently labeled Annexin V, fluorescently labeled toxins, and fluorescently labeled wheat germ agglutinins, for example. The labeled sample may then be analyzed by any appropriate method, including a method disclosed herein.

As with nucleic acid amplification methods, cytometry and microscopy methods are generally faster than culturing methods for detecting viable organisms. As such, identifying a test organism or cells as viable or non-viable (and optionally determining the identity and/or quantity of a particular type of test organism or cell) may be likewise produced on a faster time scale. In some embodiments, the identifying signal or signals are produced within 72, 48, 24, 12, 6, or fewer hours from obtaining the sample, or from the time of beginning a sample analysis procedure (such as when a sample has been stored). In some embodiments, the presence of a viable cell or organism is detected within about 24 hours after obtaining the sample.

In one aspect, the disclosure provides a method of detecting viable microorganisms in a sample, such as may be associated with or indicative of infection or contamination. In some embodiments, the method comprises: (a) contacting a compound of Formula A with the sample (e.g. a sample suspected to be infected or contaminated), thereby forming a mixture; (b) activating an activatable group of the compound to effect (i) conjugation between the compound and nucleic acids in the mixture to form conjugates, or (ii) cleavage of nucleic acids in the mixture; (c) detecting presence of viable microorganisms (e.g. microorganisms indicative of contamination or active infection) by: (i) amplifying nucleic acids present in said sample to produce a detectable signal, wherein the signal is indicative of the presence of nucleic acids from a viable microorganism; or (ii) (A) labeling both viable and non-viable microorganisms with a common label; (B) assaying for a first signal from the compound and a second signal from the common label; and (C) identifying a test microorganism as non-viable if the test microorganism is associated with both the first and second signals, or viable if the test microorganism is associated with the second signal and substantially not associated with the first signal. In some embodiments, the compound is a compound of Formula A'. In some embodiments, amplifying nucleic acids comprises a reverse transcription step to convert a target RNA associated with the viable microorganism to cDNA.

In a related aspect, the disclosure provides a method of detecting viable bacteria in a sample. In some embodiments, the method comprises: (a) contacting the sample with a compound that selectively modifies a nucleic acid of dead bacterial cells, thereby forming a mixture; wherein the compound is characterized in that it selectively labels non-viable bacteria selected from the group consisting of *Staphylococcus aureus* (e.g. Methicillin-resistant *Staphylococcus aureus*, MRSA) collected by swabbing a surface, *Mycobacterium avium* subspecies *paratuberculosis* (MAP), and *Salmonella* serovar *Enteritidis*, in a control sample comprising the bacteria; (b) activating an activatable group of the compound to effect (i) conjugation between the compound and nucleic acids in the mixture to form conjugates, or (ii) cleavage of nucleic acids in the mixture; (c) detecting presence of viable bacteria by: (i) amplifying nucleic acids present in said sample to produce a detectable signal, wherein the signal is indicative of the presence of nucleic acids from a viable microorganism; or (ii) (A) labeling both viable and non-viable bacterial cells with a common label; (B) assaying for a first signal from the compound and a second signal from the common label; and (C) identifying a test microorganism as non-viable if the test microorganism is associated with both the first and second signals, or viable if the test microorganism is associated with the second signal and substantially not associated with the first signal. In some embodiments, the compound selectively labels non-viable cells of one or more of *Staphylococcus aureus* (e.g. *S. aureus* collected by swabbing a surface), *Mycobacterium avium* subspecies *paratuberculosis* (MAP), *Salmonella* serovar *Enteritidis*, such as in an assay for the identifying the presence of viable and/or non-viable cells, including any such assay described herein. The functionality of distinguishing viable from non-viable cells of a selected type may be assessed using a control sample having a known composition, such as a population of cells treated to be non-viable (e.g. heat- or chemically-killed bacteria), a population of known viable cells, or a population having a known percentage of viable and non-viable cells. In some embodiments, the compound is a compound of Formula A. In some embodiments, the compound is a compound of Formula A'. In some embodiments, labeling of the viable cell will substantially lack the first signal by comparison to the level of first signal associated with the population of non-viable organisms or cells. For example, measurement of the first signal may produce a bi-modal distribution in which the mean level of the first signal associated with a population of non-viable organisms or cells is at least 1 standard deviation higher than the mean level of the first signal associated with a population of viable organisms or cells in the sample. In some embodiments, the average levels of first signal associated with viable and non-viable populations in a sample are separated by about or more than about 1, 1.1, 1.2, 1.3, 1.4, 1.5, 1.6, 1.7, 1.8, 1.9, 2, 2.5, 3, 4, 5, or more standard deviations. In some embodiments, the separation is at least 2 standard deviations.

In some embodiments, the viable microorganisms detected by a method disclosed herein comprise one or more different viable bacteria associated with a disease condition, also referred to as pathogenic bacteria. In some embodiments, the presence, absence, and/or quantity of about or more than about 1, 2, 3, 4, 5, 6, 7, 8, 9, 10, 15, 25, 25, 50, 75, 100, 500, 1000, 10000, or more different bacterial taxa (e.g. genus or species) are assessed in accordance with a method of the present disclosure. Non-limiting examples of bacterial taxa to be detected include *Pseudomonas, Streptococcus, Staphylococcus, E. coli, Haemophilus, Mycobacterium, Proteus, Klebsiella, Neisseria, Branhamella, Bacteroides, Listeria, Enterococci, Vibrio, Yersinia, Bordetella, Clostridium, Treponema*, and *Mycoplasma*. Additional examples include, but are not limited to, *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus (anaerobic* sps.), *Streptococcus pneumoniae*, pathogenic *Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

In some embodiments, the viable microorganisms detected by a method disclosed herein comprise one or more different infectious viruses associated with a disease condition. In some embodiments, the presence, absence, and/or quantity of about or more than about 1, 2, 3, 4, 5, 6, 7, 8, 9, 10, 15, 25, 25, 50, 75, 100, 500, 1000, 10000, or more different viral taxa are assessed in accordance with a method of the present disclosure. Non-limiting examples of viral taxa to be detected include Retroviridae (for example, human immunodeficiency viruses, such as HIV-1 (also referred to as HTLV-III, LAV or HTLV-III/LAV, or HIV-III) and other isolates, such as HIV-LP; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV)-1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of *Spongiform encephalopathies*, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses). In some embodiments, detection of retroviruses comprises reverse transcription and cDNA amplification.

In some embodiments, the method selected for detecting the presence of viable microorganisms, such as bacteria, comprises an amplification process. A variety of suitable amplification and detection processes are available, including any amplification and detection process described herein (e.g. PCR- and sequencing-related methods). Where desired, the amplification process may employ one or more labels and detection methods, as described herein. In some embodiments, the method selected for detecting the presence of viable microorganisms, such as bacteria, comprises a process for labeling cells and identifying a cell as viable or non-viable based on an identifiable characteristic. A variety of indicators for the presence of cells or cellular components, including intrinsic cellular characteristics and labels, are available, non-limiting examples of which are described herein. As noted herein, a variety of cellular detection methodologies are available, non-limiting examples of which include microscopy and cytometry methods.

A sample comprising viable and non-viable organisms or cells, such as microorganisms or bacteria, for use in any of the disclosed methods may be derived from any source. A sample can be an environmental sample, which includes samples collected from natural environments (e.g. a lake, a pond, soil, outdoor air), and artificial environments (e.g. a clean room, a spacecraft, a hospital facility, a food production facility, a neutraceutical or pharmaceutical facility, or a laboratory facility). In some embodiments, the sample is a food product, a neutraceutical product, a pharmaceutical product, a water sample, a soil sample, or a sample collected from a mammal. A sample can also be any sample obtained from a subject. Non-limiting examples of samples obtained from a subject include skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues. Subjects include, but are not limited to, murines, simians, humans, farm animals, sport animals, and pets. In some embodiments, the subject is a human.

Figure 8:
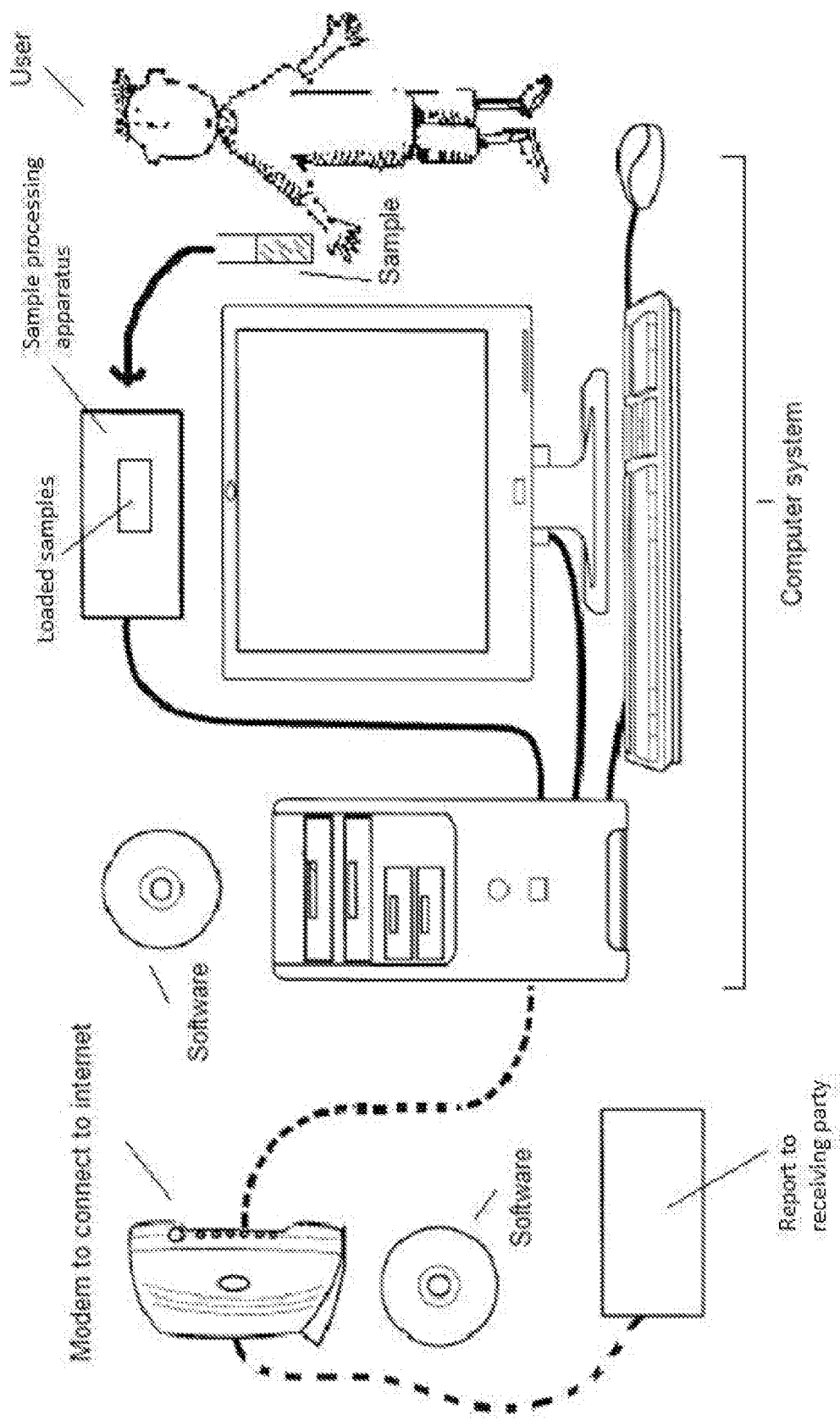
FIG. 8 illustrates a non-limiting example of a computer system useful in the methods of the invention.

In some embodiments of any aspect of the invention, a computer system is used to execute one or more steps of the described methods. FIG. 8 illustrates a non-limiting example of a computer system useful in methods of the invention. In some embodiments, the computer system is integrated into and is part of a sample processing apparatus, like a liquid handler, nucleic acid amplification system, flow cytometer, cell imager, and/or a sequencing system (e.g. an Illumina Genome Analyzer, HiSeq, or MiSeq system). In some embodiments, the computer system is connected to or ported to an analysis system. In some embodiments, the computer system is connected to an analysis system by a network connection. A computer system (or digital device) may be used to receive and store results, analyze the results, and/or produce a report of the results and analysis. The computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, a health care provider, a health care manager, or electronic system (e.g. one or more computers, and/or one or more servers). In some embodiments, a computer-readable medium includes a medium suitable for transmission of a result of an analysis of a biological sample. The medium can include a result regarding analysis of an individual's genetic profile, wherein such a result is derived using the methods described herein. The data and or results may be displayed at any time on a display, such as a monitor, and may also be stored or printed in the form of a genetic report.

In one aspect, the disclosure provides a nucleic acid probe comprising a polynucleotide joined to a compound. In some embodiments, the compound comprises (i) a nucleic acid binding moiety, (ii) a detectable label, and (iii) an activatable group that covalently bonds to a target polynucleotide when exposed to a linking agent. Where the activatable group is a chemically activatable group, activation may comprise exposing the compound to a chemical agent, and optimal temperature, an optimal pH, or a combination of these. Where the activatable group is a photoreactive group, activation may comprise exposure to a suitable light source for a time sufficient to cause covalent modification of a nucleic acid by the compound. In some embodiments, the light is visible light, which may be from a natural or artificial source. For example, the light source can be an LED light, preferably with an output wavelength from 300 nm to about 600 nm, more preferably from 450 nm to 500 nm. The duration of activation, such as by exposure to light, can be for any suitable duration, such as from about 30 seconds to about 30 minutes. In some embodiments, the light exposure time is from about 5 minutes to about 20 minutes, or about 1 to 15 minutes. After activation, excess compound may optionally be removed, such as by washing, centrifugation, gel electrophoresis, ultra-membrane filtration, column chromatography, or a combination of one or more of these. In some embodiments, the steps of contacting, activating, and removing excess compound are repeated one or more times (e.g. 1, 2, 3, 4, 5, 6, 7, 8, 9, 10, or more times) to obtain an optimal degree of nucleic acid modification. For example, an optimal degree of modification can be one such that the modified nucleic acid comprises a maximum number of compound molecules without substantially compromising the ability of the nucleic acid to hybridize with a target nucleic acid. For example, binding strength or specificity to a complementary nucleic acid is reduced by no more than 25%, 10%, 5%, 1%, or less as a result of modification, as compared to a comparable unmodified nucleic acid. In some embodiments, the linking agent is visible light. In some embodiments, the compound is a compound of Formula A. In some embodiments, the compound is a compound of Formula A'.

A probe in accordance with the disclosure may comprise DNA, RNA, modified nucleotides (e.g. methylated or labeled nucleotides), modified backbone chemistries (e.g. morpholine ring-containing backbones), nucleotide analogs, or combinations of two or more of these. The nucleic acid probe can be of any suitable length. In some embodiments, a nucleic acid probe is about or more than about 5, 10, 15, 20, 25, 30, 35, 40, 45, 50, 60, 70, 80, 90, 100, 500 or more nucleotides in length. The nucleotide sequence of the probe can be any sequence having sufficient complementarity to a nucleic acid sequence in a biological sample to allow for hybridization of the probe to the target nucleic acid in the biological sample under a desired hybridization condition. Ideally, the probe will hybridize only to the nucleic acid target of interest in the sample and will not bind non-specifically to other non-complementary nucleic acids in the sample or other regions of the target nucleic acid in the sample. The hybridization conditions can be varied according to the degree of stringency desired in the hybridization reaction. For example, if the hybridization conditions are for high stringency, the probe will bind only to the nucleic acid sequences in the sample with which it has a very high degree of complementarity. Low stringency hybridization conditions will allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type, and target. The unlabeld nucleic acid probe can be commercially obtained or can be synthesized according to standard nucleotide synthesizing protocols. Alternatively, the unlabeled probe can be produced by isolation and purification, and optionally amplification, of a nucleic acid sequence from biological materials according to standard methods.

Detectable labels to which a nucleic acid probe can be linked include, but are not limited to, a hapten, biotin, digoxigenin, fluorescein isothiocyanate (FITC), Alexa Fluor dyes, Cy dyes, Atto dyes, CF dyes, HisTag, dinitrophenyl, amino methyl coumarin acetic acid, acetylaminofluorene and mercury-sulfhydryl-ligand complexes, chromogenic dyes, fluorescent dyes, ethidium bromide, SYBR green, SYBR blue, DAPI, acriflavine, fluorcoumanin, ellipticine, daunomycin, chloroquine, distamycin D, chromomycin, propidium iodine, Hoechste, SYBR gold, acridines, proflavine, acridine orange, homidium, mithramycin, ruthenium polypyridyls, anthramycin, and any other suitable label as described herein or known in the art. In some embodiments, multiple probes, each having a different target nucleic acid and a different label, are provided for hybridization to a single sample simultaneously, such as about or more than about 1, 2, 3, 4, 5, 6, 7, 8, 9, 10, 11, 12, 13, 14, 15, 16, 17, 18, 19, 20, or more different probes. The activatable group can be any suitable activatable group, including those described herein.

In some embodiments, the compound comprises a functional group capable of forming a covalent linkage with a detectable label. For example, M of Formula A or Formula A' may comprise such a functional group. The functional group can be a chemical moiety that is chemically compatible with the activatable group of the compound and is capable of forming a covalent linkage with a detectable label. Non-limiting examples of a suitable functional group can include a primary or secondary amine, a CLICK chemistry reaction partner (e.g., an azido or alkyne), an aldehyde, a hydrazine or an aminooxy, for example. In some embodiments, the detectable label comprises a reactive group that is compatible with the functional group. The reactive group and the functional group are typically an electrophile and a nucleophile, respectively, that can form a covalent bond. According to one alternative, the reactive group is a photoactivatable group capable of reacting with a hydrocarbon molecule upon ultraviolet photoactivation or photolysis. According to another alternative, the reactive group is a dienophile capable of reacting with a conjugated diene via a Diels-Alder reaction. According to yet another alternative, the reactive group is a 1,3-diene capable of reacting with a dienophile. Still other reactive group/functional group pairs may be selected based on Staudinger chemistry or the reaction between an azido group and a terminal alkyne (the so-called Click chemistry). Non-limiting examples of useful reactive groups, functional groups, and corresponding linkages are described herein, such as in Table 2. A nucleic acid probe modified with the compound can be subsequently reacted with detectable label comprising a reactive group, resulting in a probe modified with a detectable label of choice.

In one aspect, the disclosure provides kits comprising one or more compositions described herein, such as one or more of the compounds of the present disclosure, and/or one or more nucleic acid probes. Kits may include two or more compounds disclosed herein (e.g. 2, 3, 4, 5, 6, 7, 8, 9, 10, or more). Where two or more compounds are provided, each may comprise the same or different detectable label. Kits include, for example, kits for labeling FISH probes. Elements of the kit can be provided in any amount and/or combination (such as in the same kit or same container). The kits may further comprise additional agents for use according to methods disclosed herein, such as a buffer for the labeling reaction, a purification device, and/or an instruction manual. The kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reactions, may be obtained.

In one aspect, the disclosure provides a method of labeling a target polynucleotide. In some embodiments, the method comprises: (a) contacting a sample comprising a target polynucleotide with a nucleic acid probe (e.g. a FISH probe) comprising a polynucleotide joined to a compound described herein; and (b) detecting a detectable signal indicative of hybridization between the target polynucleotide and the nucleic acid probe.

The nucleic acid probe for use in accordance with the disclosed methods can be any suitable nucleic acid probe, including but not limited to nucleic acid probes as described herein. For example, a nucleic acid probe can be about or more than about 5, 10, 15, 20, 25, 30, 35, 40, 45, 50, 60, 70, 80, 90, 100, 500, 1000, or more nucleotides in length. The nucleic acid probe may comprise one or more sequence elements. Examples of sequence elements include, but are not limited to, one or more amplification primer annealing sequences or complements thereof, one or more sequencing primer annealing sequences or complements thereof, one or more common sequences shared among multiple different oligonucleotides or subsets of different oligonucleotides, one or more restriction enzyme recognition sites, one or more target recognition sequences complementary to one or more hybridization-target polynucleotide sequences, one or more random or near-random sequences (e.g. one or more nucleotides selected at random from a set of two or more different nucleotides at one or more positions, with each of the different nucleotides selected at one or more positions represented in a pool of oligonucleotides comprising the random sequence), one or more spacers, one or more capture sequences (e.g. for hybridization with a complementary sequence that is immobilized to a surface, such as an array or a bead), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the oligonucleotide. In general, as used herein, a sequence element located "at the 3' end" includes the 3'-most nucleotide of the oligonucleotide, and a sequence element located "at the 5' end" includes the 5'-most nucleotide of the oligonucleotide. In some embodiments, a sequence element is about, less than about, or more than about 1, 2, 3, 4, 5, 6, 7, 8, 9, 10, 11, 12, 13, 14, 15, 16, 17, 18, 19, 20, 25, 30, 35, 40, 50, 100, 500, 1000, or more nucleotides in length.

In general, the nucleic acid probe is hybridizable with the target polynucleotide, or portion thereof, based on sequence complementarity therewith. Thus, according to some embodiments, contacting a sample with the nucleic acid probe under hybridization conditions localizes the nucleic acid probe and its associated label to the target polynucleotide if it is present in the sample. In some embodiments, the method further comprises detecting the presence, and optionally the location of the label. The sample is expected to be substantially not associated with the label if the target polynucleotide is absent (e.g. after contacting and washing to remove excess label), but associated with the label if the target polynucleotide is present. Accordingly, detecting the presence of the label is indicative of the presence of the target polynucleotide in the sample. In some embodiments, detection identifies the location of the target polynucleotide relative to a second component of the sample, such as a particular cell or cell type, an organelle (e.g. enodplasmic reticulum, golgi apparatus, endosome, ribosome, nucleus, nuclear envelope, cell membrane, mitochondrion, etc.), a chromosome or relative position on a chromosome (e.g. in relation to a second nucleic acid probe), a particular protein (e.g. a particular enzyme, receptor, complex, or transcription factor), or another nucleic acid (e.g. a second target polynucleotide). Typically, the location of the second component is identified by the presence of a second label specific for that particular component. The precise composition comprising the second label and mode of detection will depend on the particular target, binding moiety, and label selected. Examples of these are provided herein.

In one aspect, the disclosure provides a method of preparing a nucleic acid probe. In some embodiments, the method comprises contacting a nucleic acid probe with a compound of Formula A to form a mixture, and exposing the mixture to a linking agent to effect conjugation between the nucleic acid probe and the compound. The compound of Formula A may be any such compound described herein, including a compound of Formula A'. The composition of the nucleic acid probe can vary depending on the probe target and mode of detection, examples of which are described herein. Where the activatable group is a chemically activatable group, activation may comprise exposing the compound to a chemical agent, and optimal temperature, an optimal pH, or a combination of these. Where the activatable group is a photoreactive group, activation may comprise exposure to a suitable light source for a time sufficient to cause covalent modification of a nucleic acid probe by the compound. In some embodiments, the light is visible light, which may be from a natural or artificial source. For example, the light source can be an LED light, preferably with an output wavelength from 300 nm to about 600 nm, more preferably from 450 nm to 500 nm. The duration of activation, such as by exposure to light, can be for any suitable duration, such as from about 30 seconds to about 30 minutes. In some embodiments, the light exposure time is from about 5 minutes to about 20 minutes, or about 1 to 15 minutes. After activation, excess compound may optionally be removed, such as by washing, centrifugation, gel electrophoresis, ultra-membrane filtration, column chromatography, or a combination of one or more of these. In some embodiments, the steps of contacting, activating, and removing excess compound are repeated one or more times (e.g. 1, 2, 3, 4, 5, 6, 7, 8, 9, 10, or more times) to obtain an optimal degree of nucleic acid modification. For example, an optimal degree of modification can be one such that the modified nucleic acid comprises a maximum number of compound molecules without substantially compromising the ability of the nucleic acid to hybridize with a target nucleic acid. For example, binding strength or specificity to a complementary nucleic acid is reduced by no more than 25%, 10%, 5%, 1%, or less as a result of modification, as compared to a comparable unmodified nucleic acid. In some embodiments, the linking agent is visible light. In some embodiments, the compound is a compound of Formula A. In some embodiments, the compound is a compound of Formula A'. In preferred embodiments of this aspect of the disclosure, M of Formula A is a label, such as a label described herein.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Preparation of Compound No. 1

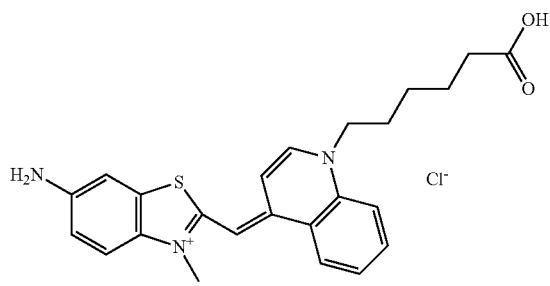

Compound No. 1

A mixture of nitro-thiazole orange (3 g, 6.6 mmol) (prepared according to U.S. Pat. No. 6,541,618) was hydrogenated in the presence of 10% Pd/C in MeOH and hydrogen (35 psi). The mixture was suction filtered through a Celite pad. The filtrate was concentrated to dryness in vacuo and the residue was purified by column chromatography on silica gel to give a dark orange solid (1.8 g)

Example 2

Preparation of Compound No. 2

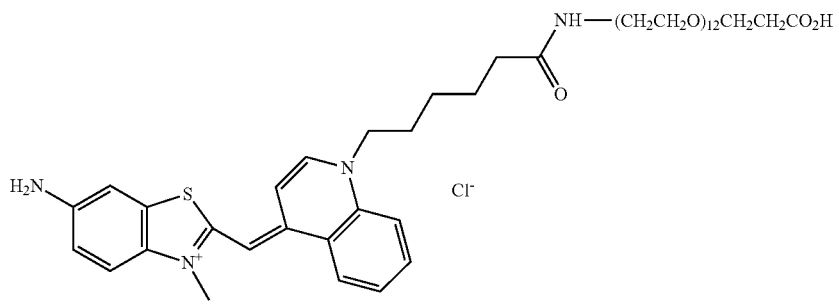

Compound No. 2

To a solution of Compound No. 1 (0.5 g, 1.1 mmol) in DMF (10 mL) was added $Et_3N$ (0.76 mL, 5.5 mmol) and TSTU (0.33 g, 1.1 mmol). The mixture was stirred at room temperature for 30 minutes, followed by addition of amino-$dPEG_{12}$-acid (0.67 g, 1.1 mmol) (Quanta Biodesign, cat #: 10287) in $CHCl_3$ (5 mL). The mixture was stirred at room temperature overnight and then concentrated to dryness in vacuo. The residue was purified by column chromatography on silica gel to give a dark orange solid (0.7 g).

Example 3

Preparation of Compound No. 3

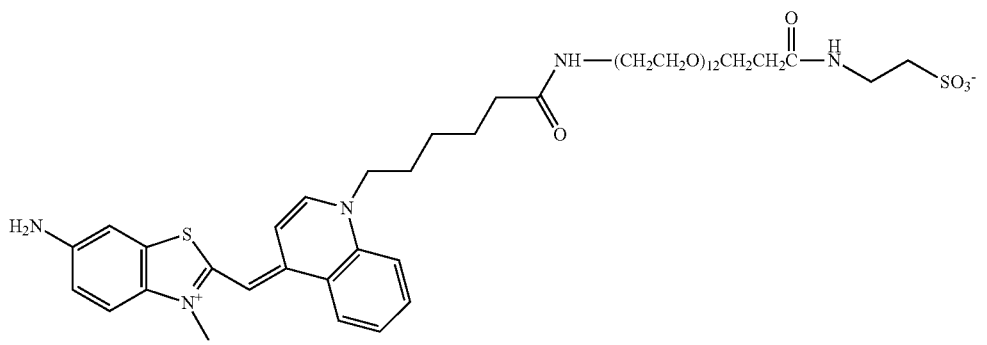

Compound No. 3

To a solution of Compound No. 2 (0.6 g, 0.56 mmol) in DMF (3 mL) was added Et$_3$N (0.4 mL, 2.8 mmol) and TSTU (0.17 g, 0.56 mmol). The mixture was stirred at room temperature for 30 minutes, followed by the addition of taurine sodium in 3 mL water (1 mmol). The mixture was stirred at room temperature overnight and then concentrated to dryness in vacuo. The residue was purified by column chromatography on silica gel to give a dark orange solid (0.35 g).

Example 4

Preparation of Compound No. 4

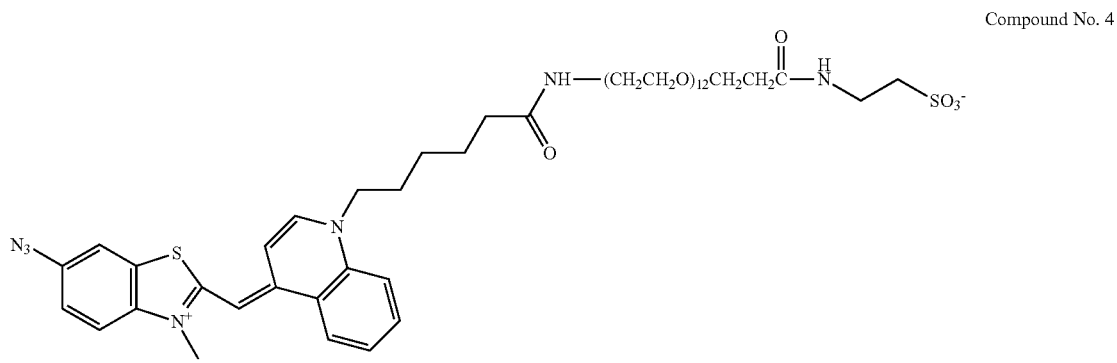

Compound No. 4

To a solution of Compound No. 3 (0.34 g, 0.3 mmol) in 5% HCl (10 mL) at −10° C. was added a solution of NaNO$_2$ (21 mg, 0.3 mmol) in H$_2$O (1 mL). The solution was stirred at −10° C. for 15 minutes, followed by the addition of NaN$_3$ (39 mg, 0.6 mmol) in H$_2$O (1 mL). The temperature was allowed to warm up slowly to room temperature and the solution was stirred at room temperature for 2 hours. The solution was concentrated to dryness in vacuo and the residue was purified by preparative HPLC to give a red solid (55 mg).

Example 5

Preparation of Compound No. 5

Compound No. 5

To a solution of ATTO 465 succinimidyl ester (10 mg, 0.02 mmol) (Sigma, cat #: 53404) in DMF (1 mL) was added Et$_3$N (28 uL) and amino-dPEG$_4$-acid (6 mg, 0.022 mmol) (Quanta Biodesign, cat #: 10244). The mixture was stirred at room temperature overnight and then concentrated to dryness in vacuo. The residue was purified by column chromatography on silica gel to give light yellow solid (13 mg).

Example 6

Preparation of Compound No. 6

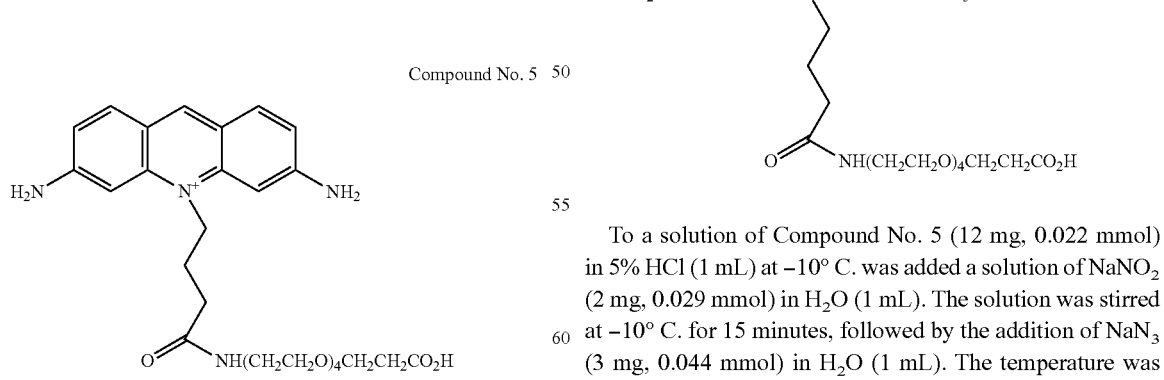

Compound No. 6

To a solution of Compound No. 5 (12 mg, 0.022 mmol) in 5% HCl (1 mL) at −10° C. was added a solution of NaNO$_2$ (2 mg, 0.029 mmol) in H$_2$O (1 mL). The solution was stirred at −10° C. for 15 minutes, followed by the addition of NaN$_3$ (3 mg, 0.044 mmol) in H$_2$O (1 mL). The temperature was allowed to warm up slowly to room temperature and the solution was stirred at room temperature for 2 hours. The solution was concentrated to dryness in vacuo and the residue was purified by preparative HPLC to give a pale yellow solid (5.5 mg).

Example 7

Preparation of Compound No. 7

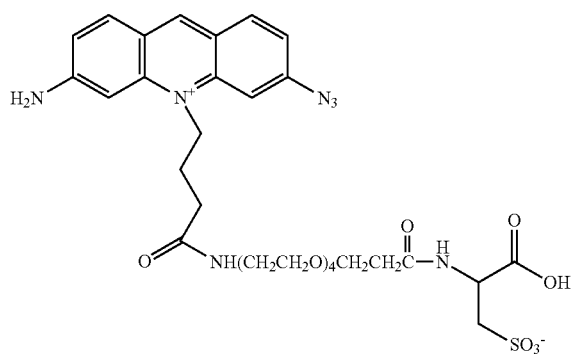

Compound No. 7

To a solution of Compound No. 6 (5 mg, 0.009 mmol) in DMF (0.5 mL) was added Et$_3$N (6 uL) and TSTU (3 mg, 0.01 mmol). The mixture was stirred at room temperature for 15 minutes and then added to a pre-cooled solution of L-cysteic acid (16 mg, 0.09 mmol) and Et$_3$N (110 uL) in H$_2$O (1 mL). The mixture was stirred at room temperature for 2 hours and then concentrated to dryness in vacuo. The residue was purified by preparative HPLC to give a light yellow solid (3 mg).

Example 8

Preparation of Compounds 8 and 9

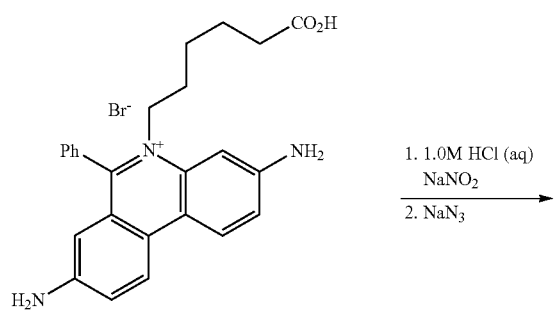

5-(5-carboxypentyl)-3,6-diamino-6-phenylphenanthridium, bromide

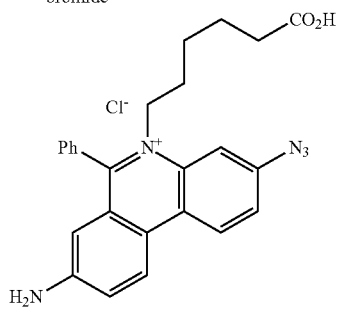

8

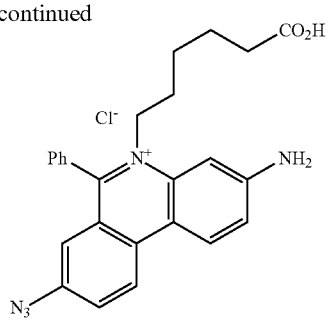

9

5-(5-Carboxypentyl)-3,6-diamino-6-phenylphenanthridium, bromide (see e.g. U.S. Pat. No. 8,232,050, 10.0 g, 20.8 mmol) was dissolved in aqueous HCl (1.0 M, 280 mL) and cooled to 0° C. A solution of sodium nitrite (1.63 g, 22.88 mmol) in water (10 mL) was added dropwise while maintaining the temperature of the reaction below 5° C. The reaction was allowed to stir for 30 minutes at 0° C. after the addition. A solution of sodium azide (1.63 g, 22.88 mmol) in water (10 mL) was added dropwise while maintaining the temperature of the reaction below 5° C. The reaction was allowed to warm to room temperature and stir for 16 hours. The reaction was neutralized with aqueous NaOH (5.0 M, ~56 mL) and concentrated. Compounds 8 and 9 were initially purified by silica gel chromatography (chloroform/methanol) and further purified by preparative HPLC (C18 column).

Example 9

Preparation of Compounds 10a and 10b

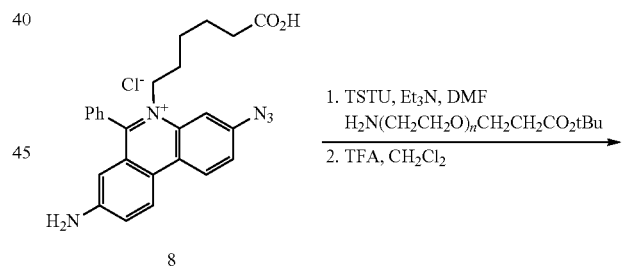

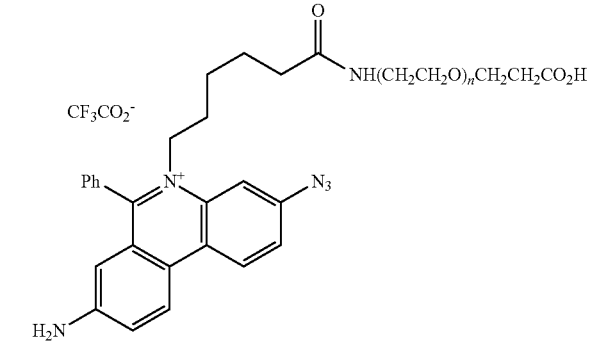

10a, n = 4
10b, n = 12

Compound 8 (1.0 g, 1.97 mmol) was dissolved in DMF (25 mL) and Et$_3$N (1.37 mL, 9.87 mmol) and cooled to 0° C. Then TSTU (593 mg, 1.97 mmol) was added and the reaction was stirred at 0° C. for 30 minutes. A solution of the appropriate pegylated amine (2.07 mmol) in chloroform (10 mL) was added dropwise at 0° C. and the reaction was allowed to warm to room temperature and stir for 12 hours. The reaction was concentrated and the t-Bu ester of 10a/10b was purified by silica gel chromatography (acetonitrile/methanol). The purified t-Bu ester of 10a/10b was dissolved in dichloromethane (20 mL) and TFA (5 mL) was added at 0° C. The reaction was stirred at room temperature overnight. The reaction was concentrated and dried under reduced pressure to give pure 10a/10b.

Example 10

Preparation of Compound 014

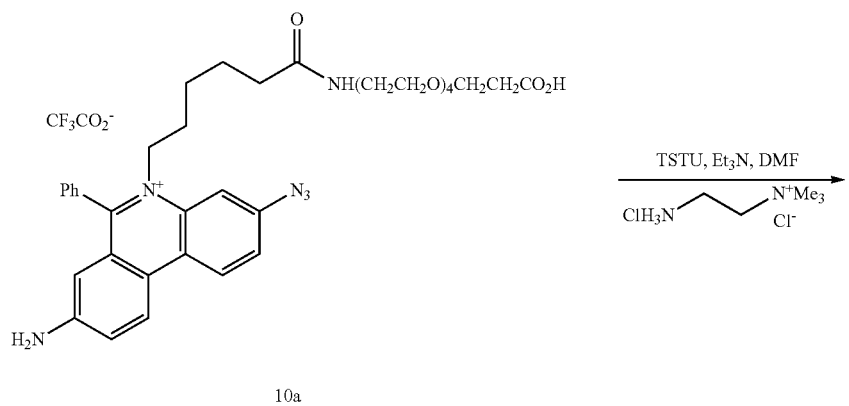

10a

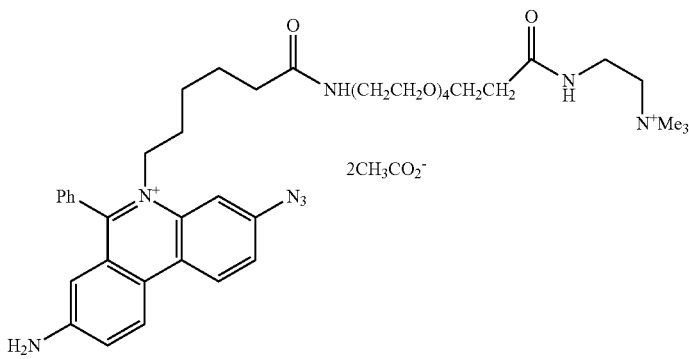

014

Compound 10a (50 mg, 0.065 mmol) was dissolved in DMF (1.5 mL) and Et₃N (46 uL, 0.33 mmol) and cooled to 0° C. Then TSTU (20 mg, 0.066 mmol) was added and the reaction was stirred at 0° C. for 30 minutes. Then (2-aminoethyl)trimethylammonium chloride hydrochloride (0.073 mmol, 12.8 mg) was added at 0° C. and the reaction was allowed to warm to room temperature and stir for 12 hours. The reaction was concentrated and 014 was purified by HPLC using triethylammonium acetate buffer as eluent. The collected fractions were pooled and then lyophilized to give 014.

Example 11

Preparation of Compound 020

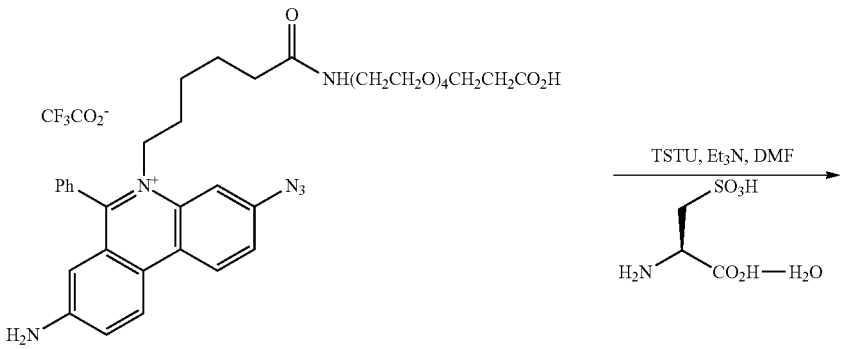

10a

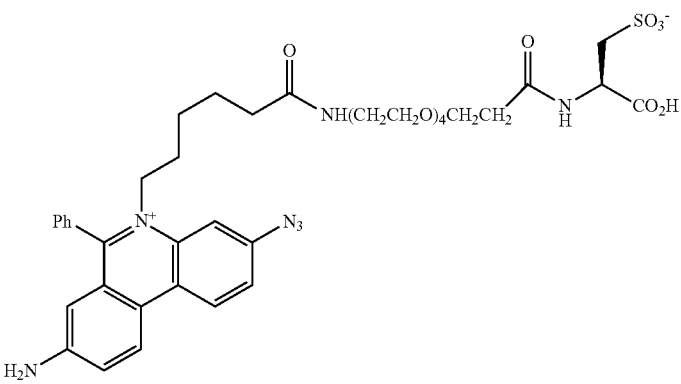

020

Compound 10a (50 mg, 0.065 mmol) was dissolved in DMF (1.5 mL) and Et₃N (46 uL, 0.33 mmol) and cooled to 0° C. Then TSTU (20 mg, 0.066 mmol) was added and the reaction was stirred at 0° C. for 30 minutes. Then L-cysteic acid monohydrate (0.073 mmol, 13.7 mg) was added at 0° C. and the reaction was allowed to warm to room temperature and stir for 12 hours. The reaction was concentrated and 020 was purified by preparative HPLC (C18 column).

Example 12

Preparation of Compound 12

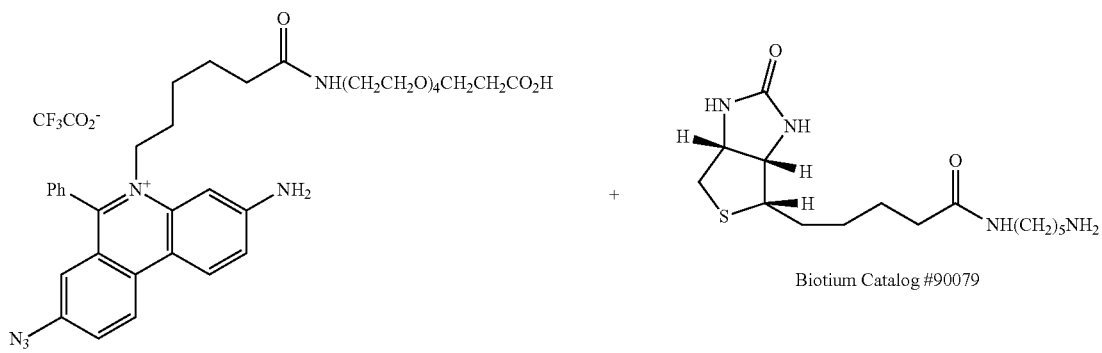

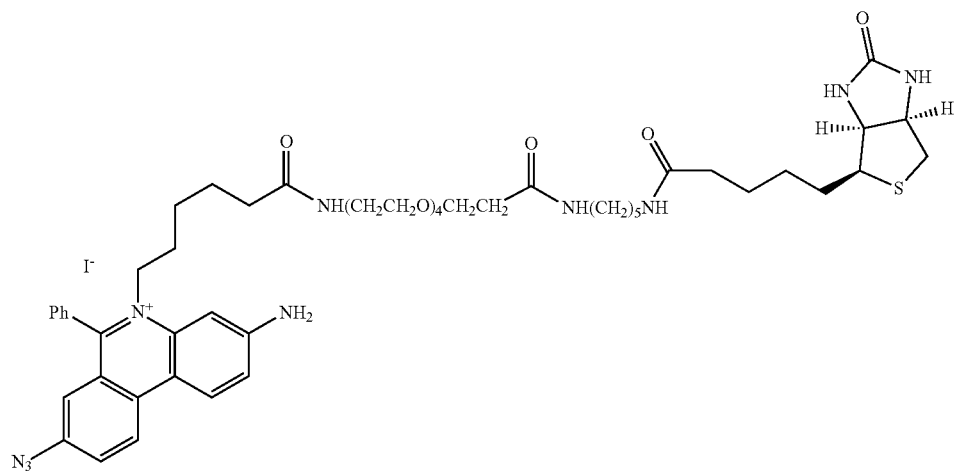

Compound 10b (50 mg, 0.066 mmol) was dissolved in DMF (1.5 mL) and Et₃N (46 uL, 0.33 mmol) and cooled to 0° C. Then TSTU (20 mg, 0.066 mmol) was added and the reaction was stirred at 0° C. for 30 minutes. Then biotin cadaverine, free base (0.073 mmol, 24.0 mg) was added at 0° C. and the reaction was allowed to warm to room temperature and stir for 12 hours. The reaction solution was added to a NaI (100 mg) in water (10 mL) to precipitate out the product. The product was collected by suction filtration and was purified by silica gel chromatography (chloroform/methanol).

Example 13

Preparation of Compound 104.1

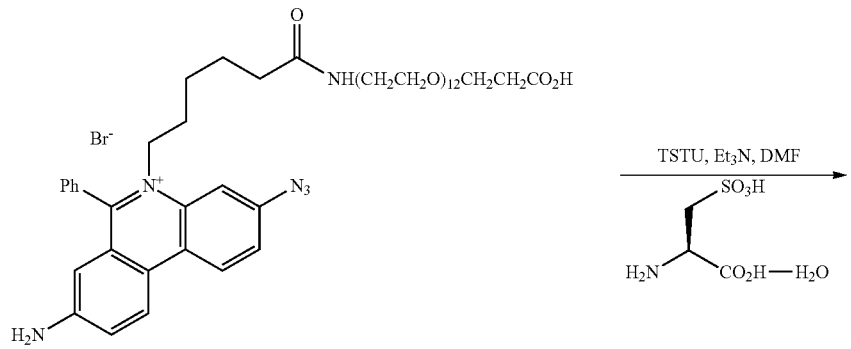

10b

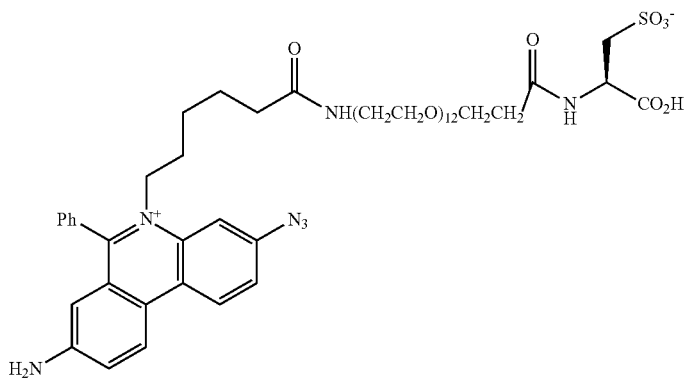

104.1

Compound 10b (73 mg, 0.066 mmol) was dissolved in DMF (1.5 mL) and Et₃N (46 uL, 0.33 mmol) and cooled to 0° C. Then TSTU (20 mg, 0.066 mmol) was added and the reaction was stirred at 0° C. for 30 minutes. Then L-cysteic acid monohydrate (0.073 mmol, 13.7 mg) was added at 0° C. and the reaction was allowed to warm to room temperature and stir for 12 hours. The reaction was concentrated and 104.1 was purified by preparative HPLC (C18 column).

Example 14

Preparation of Compound 13

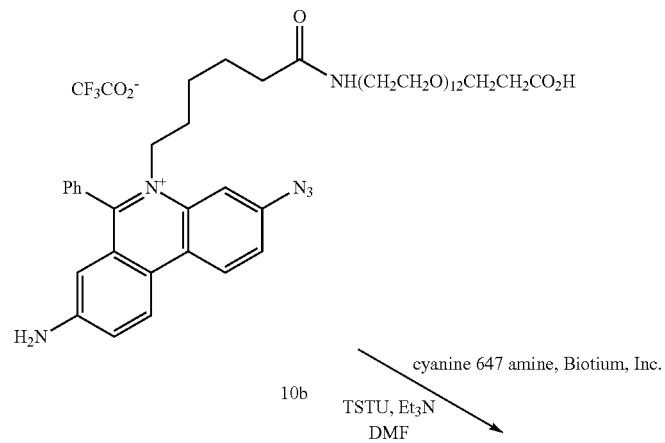

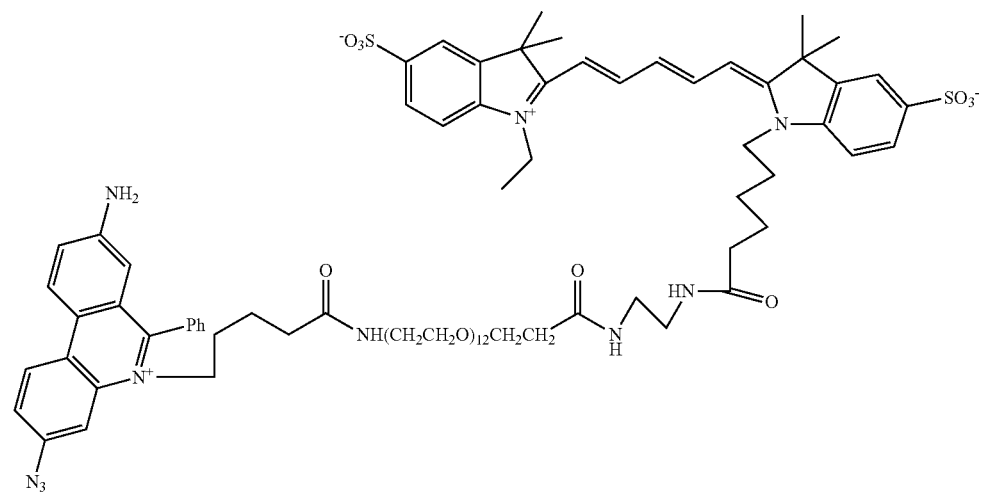

Compound 10b (3.3 mg, 3.0 umol) was dissolved in DMF (0.3 mL) and Et$_3$N (4.3 uL, 30.6 umol) and cooled to 0° C. Then a solution of TSTU (0.9 mg, 3.0 umol) in DMF (0.1 mL) was added and the reaction was stirred at 0° C. for 30 minutes. Then Cynanine5 amine (3.06 umol, 2.0 mg) was added at 0° C. and the reaction was allowed to warm to room temperature and stir for 12 hours. The reaction was concentrated and 13 was purified by silica gel chromatography (chloroform/methanol).

Example 15

Synthesis of Compound 15

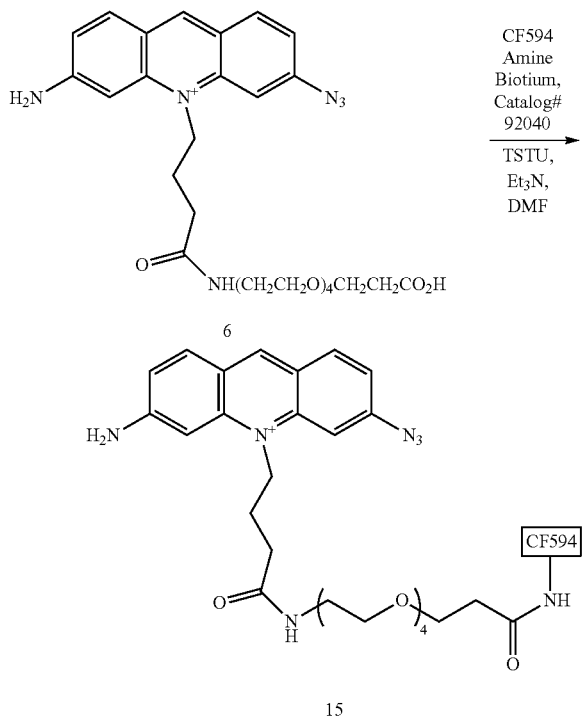

Compound 6 (3.0 umol) was dissolved in DMF (0.3 mL) and Et$_3$N (4.3 uL, 30.6 umol) and cooled to 0° C. Then a solution of TSTU (0.9 mg, 3.0 umol) in DMF (0.1 mL) was added and the reaction was stirred at 0° C. for 30 minutes. Then CF594 amine (3.1 umol) was added at 0° C. and the reaction was allowed to warm to room temperature and stir for 12 hours. The reaction was concentrated and 15 was purified by preparative HPLC (C18 column).

Example 16

Selectivity of Compounds in Cultured Cells

*Escherichia coli*, *Salmonella enterica*, and *Bacillus subtilis* were cultured in tryptic soy broth (TSB). *Staphylococcus epidermidis* was cultured in nutrient broth (NB). Bacteria were cultured overnight at 37° C. The following day, the absorbance of the cultures at 600 nm was measured and the cultures were diluted to OD$_{600}$=1.0 in growth media. Bacteria cultures were pipetted into 1.5 mL screw-top tubes at 400 uL per tube. For dead cell samples, tubes were placed in a 95° C. heat block for 5 minutes, and then allowed to return to room temperature. PMA products (cat #40013 and 40019, Biotium) and selected compounds of the disclosure (104.1, 014, or 020, where indicated) were diluted to 2.5 mM in water, and then 8 uL was added to the bacterial culture for a final concentration of 50 uM. Cultures were incubated on a rocker in the dark at room temperature for 10 minutes, and then exposed to 470 nm wavelength light in the PMA-Lite LED device for 15 minutes. Samples were centrifuged at 5000×g for 10 minutes and the supernatant was aspirated off. DNA was then purified from bacterial pellets using the Qiagen Blood and Tissue kit and eluted in 100 uL elution buffer.

Total DNA isolated from bacteria was quantified using the AccuClear Ultra High Sensitivity dsDNA Quantitation Kit (Biotium). Briefly, the linear equation for a standard curve was calculated using the provided DNA standards, and used to calculate the concentration of the bacterial DNA.

PCR was performed using the universal primers DG74 and RW01 which amplify a 370-bp region of the 16S rDNA. Forward Primer DG74 sequence: 5'-AGG AGG TGA TCC AAC CGC A-3'. Reverse Primer RW01 sequence: 5'-AAC TGG AGG AAG GTG GGG AT-3'. The following PCR mix was prepared for each sample: 12.5 uL Fast EvaGreen Master Mix (Biotium), 1 uL 5 uM primer mix, 9.5 uL water, and 2 uL isolated bacterial DNA. The PCR reaction was performed in the Qiagen Rotor-Gene Q and was programmed as follows: 95° C., 5 min; 40 cycles of 95° C. 5 sec, 60° C. 25 sec, 72° C., acquiring fluorescence after this step. Using the Rotor-Gene Q software, normalized fluorescence and Ct values were calculated. The change in Ct (dCt) caused by a dye was calculated by subtracting the Ct of the untreated bacteria from the Ct of the dye-treated bacteria.

Live *Staphylococcus epidermidis* (a gram-positive bacteria) was either left untreated, treated with one of two versions of commercial PMA products (cat #40013 and 40019, Biotium), or treated with a compound of the present disclosure (compound 104.1, 014, or 020). Viability PCR was performed and the effect of each dye was measured by determining the dCt. The dCt was calculated by subtracting the Ct of untreated sample from dye-treated sample. Results for live *S. epidermidis* are provided in FIG. 1. The plot shows dCt on the y-axis and the dye treatment on the x-axis. The dCt values are shown above each bar. While PMA (cat #40013) causes some modification of DNA from live *S. epidermidis*, the compounds of the present disclosure caused little to none.

Figure 2:
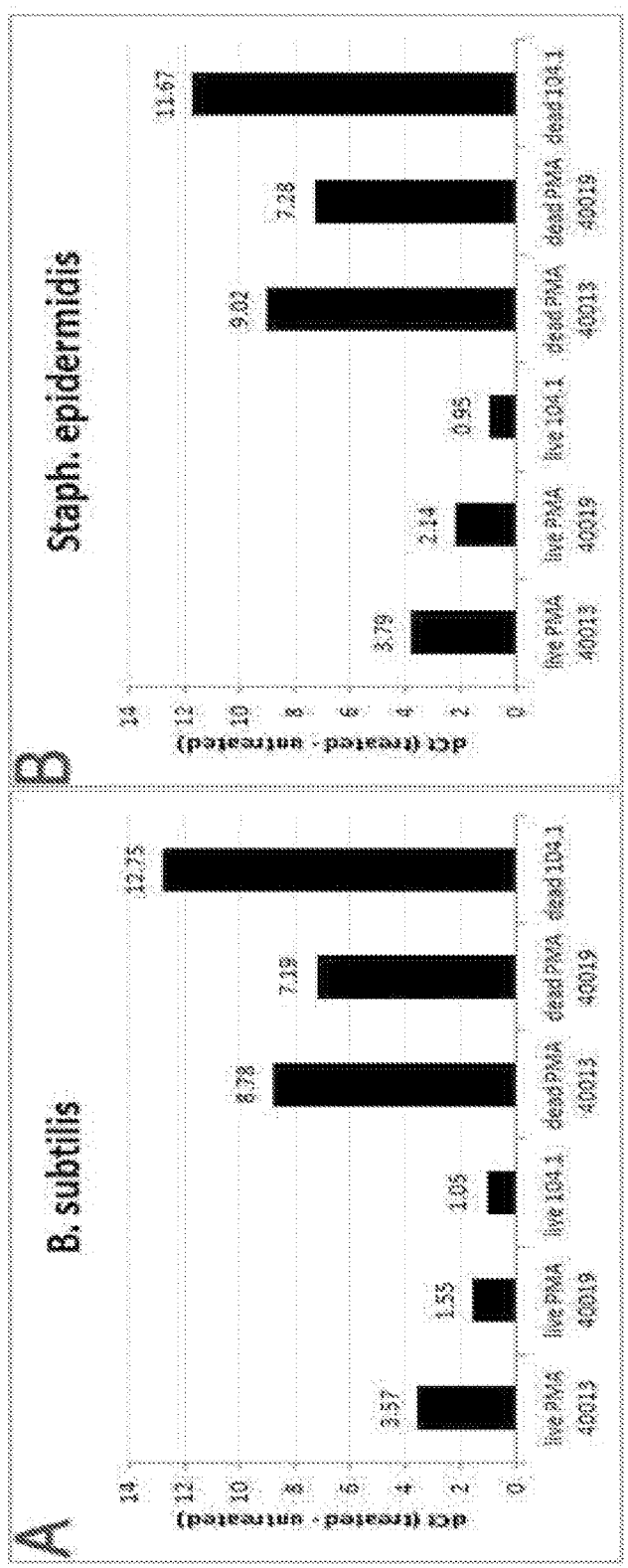
FIGS. 2A-B are graphs comparing selectivity of the indicated compounds for non-viable cells.

Live or dead *Bacillus subtilis* (FIG. 2A) or *Staphylococcus epidermidis* (FIG. 2B) were either left untreated, treated with one of two versions of commercial PMA products (cat #40013 and cat #40019, Biotium), or treated with Compound 104.1. Viability PCR was performed and the effect of each dye was measured by determining the dCt. The dCt was calculated by subtracting the Ct of untreated sample from dye-treated sample. Results are provided in FIG. 2. The plots show dCt on the y-axis and the dye treatment on the x-axis. The dCt values are shown above each bar. Compound 104.1 shows less of an effect on live cells and a greater effect on dead cells, thus demonstrating improved live/dead discrimination in gram-positive bacteria.

Figure 3:
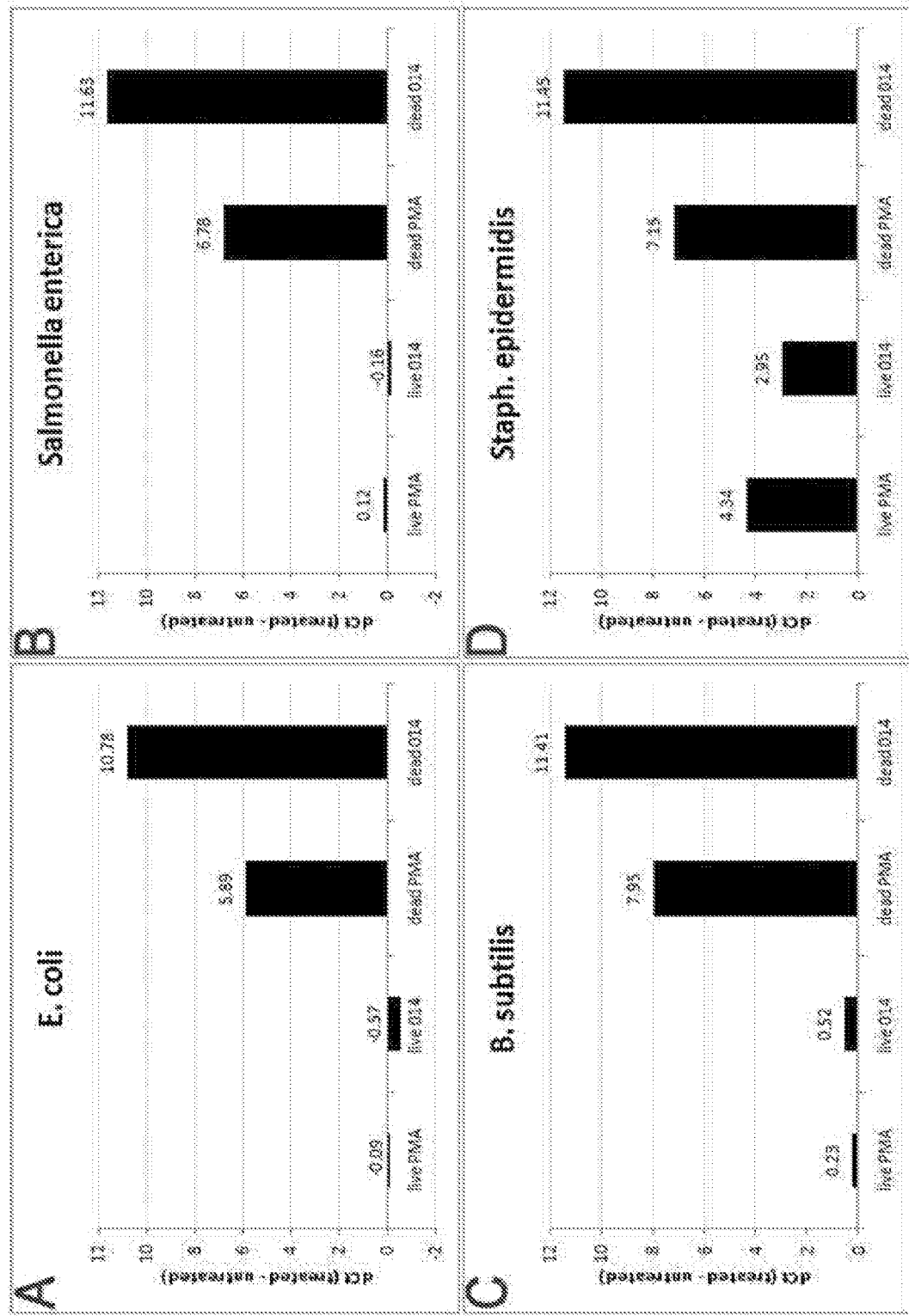
FIGS. 3A-D are graphs comparing selectivity of the indicated compounds for non-viable cells.

Live or dead *Escherichia coli* (FIG. 3A), *Salmonella enterica* (FIG. 3B), *Bacillus subtilis* (FIG. 3C) or *Staphylococcus epidermidis* (FIG. 3D) were either left untreated, treated with PMA, or treated with Compound 014. Viability PCR was performed and the effect of each dye was measured by determining the dCt. The dCt was calculated by subtracting the Ct of untreated sample from dye-treated sample. Results are provided in FIG. 3. The plots show dCt on the y-axis and the dye treatment on the x-axis. The dCt values are shown above each bar. Compound 014 had less of an effect on live cells and a greater effect on dead cells, thus demonstrating improved live/dead discrimination in both gram-positive and gram-negative bacteria.

Figure 4:
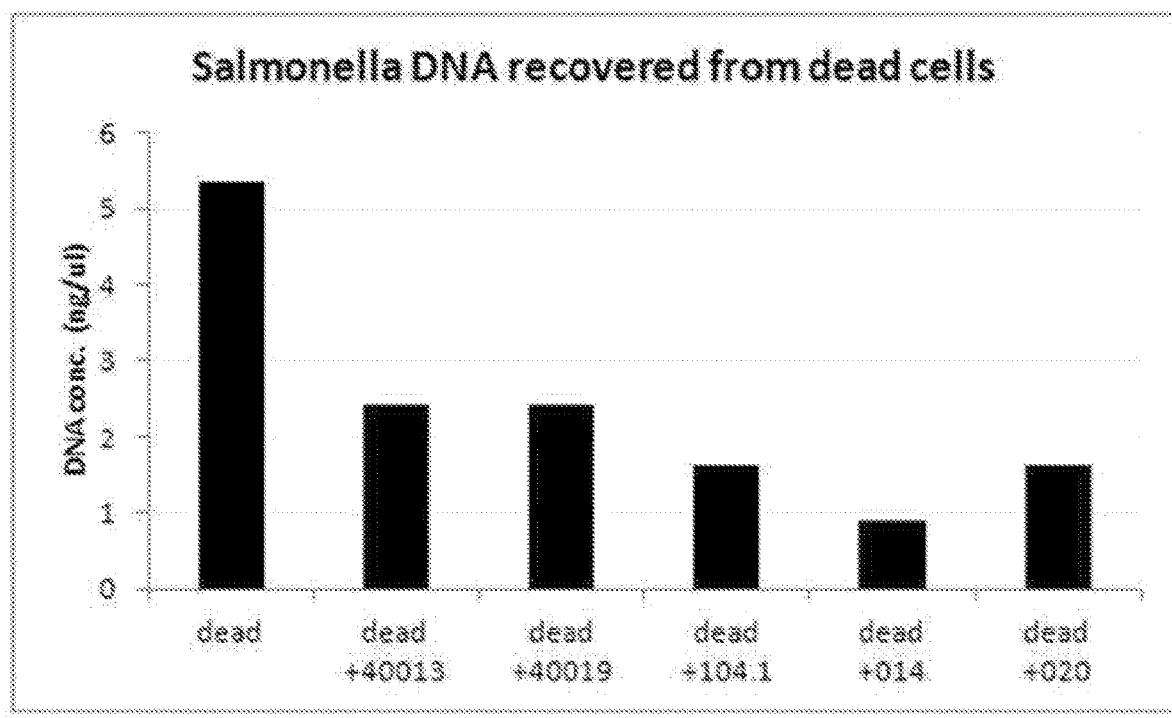
FIG. 4 is a graph comparing DNA recovery from non-viable cells treated with the indicated compounds.

Dead *Salmonella* was either left untreated, treated with one of two versions of commercial PMA products (cat #40013 and cat #40019, Biotium), or treated with a modifier of the invention (Compound 104.1, 014, or 020). The DNA from each sample was isolated and quantified. Results are provided in FIG. 4. The plot shows the concentration of DNA recovered (ng/uL) on the y-axis and the dye treatment on the x-axis. Treatment with compound 104.1 results in less recovered DNA from non-viable cells than treatment with PMA.

Example 17

Selectivity of Compounds in Cells Collected by Swabbing

Figure 5:
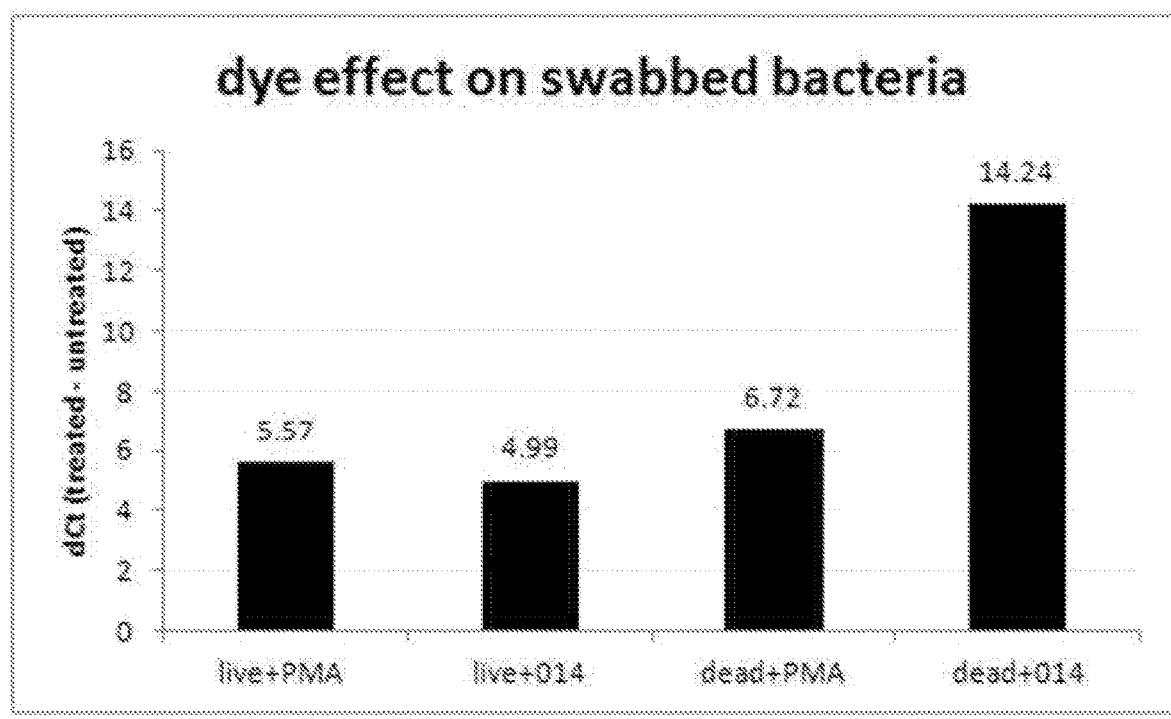
FIG. 5 is a graph comparing selectivity of the indicated compounds for non-viable cells collected by swabbing.

As in Example 16, *Staphylococcus epidermidis* was cultured in nutrient broth (NB) overnight at 37° C. The following day, the absorbance of the cultures at 600 nm was measured and the cultures were diluted to $OD_{600}=1.0$ in growth media. For dead cell samples, bacteria were placed in a 95° C. heat block for 5 minutes, and then allowed to return to room temperature. 1200 uL of live or dead bacteria were spread separately onto sterile plastic petri dishes and air-dried for four hours. To mimic a common method of bacterial sample collection, a sterile cotton swab was moistened with NB, swabbed on the plate and swirled in a tube containing 1200 uL NB. This process was repeated 3 times each for live and dead bacteria, until most of the bacteria from the plate had been transferred into the media. 400 uL of swabbed bacteria was pipetted into tubes, and either left untreated, treated with PMA dye, or treated with Compound 014, as described in Example 16. Viability PCR was performed and the effect of each dye was measured by determining the dCt. The dCt was calculated by subtracting the Ct of untreated sample from dye-treated sample. Results are shown in FIG. 5. The plot shows dCt on the y-axis and the dye treatment on the x-axis. The dCt values are shown above each bar. PMA did not function well to discriminate live and dead swabbed *S. epidermidis*, while Compound 014 showed a large difference between live and dead cells.

Example 18

Viability Staining and Mammalian Cell Culture

Jurkat cells were maintained in RPMI media supplemented with 10% fetal bovine serum, 10 mM HEPES, and 1 mM sodium pyruvate. Cells were counted and diluted to $1.0 \times 10^6$ cells/mL in growth media. Cells were pelleted by centrifugation at 350×g and resuspended in PBS. Half of the cells were heat-killed by incubation in a 56° C. water bath for 45 minutes. After they had cooled to room temperature, live and dead cells were combined in a 1:1 ratio, pelleted and washed once with PBS, and resuspended in PBS at $1.0 \times 10^6$ cells/mL. Aliquots of 1 mL were pipetted into 1.5 mL microcentrifuge tubes. Working in the dark, PMA and compound 104.1 were diluted to 1 mM in water. 1 uL of the indicated compound was added to 1 mL of cells for a final concentration of 1 uM. Cells were incubated in the dark, rocking, for 10 minutes, then exposed to light in the PMA-Lite for 15 minutes. Cells were transferred to FACS tubes and pelleted. Half of the tubes were placed at 4° C. in the dark (unfixed). For the fixed samples, cells were fixed in 2% formaldehyde for 20 minutes at ambient temperature, protected from light, then pelleted and washed with PBS, then permeabilized with 0.1% Triton X-100 for 30 minutes at ambient temperature, protected from light. Fixed and unfixed cells were pelleted and washed in FACS buffer (PBS+2% FBS) and resuspended in 500 uL FACS buffer.

Stained cells were analyzed by flow cytometry on a BD LSRII. For detection of PMA and compound 104.1 staining, samples were excited with the 488 nm laser, and the signal was detected in the PE-Texas Red channel. Flow cytometry data was analyzed using FlowJo software from TreeView.

Figure 6:
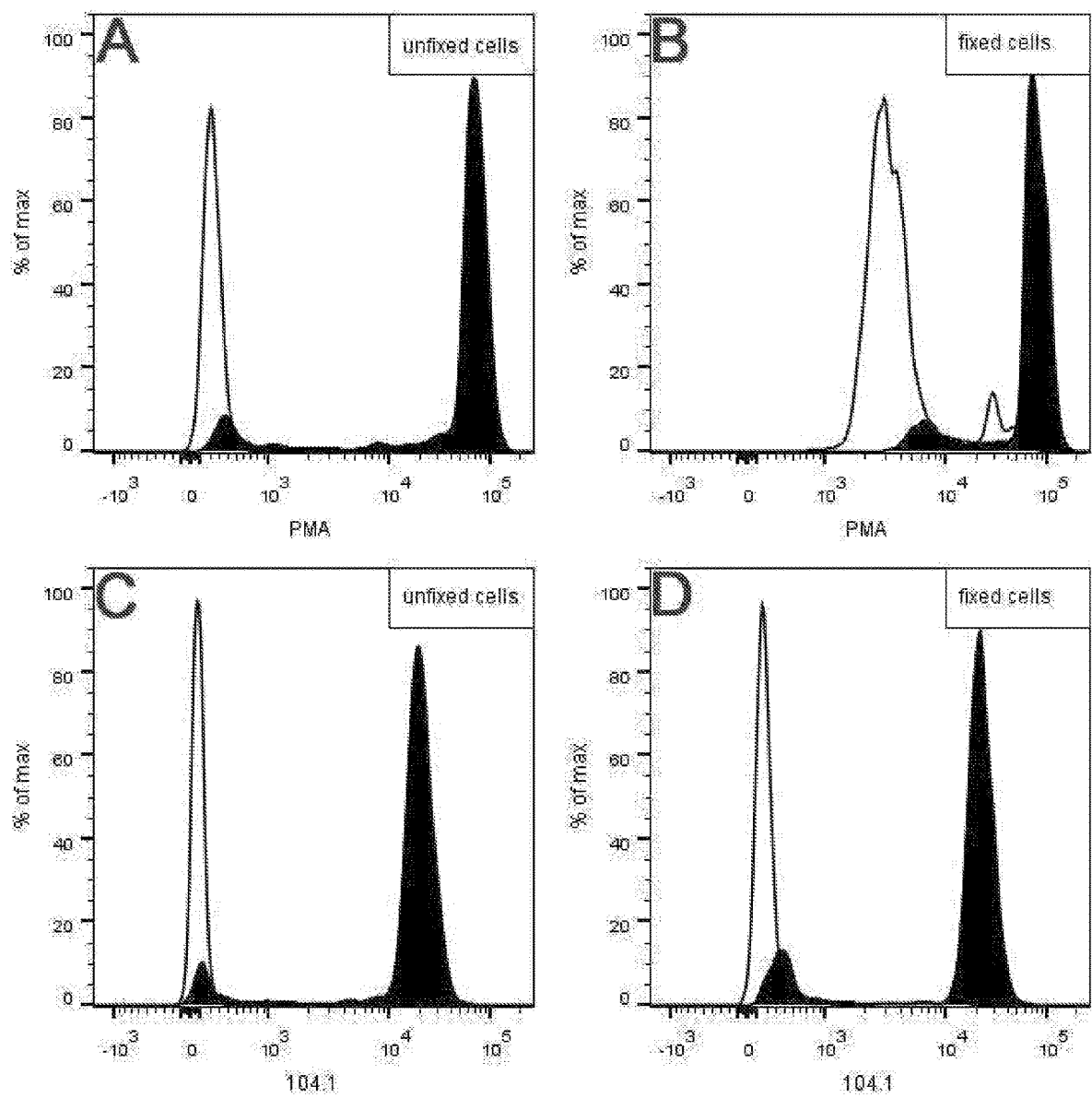
FIGS. 6A-D are plots comparing selectivity of the indicated compounds for non-viable cells.

FIG. 6 provides results for unfixed cells treated with PMA (FIG. 6A), fixed and permeabilized cells treated with PMA (FIG. 6B), unfixed cells treated with compound 104.1 (FIG. 6C), and fixed and permeabilized cells treated with compound 104.1 (FIG. 6D). The plots show an overlay of live cells (unfilled histograms) and dead cells (filled histograms). In unfixed cells, both PMA and Compound 104.1 show bright, specific staining of dead cells. After fixation, PMA shows an increase in staining of live cells (loss of specificity), while compound 104.1 maintains a high specificity for dead cells.

Example 19

Viability Staining and Microscopy

Figure 7:
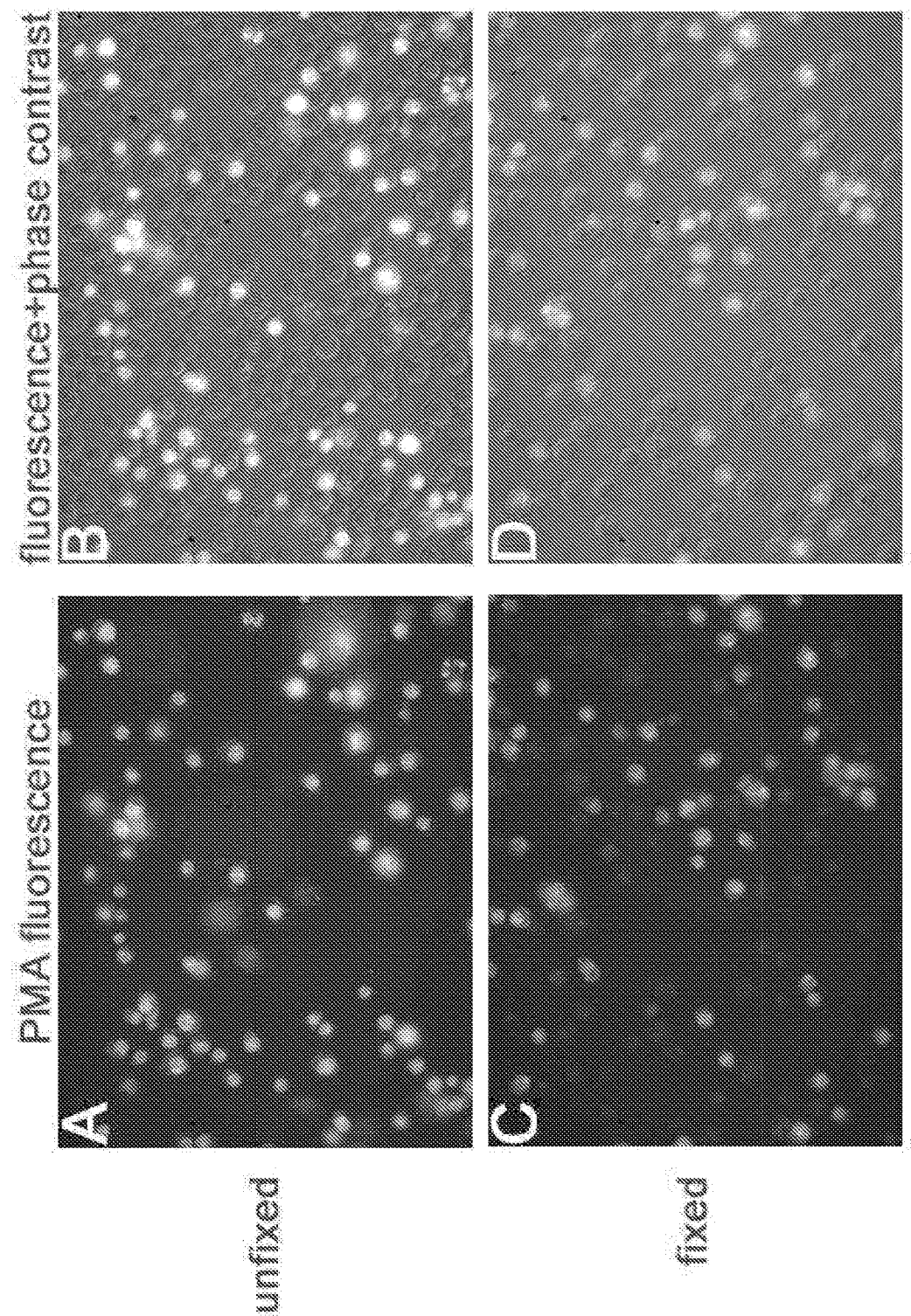
FIGS. 7A-D are microscope images illustrating selective staining of non-viable cells.

1:1 mixtures of live and heat-killed Jurkat cells were prepared and treated with PMA, as described in Example 21. The cells were transferred to a black optical bottom 96-well plate and imaged on an Olympus IX71 inverted fluorescence microscope using a Cy3 filter cube and Retiga 2000R Fast 1394 digital CCD camera with 300 msec exposure time. Imaging results are provided in FIG. 7A-D. The stained cells were either left unfixed (FIGS. 7A and B) or fixed and permeabilized (FIGS. 7C and D). Fluorescence images (FIGS. 7A and C) show stained cells, while merged fluorescence/phase contrast images (FIGS. 7B and D) show stained and unstained cells. While unfixed cells show a greater difference in fluorescence intensity between PMA-positive and PMA-negative cells, PMA staining is retained after fixation, with clear discrimination between PMA-positive and PMA-negative cells by fluorescence microscopy. The results illustrate that PMA can function as a viability dye in human cells for microscopy, and suggest that other compounds of the disclosure would have a similar functionality.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A compound having a Formula A':

$(A)_a\text{-}(M)_b$     Formula A' wherein, A is a nucleic acid binding dye of Formula C or Formula D:

Formula C

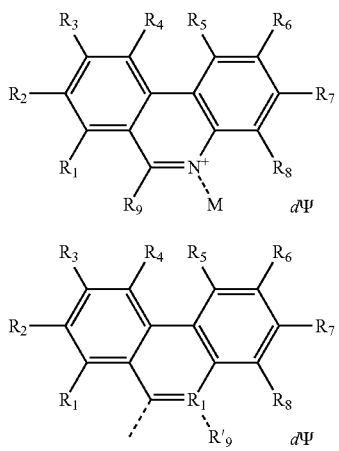

Formula D

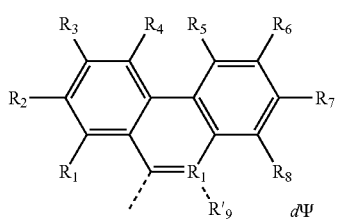

wherein the dashed line indicates the attachment site for the substituent M;

$R_1$, $R_2$, $R_3$, $R_4$, $R_5$, $R_6$, $R_7$ and $R_8$ are independently selected from the group consisting of H, F, Cl, Br, $C_1$-$C_2$ alkyl, $C_1$-$C_2$ alkoxy, amino and $C_1$-$C_2$ alkyl or dialkylamino, amidino, guanidino, and azide;

$R_9$ is a substituted or unsubstituted alkyl, substituted or unsubstituted aryl or substituted or unsubstituted heteroaryl;

$R'_9$ is a substituted or unsubstituted alkyl;

wherein at least one of $R_1$, $R_2$, $R_3$, $R_4$, $R_5$, $R_6$, $R_7$ or $R_8$ is azide (—$N_3$);

Ψ comprises a biologically compatible counter ion; and d is a number of Ψ sufficient to render overall charge of the compound neutral;

wherein A comprises an activatable group capable of crosslinking with or cleaving a target nucleic acid;

a is 1 or 2;

b is 1 or 2;

M is a substituent having a molecular mass from about 150 to about 5000 Da;

wherein M comprises at least one of the moieties selected from the group consisting of a poly(ethylene glycol) of molecular mass of at least 100 Da, a poly(propylene glycol) of molecular mass of at least 100 Da, a poly(ethylene glycol and propylene glycol) copolymer of molecular mass of at least 100 Da, a polyhydroxy moiety, a negatively charged group, and a functional group capable of forming a covalent linkage with a detectable label; and wherein the compound labels non-viable cells at a rate that is more than 200-fold higher than the rate of labeling for viable cells, for both gram-negative and gram-positive cells.

2. The compound of claim 1, wherein the activatable group is a photoaffinity label, a furan, an enediyne, a ruthenium complex, or a platinum complex.

3. The compound of claim 1, wherein the polyhydroxy moiety is a sugar, dextrin, or cyclodextrin.

4. The compound of claim 1, wherein the detectable label is fluorescent dye label, biotin, digoxigenin, or a hapten.

5. The compound of claim 1, wherein A is an azido-substituted nucleic acid binding dye.

6. The compound of claim 1, wherein M comprises (i) a poly(ethylene glycol) and (ii) a negatively charged group.

7. The compound of claim 1, having a Formula B:

A-L'-(CH$_2$CH$_2$O)$_n$-L'-B       Formula B wherein A is a nucleic acid binding dye comprising an activatable group capable of crosslinking with or cleaving a target nucleic acid;

each L' is independently a single bond or a linker comprising 1-15 atoms selected from the group consisting of C, N and 0;

n is an integer from 2-40 inclusive; and

B is a moiety comprising at least one of the moieties selected from the group consisting of a negatively charged group and a detectable label.

8. The compound of claim 7, wherein at least one L' is a linker comprising 4-10 atoms selected from the group consisting of C, N and O; and n is an integer from 2-24 inclusive.

9. The compound of claim 7, wherein each L' is independently a bond, —($C_1$-$C_{12}$ alkyl)- or —($C_1$-$C_{12}$ alkyl)-C(O)NH—.

10. The compound of claim 7, wherein B is selected from the group consisting of an amino acid, dipeptide, cysteic acid, cysteine, $C_1$-$C_{12}$ alkyl comprising an amide, $C_1$-$C_{12}$ alkyl substituted with a carboxylic acid, and $C_1$-$C_{12}$ alkyl substituted with a trialkylammonium salt.

11. The compound of claim 7, wherein B comprises a negatively charged group selected from the group consisting of —$SO_3^-$, —$CO_2^-$, and —$PO_3^{2-}$.

12. The compound of claim 7, having the structure:

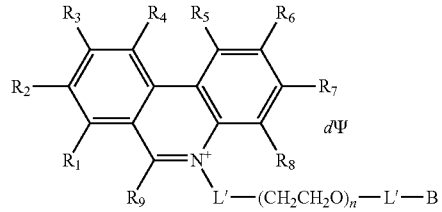

wherein $R_1$, $R_3$, $R_4$, $R_5$, $R_6$ and $R_8$ are independently H or F;

wherein at least one of $R_2$ and $R_7$ is $N_3$ and any other remaining $R_2$ and $R_7$ is $NH_2$;

$R_9$ is phenyl;

each L' is independently a single bond or a linker comprising 1-15 atoms selected from the group consisting of C, N and 0;

n is an integer from 2-40 inclusive;

B is a moiety comprising at least one of the moieties selected from the group consisting of a negatively charged group a detectable label, and a functional group capable of forming a covalent bond with a detectable label;

Ψ comprises a biologically compatible counter ion; and d is a number of Ψ sufficient to render overall charge of the compound neutral.

13. A compound having the formula:
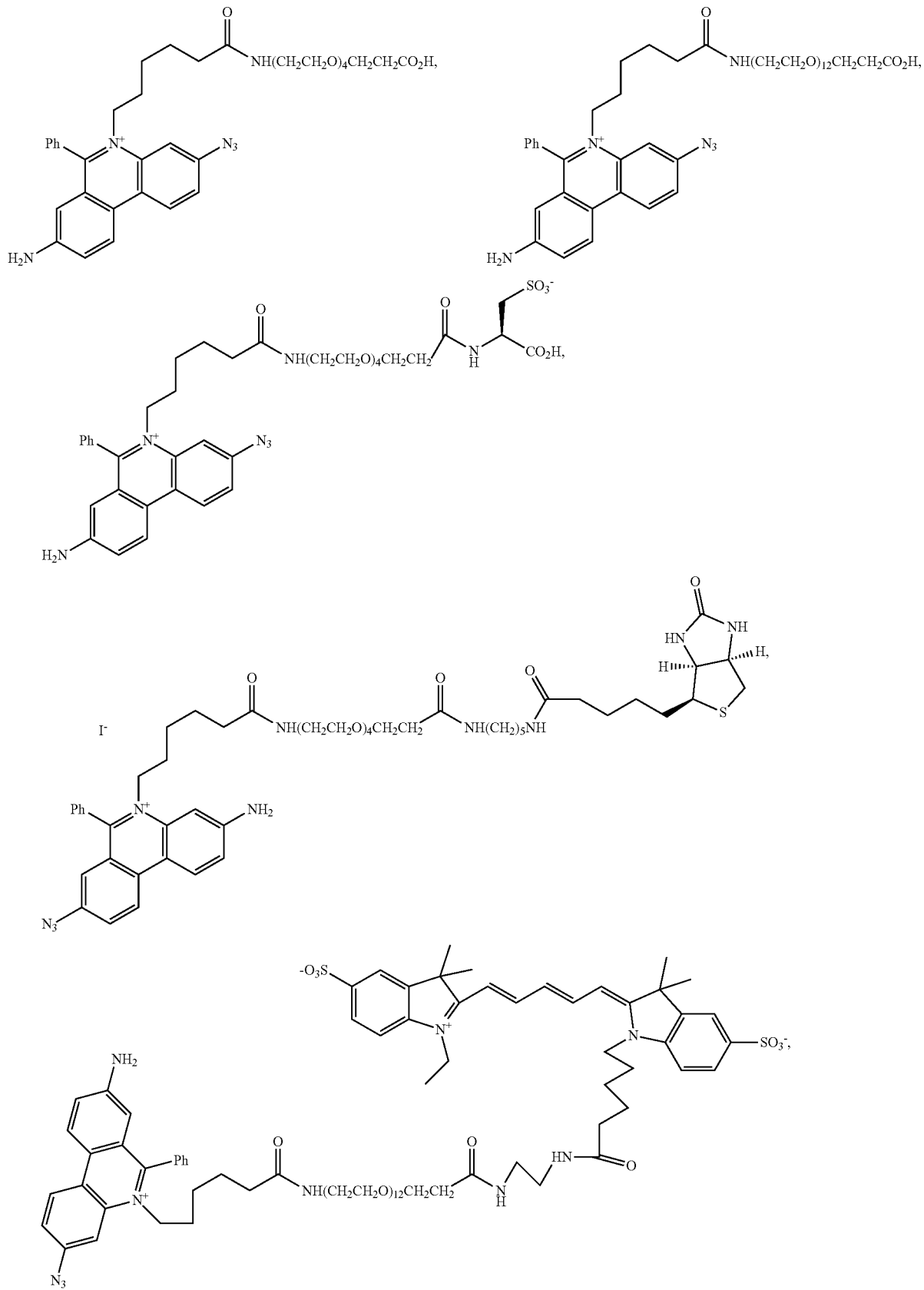

-continued
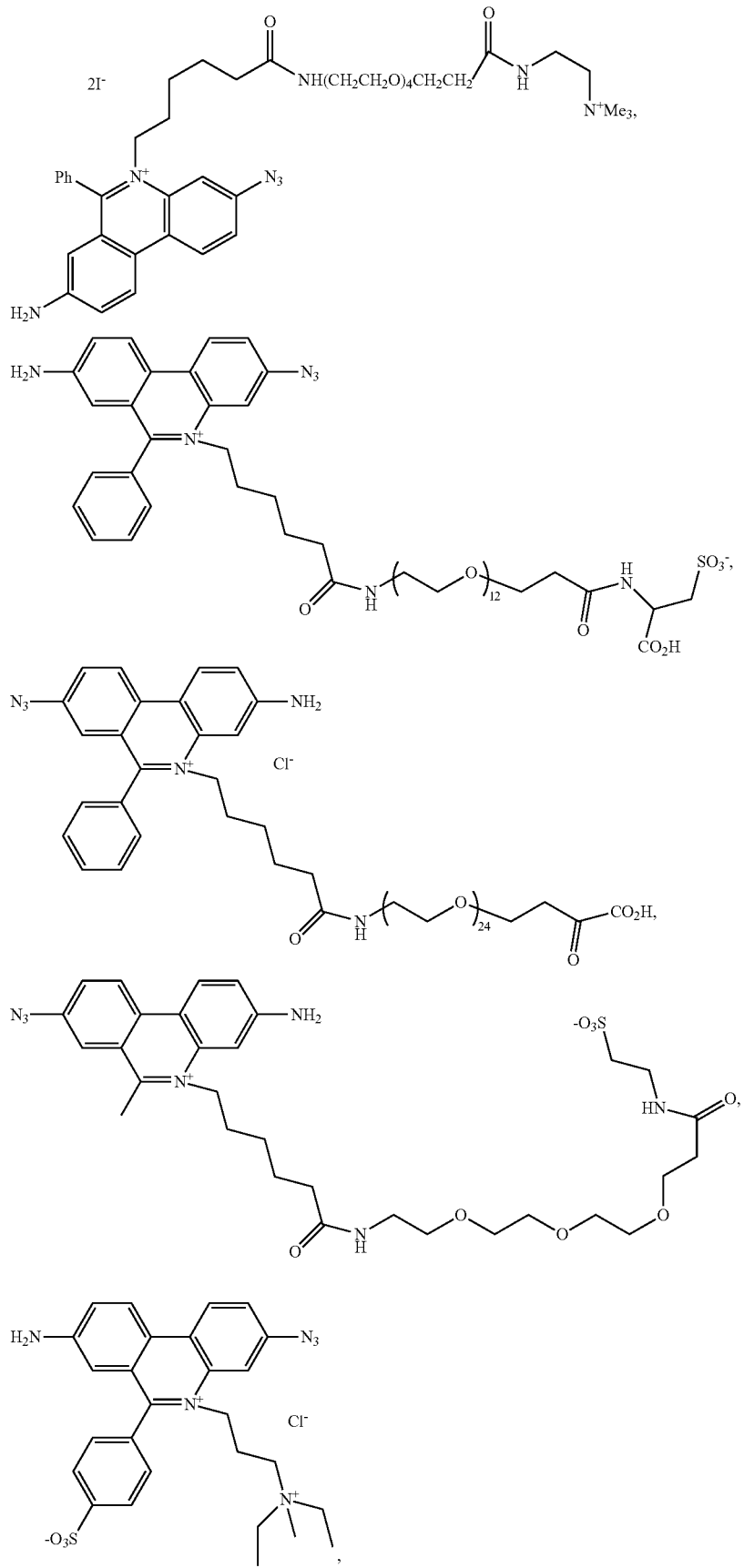

-continued
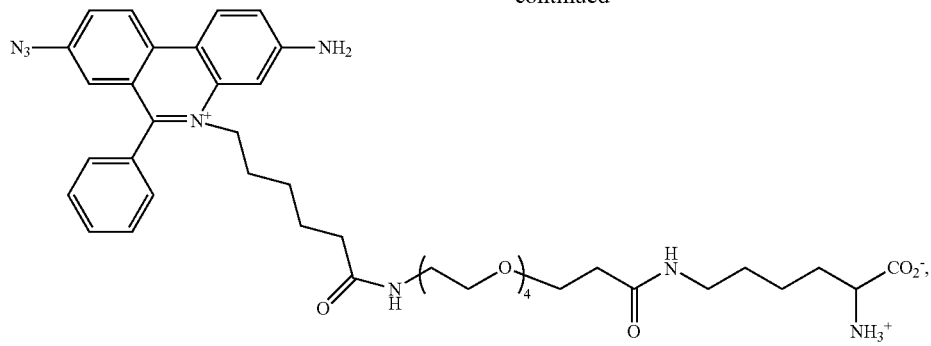
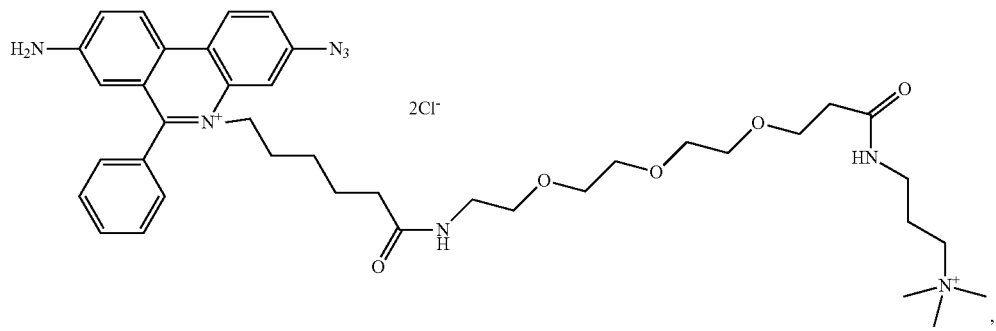
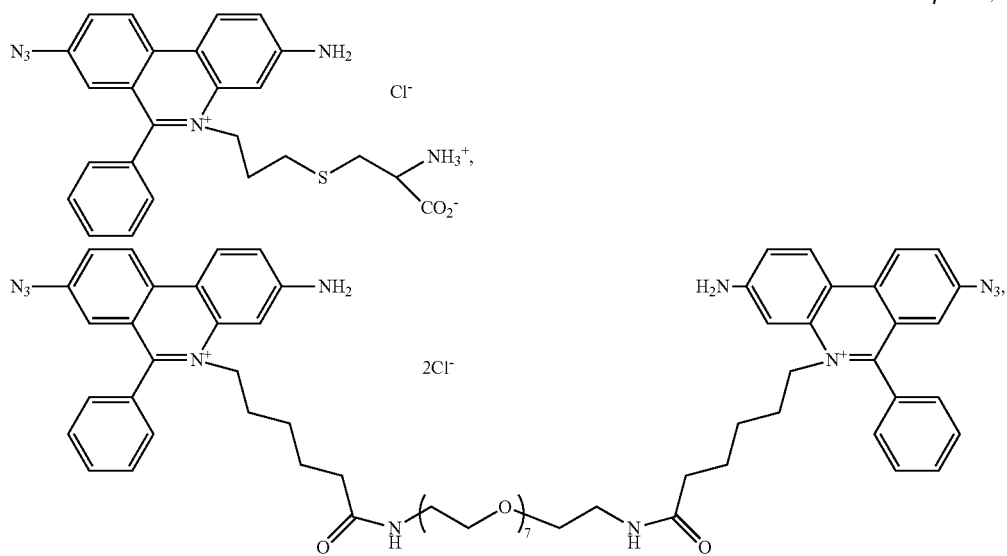
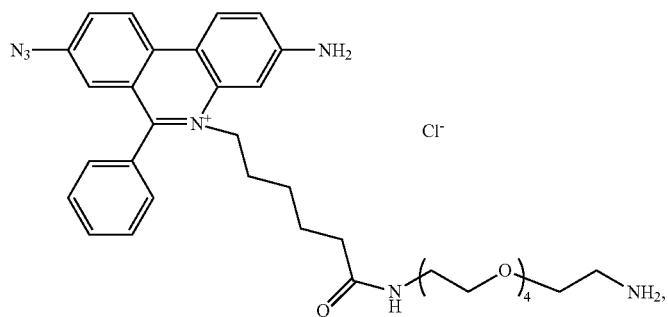

-continued

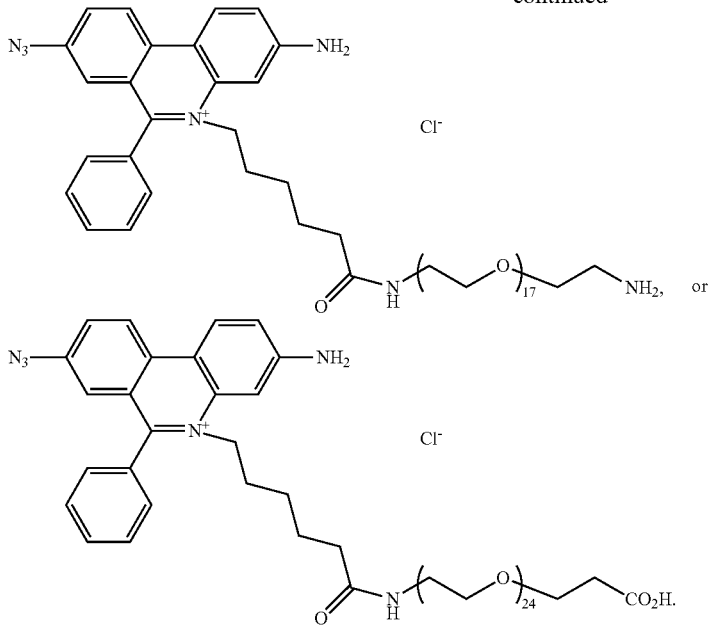

14. A method of selectively labeling a non-viable organism or non-viable cell, the method comprising contacting the compound of claim 1 with a sample comprising viable and non-viable organisms or cells to effect formation of a complex comprising the compound and a nucleic acid of the non-viable organism or non-viable cell, thereby selectively labeling the non-viable organism or non-viable cell in the sample.

* * * * *